United States Patent
Robl et al.

(10) Patent No.: US 7,420,099 B2
(45) Date of Patent: Sep. 2, 2008

(54) TRANSGENIC ANIMALS AND USES THEREOF

(75) Inventors: James M. Robl, Brandon, SD (US); Yoshimi Kuroiwa, Sioux Falls, SD (US); Poothappillai Kasinathan, Sioux Falls, SD (US); Isao Ishida, Isehara (JP); Kazuma Tomizuka, Takasaki (JP)

(73) Assignee: Kirin Holdings Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/111,310

(22) Filed: Apr. 21, 2005

(65) Prior Publication Data

US 2006/0041945 A1 Feb. 23, 2006

Related U.S. Application Data

(60) Provisional application No. 60/564,445, filed on Apr. 22, 2004.

(51) Int. Cl.
- *A01K 67/027* (2006.01)
- *C12P 21/00* (2006.01)
- *C12N 15/00* (2006.01)

(52) U.S. Cl. ............... 800/15; 800/6; 800/25
(58) Field of Classification Search ............... 800/15, 800/6, 25
See application file for complete search history.

(56) References Cited

U.S. PATENT DOCUMENTS

| | | | | |
|---|---|---|---|---|
| 4,797,356 | A | 1/1989 | Brandt et al. | 435/7 |
| 4,847,081 | A | 7/1989 | Rice | 424/186.1 |
| 4,873,316 | A | 10/1989 | Meade et al. | 530/412 |
| 4,959,317 | A | 9/1990 | Sauer | 435/172.3 |
| 4,994,384 | A | 2/1991 | Prather et al. | 435/172.3 |
| 5,021,244 | A | 6/1991 | Spaulding | 424/561 |
| 5,057,420 | A | 10/1991 | Massey | 435/172.2 |
| 5,096,822 | A | 3/1992 | Rosenkrans, Jr. et al. | 435/388 |
| 5,160,312 | A | 11/1992 | Voelkel | 600/34 |
| 5,175,384 | A | 12/1992 | Krimpenfort et al. | 800/2 |
| 5,213,979 | A | 5/1993 | First et al. | 435/240.2 |
| 5,320,952 | A | 6/1994 | Deutch et al. | 435/69.1 |
| 5,346,990 | A | 9/1994 | Spaulding | 530/412 |
| 5,374,544 | A | 12/1994 | Schwartz et al. | 435/69.1 |
| 5,434,066 | A | 7/1995 | Bebee et al. | 435/172.3 |
| 5,434,340 | A | 7/1995 | Krimpenfort et al. | 800/2 |
| 5,453,366 | A | 9/1995 | Sims et al. | 435/172.3 |
| 5,464,764 | A | 11/1995 | Capecchi et al. | 435/6 |
| 5,470,560 | A | 11/1995 | Martin, Jr. | 424/9.2 |
| 5,482,856 | A | 1/1996 | Fell, Jr. et al. | 435/320.1 |
| 5,487,992 | A | 1/1996 | Capecchi et al. | 435/172.3 |
| 5,496,720 | A | 3/1996 | Susko-Parrish et al. | 435/240.2 |
| 5,527,674 | A | 6/1996 | Guerra et al. | 435/6 |
| 5,545,806 | A | 8/1996 | Lonberg et al. | 800/2 |
| 5,545,807 | A | 8/1996 | Surani et al. | 800/2 |
| 5,565,350 | A | 10/1996 | Kmiec | 435/172.3 |
| 5,565,362 | A | 10/1996 | Rosen | 435/320.1 |
| 5,569,825 | A | 10/1996 | Lonberg et al. | 800/2 |
| 5,583,016 | A | 12/1996 | Villeponteau et al. | 435/91.3 |
| 5,591,669 | A | 1/1997 | Krimpenfort et al. | 800/2 |
| 5,612,205 | A | 3/1997 | Kay et al. | 435/172.3 |
| 5,614,396 | A | 3/1997 | Bradley et al. | 435/172.3 |
| 5,618,686 | A | 4/1997 | Kojima et al. | 435/26 |
| 5,625,126 | A | 4/1997 | Lonberg et al. | 800/2 |
| 5,627,059 | A | 5/1997 | Capecchi et al. | 800/21 |
| 5,631,153 | A | 5/1997 | Capecchi et al. | 435/172.3 |
| 5,633,076 | A | 5/1997 | DeBoer et al. | 435/172.3 |
| 5,633,425 | A | 5/1997 | Lonberg et al. | 800/2 |
| 5,639,457 | A | 6/1997 | Brem et al. | 424/184.1 |
| 5,652,373 | A | 7/1997 | Reisner | 800/11 |
| 5,654,182 | A | 8/1997 | Wahl et al. | 435/172.1 |
| 5,660,997 | A | 8/1997 | Spaulding | 435/7.21 |
| 5,661,016 | A | 8/1997 | Lonberg et al. | 435/172.3 |
| 5,677,177 | A | 10/1997 | Wahl et al. | 435/325 |
| 5,679,523 | A | 10/1997 | Li et al. | 435/6 |
| 5,695,977 | A | 12/1997 | Jurka | 435/172.3 |
| 5,698,763 | A | 12/1997 | Weissmann et al. | 800/2 |
| 5,721,367 | A | 2/1998 | Kay et al. | 800/2 |
| 5,733,730 | A | 3/1998 | De Lange | 435/6 |
| 5,741,957 | A | 4/1998 | Deboer et al. | 800/2 |
| 5,750,172 | A | 5/1998 | Meade et al. | 426/580 |
| 5,756,325 | A | 5/1998 | Kmiec | 435/172.3 |
| 5,763,240 | A | 6/1998 | Zarling et al. | 435/172.3 |
| 5,770,422 | A | 6/1998 | Collins | 435/194 |
| 5,770,429 | A | 6/1998 | Lonberg et al. | 435/240.2 |

(Continued)

FOREIGN PATENT DOCUMENTS

| EP | 0773288 | 5/1997 |
|---|---|---|
| EP | 0546073 | 9/1997 |
| EP | 0843961 | 5/1998 |
| EP | 1106061 | 6/2001 |
| WO | WO 92/03918 | 3/1992 |

(Continued)

OTHER PUBLICATIONS

Yang, Springer Semin. Immun. 26:187-200; 2004.*
Greiner et al. Stem Cell 16:166-177; 1998.*
Ahearn et al., "Disruption of the Cr2 Locus Results in a Reduction in B-1a Cells and in an Impaired B Cell Response to T-Dependent Antigen," *Immunity* 4:251-262 (1996).
Burke et al., "A Cell Free System to Study Reassembly of the Nuclear Envelope at the End of Mitosis," *Cell* 44:639-652 (1986).
Cibelli et al., "Bovine Chimeric Offspring Produced By Transgenic Embryonic Stem Cells Generated From Somatic Cell Nuclear Transfer Embryos," *Theriogenology* 49:236 (1998).

(Continued)

*Primary Examiner*—Joseph Woitach
*Assistant Examiner*—Fereydoun G. Sajjadi
(74) *Attorney, Agent, or Firm*—Clark & Elbing LLP; Karen L. Elbing

(57) ABSTRACT

In general, the invention features genetically modified non-human mammals (e.g., bovines and other ungulates), and methods of making these mammals. In particular, the invention features transgenic ungulates having reduced levels of endogenous IgM heavy chain and/or prion protein.

19 Claims, 26 Drawing Sheets

U.S. PATENT DOCUMENTS

| | | | |
|---|---|---|---|
| 5,776,744 A | 7/1998 | Glazer et al. | 435/172.3 |
| 5,780,009 A | 7/1998 | Karatzas et al. | 424/9.1 |
| 5,780,296 A | 7/1998 | Holloman et al. | 435/320.1 |
| 5,789,215 A | 8/1998 | Berns et al. | 435/172.3 |
| 5,789,650 A | 8/1998 | Lonberg et al. | 800/2 |
| 5,789,655 A | 8/1998 | Prusiner et al. | 800/2 |
| 5,801,030 A | 9/1998 | McVey et al. | 435/172.3 |
| 5,814,318 A | 9/1998 | Lonberg et al. | 424/184.1 |
| 5,821,117 A | 10/1998 | Sandrin et al. | 435/320.1 |
| 5,827,690 A | 10/1998 | Meade et al. | 435/69.6 |
| 5,830,698 A | 11/1998 | Reff et al. | 435/69.1 |
| 5,837,857 A | 11/1998 | Villeponteau et al. | 536/24.31 |
| 5,843,643 A | 12/1998 | Ratner | 435/6 |
| 5,843,754 A | 12/1998 | Susko-Parrish et al. | 435/240 |
| 5,849,991 A | 12/1998 | d'Apice et al. | 800/2 |
| 5,849,992 A | 12/1998 | Meade et al. | 800/2 |
| 5,874,299 A | 2/1999 | Lonberg et al. | 435/320.1 |
| 5,876,979 A | 3/1999 | Andrews et al. | 435/91.3 |
| 5,877,397 A | 3/1999 | Lonberg et al. | 800/2 |
| 5,891,698 A | 4/1999 | Prieto et al. | 435/67.1 |
| 5,945,577 A | 8/1999 | Stice et al. | 800/24 |
| 5,952,222 A | 9/1999 | Rosenkrans, Jr. et al. | 435/325 |
| 6,011,197 A | 1/2000 | Strelchenko et al. | 800/24 |
| 6,023,010 A | 2/2000 | Krimpenfort et al. | 800/2 |
| 6,030,833 A | 2/2000 | Seebach et al. | 435/325 |
| 6,054,632 A | 4/2000 | Reid | 800/6 |
| 6,066,719 A | 5/2000 | Zapata | 530/387.3 |
| 6,074,853 A | 6/2000 | Pati et al. | 435/91.1 |
| 6,077,710 A | 6/2000 | Susko-Parrish et al. | 435/375 |
| 6,091,001 A | 7/2000 | Jakobovits et al. | 800/18 |
| 6,133,503 A | 10/2000 | Scheffler | |
| 6,147,276 A | 11/2000 | Campbell et al. | 800/24 |
| 6,153,428 A | 11/2000 | Gustafsson et al. | 435/325 |
| 6,166,288 A | 12/2000 | Diamond et al. | 800/7 |
| 6,183,993 B1 | 2/2001 | Boyce et al. | 435/69.7 |
| 6,194,202 B1 | 2/2001 | Susko-Parrish et al. | 435/325 |
| 6,204,061 B1 | 3/2001 | Capecchi et al. | 435/463 |
| 6,204,431 B1 | 3/2001 | Prieto et al. | 800/14 |
| 6,252,133 B1 | 6/2001 | Campbell et al. | 800/24 |
| 6,258,998 B1 | 7/2001 | Damiani et al. | 800/24 |
| 6,271,436 B1 | 8/2001 | Piedrahita et al. | 800/21 |
| 6,300,129 B1 | 10/2001 | Lonberg et al. | 435/326 |
| 6,395,958 B1 | 5/2002 | Strelchenko et al. | 800/7 |
| 6,753,457 B2 | 6/2004 | Wangh et al. | |
| 2002/0001842 A1 | 1/2002 | Chapman | 435/449 |
| 2002/0012660 A1 | 1/2002 | Colman et al. | 424/93.21 |
| 2002/0069423 A1 | 6/2002 | Good et al. | |
| 2002/0108132 A1 | 8/2002 | Rapp | 800/6 |
| 2002/0194635 A1 | 12/2002 | Dunne et al. | |
| 2003/0037347 A1 | 2/2003 | Robl et al. | |
| 2004/0068760 A1 | 4/2004 | Robl et al. | |
| 2004/0131620 A1 | 7/2004 | Maeda et al. | |
| 2005/0097627 A1 | 5/2005 | Robl et al. | |
| 2005/0183145 A1 | 8/2005 | Goldsby et al. | |
| 2006/0117394 A1 | 6/2006 | Robl et al. | |
| 2006/0117395 A1 | 6/2006 | Robl et al. | |
| 2006/0130157 A1 | 6/2006 | Wells et al. | |

FOREIGN PATENT DOCUMENTS

| | | |
|---|---|---|
| WO | WO 93/10227 | 5/1993 |
| WO | WO 94/02602 | 2/1994 |
| WO | WO 95/23868 | 9/1995 |
| WO | WO 95/33828 | 12/1995 |
| WO | WO 96/33735 | 10/1996 |
| WO | WO 97/07668 | 3/1997 |
| WO | WO 97/07669 | 3/1997 |
| WO | WO 97/07671 | 3/1997 |
| WO | WO 97/13852 | 4/1997 |
| WO | WO 98/14593 | 4/1998 |
| WO | WO 98/24884 | 6/1998 |
| WO | WO 98/24893 | 6/1998 |
| WO | WO 98/30683 | 7/1998 |
| WO | WO 98/37183 | 8/1998 |
| WO | WO 98/39416 | 9/1998 |
| WO | WO 99/21415 | 5/1999 |
| WO | WO 99/60108 | 11/1999 |
| WO | WO 00/10383 | 3/2000 |
| WO | WO 00/42174 | 7/2000 |
| WO | WO 00/46251 | 8/2000 |
| WO | WO 00/51424 | 9/2000 |
| WO | WO 00/67568 | 11/2000 |
| WO | WO 00/67569 | 11/2000 |
| WO | WO 00/74477 | 12/2000 |
| WO | WO 01/23541 | 4/2001 |
| WO | WO 01/30992 | 5/2001 |
| WO | WO 01/35735 | 5/2001 |
| WO | WO 01/73107 | 10/2001 |
| WO | WO 02/12437 | 2/2002 |
| WO | WO 02/051997 | 7/2002 |
| WO | WO 02/070648 | 9/2002 |
| WO | WO 02/079416 | 10/2002 |
| WO | WO 2004/044156 | 5/2004 |

OTHER PUBLICATIONS

Cibelli et al., "Cloned Transgenic Calves Produced from Nonquiescent Fetal Fibroblasts," *Science* 280:1256-1258 (1998).

Collas et al., "Lipophilic Organizing Structures of Sperm Nuclei Target Membrane Vesicle Binding and Are Incorporated into the Nuclear Envelope," *Dev. Biol.* 169:123-135 (1995).

Collas, "Sequential PKC- and Cdc2-Mediated Phosphorylation Events Elicit Zebrafish Nuclear Envelope Disassembly," *J. Cell Sci.* 112:977-987 (1999).

Collas et al., "The A-Kinase Anchoring Protein, AKAP95, Is A Multivalent Protein With A Key Role In Chromatin Condensation At Mitosis," *J. Cell Biol.* 147:1167-1179 (1999).

Cubizolles et al., "pEg7, A New Xenopus Protein Required For Mitotic Chromosome Condensation in Egg Extracts," *J. Cell Biol.* 143:1437-1446 (1998).

Denning et al., "Deletion of the α(1,3)Galactosyl Transferase (*GGTA1*) Gene and the Prion Protein (*PrP*) Gene in Sheep," *Nat. Biotechnol.* 19:559-562 (2001).

Ehrenstein et al., "Targeted Gene Disruption reveals a Role for Natural Secretory IgM in the Maturation of the Primary Immune Response," *Proc. Natl. Acad. Sci., USA* 95:10089-10093 (1998).

Erlandsson et al., "Mice with an Inactivated joining chain Locus Have Perturbed IgM Secretion," *Eur. J. Immunol.* 28:2355-2365 (1998).

Goldman et al., "Enhanced Human Cell Engraftment in Mice Deficient in RAG2 and the Common Cytokine Receptor Gamma Chain," *Br. J. Haematol.* 103:335-342 (1998).

Guidos et al., "Development of CD4+CD8+ Thymocytes in RAG-Deficient Mice Through a T Cell Receptor β Chain-Independent Pathway," *J. Exp. Med.* 181:1187-1195 (1995).

Ishida et al., "Production of a Diverse Repertoire of Human Antibodies In Genetically Engineered Mice," *Microbiol. Immunol.* 42:143-150 (1998).

Jonak et al., "Manipulation of Human B Cells to Confer Immortality," *Hum. Antibodies Hybridomonas* 3:177-185 (1992).

Joziasse et al., "Bovine Alpha 1→3-Galactosyltransferase: Isolation and Characterization of a cDNA Clone. Identification of Homologous Sequences in Human Genomic DNA," *J. Biol. Chem.* 264:14290-14297 (1989).

Joziasse et al., "Characterization of an α1→3-Galactosyltransferase Homologue on Human Chromosome 12 That Is organized As A Processed Pseudogene," *J. Biol. Chem.* 266:6991-6998 (1991).

Kitamura et al., "A B Cell-Deficient Mouse by Targeted Disruption of the Membrane Exon of the Immunoglobulin Mu Chain Gene," *Nature* 350:423-426 (1991).

Knight et al., "Genetic Engineering of Bovine Ig. Construction and Characterization of Hapten-Binding Bovine/Murine Chimeric IgE, IgA, IgG1, IgG2, and IgG3 Molecules," *J. Immunol.* 140:3654-3659 (1988).

Kuroiwa et al., "Manipulation of Human Minichromosomes to Carry Greater Than Megabase-Sized Chromosome Inserts," *Nat. Biotechnol.* 18:1086-1090 (2000).

Lansford et al., "Ig Heavy Chain Class Switching in Rag-Deficient Mice," *Int. Immunol.* 10:325-332 (1998).

Lohka et al., "Formation In Vitro of Sperm Pronuclei and Mitotic Chromosomes Induced By Amphibian Ooplasmic Components," *Science* 220:719-721 (1983).

Lohka et al., "Induction of Nuclear Envelope Breakdown, Chromosome Condensation And Spindle Formation In Cell-Free Extracts," *J. Cell Biol.* 101:518-523 (1985).

Loupart et al., "Differential Stability of a Human Mini-Chromosome in Mouse Cell Lines," *Chromosoma* 107:255-259 (1998).

Martin et al., "Engraftment of Human Lymphocytes and Thyroid Tissue into Scid and Rag2-Deficient Mice: Absent Progression of Lymphocytic Infiltration," *J. Clin. Endocrinol. Metab.* 79:716-723 (1994).

Mazurier et al., "A Novel Immunodeficient Mouse Model—Rag2 x Common Cytokine Receptor Gamma Chain Double Mutants—Requiring Exogenous Cytokine Administration for Human Hematopoietic Stem Cell Engraftment," *J. Interferon cytokine Res.* 19:533-541 (1999).

Miake-Lye et al., "Induction of Early Mitotic Events in a Cell-Free System," *Cell* 41:165-175 (1985).

Mocikat, "Improving the Expression of Chimeric Antibodies Following Homologous Recombination in Hybridoma Cells," *J. Immunol. Methods* 225:185-189 (1999).

Newport, "Nuclear Reconstitution In Vitro: Stages of Assembly Around Protein-Free DNA," *Cell* 48:205-217 (1987).

Polejaeva et al., "New Advances In Somatic Cell Nuclear Transfer: Application In Transgenesis," *Theriogenology* 53:117-126 (2000).

Rideout et al., "Nuclear Cloning and Epigenetic Reprogramming of the Genome," *Science* 293:1093-1098 (2001).

Schnieke et al., "Human Factor IX Transgenic Sheep Produced By Transfer of Nuclei From Transfected Fetal Fibroblasts," *Science* 278:2130-2133 (1997).

Shen et al., "Human Mini-Chromosomes in Mouse Embryonal Stem Cells," *Hum. Mol. Genet.* 6:1375-1382 (1997).

Srikumaran et al., "Bovine X Mouse Hybridomas that Secrete Bovine Immunoglobulin G1," *Science* 220:522-524 (1983).

Steen et al., "A-Kinase-Anchoring Protein (AKAP)95 Recruits Human Chromosome-Associated Protein (hCAP)- D2/Eg7 For Chromosome Condensation In Mitotic Extract," *J. Cell Biol.* 149:531-536 (2000).

Steen et al., "Recruitment of Protein Phosphatase 1 to the Nuclear Envelope By A-Kinase Anchoring Protein AKAP149 Is A PreRequisite For Nuclear Lamina Assembly," *J. Cell Biol.* 150:1251-1261 (2000).

Suprynowicz et al., "A Fractionated Cell-Free System for Analysis of Prophase Nuclear Disassembly," *J. Cell Biol.* 103:2073-2081 (1986).

Tomizuka et al., "Double Trans-Chromosomic Mice: Maintenance of Two Individual Human Chromosome Fragments Containing Ig Heavy and Kappa Loci and Expression of Fully Human antibodies," *Proc. Natl. Acad. Sci, USA* 97:722-727 (2000).

Wilson et al., "A Trypsin-Sensitive Receptor On Membrane Vesicles Is Required For Nuclear Envelope Formation In Vitro," *J. Cell Biol.* 107:57-68 (1988).

Yahata et al., "Reconstitution of Immune Systems in RAG2 -/- Mice by Transfer with Interleukin-12-Induced Splenic Hematopoietic Progenitor Cells," *Immunol. Lett.* 62:165-170 (1998).

Leonard, et al. "Role of the Common Cytokine Receptor Gamma Chain in Cytokine Signaling and Lymphoid Development," *Immunological Reviews* 148:97-114 (1995).

Griffiths et al., "Current Concepts of PLP and Its Role in the Nervous Sytem," *Microscopy Research and Technique* 41:344-358 (1998).

Moens et al., "Defects in Heart and Lung Development in Compound Heterozygotes for Two Different Targeted Mutations at the N-Myc Locus," *Development* 119:485-499 (1993).

Kaushik et al., "Novel Insight Into Antibody Diversification From Cattle". *Veterinary Immunology and Immunopathology* 87:347-350 (2002).

Parng et al., "Gene Conversion Contributes to Ig Light Chain Diversity in Cattle," *J. Immunology* 157:5478-5486 (1996).

Echelard et al., Toward a New Cash Cow: Cloned cattle engineered to carry an artificial chromosome encoding human immunoglobulin genes are a significant leap toward the production of safer and more potent therapeutic antibodies, *Nat. Biotechnol.* 20:881-882, 2002.

Farrugia et al., Intravenous immunoglobulin: regulatory perspectives on use and supply, *Trans. Med.* 11:63-74, 2001.

Fishwild et al., High-avidity human IgGk monoclonal antibodies from a novel strain of minilocus transgenic mice, *Nat. Biotech.* 14:845-851, 1996.

Ishida et al., Production of human monoclonal and polyclonal antibodies in transchromo animals, *Clon. Stem Cells* 4:91-102, 2002.

Joziasse et al., Xenotransplantation: the importance of the Galα1,3Gal epitope in hyperacute vascular rejection, *Biochem. et BioPhys.* 1455:403-418, 1999.

Kuroiwa et al., Cloned transchromosomic calves producing human immunoglobulin, *Nat. Biotech.* 20:889-894, 2002.

Lonberg et al., Human antibodies from transgenic mice, *Intern. Rev. Immun.* 13:65-93, 1995.

Lucier et al., Multiple sites of Vλ diversification in cattle, *J. Immun.* 161:5438-5444, 1998.

Mendez et al., Functional transplant of megabase human immunoglobulin loci recapitulates human antibody response in mice, *Nat. Genet.* 15:146-156, 1997.

Raeber et al., Ectopic expression of prion protein (PrP) in T lymphocytes or hepatocytes of PrP knockout mice is insufficient to sustain prion replication, *Proc. Natl. Acad. Sci.* 96:3987-3992, 1999.

Sandrin et al., Recent advances in xenotransplantation, *Curr. Opin. in Immun.* 11:527-531, 1999.

Stiehm et al., Appropriate therapeutic use of immunoglobulin, *Trans. Med. Rev.* X:203-221, 1996.

Tomizuka et al., Functional expression and germline transmission of a human chromosome fragment in chimaeric mice, *Nat. Genet.* 16:133-143, 1997.

Baguisi et al., "Production of Goats by Somatic Cell Nuclear Transfer," *Nature Biotechnology* 17:456-461 (1999).

Co et al., "Generation of Transgenic Mice and Germline Transmission of a Mammalian Artificial Chromosome Introduced into Embryos by Pronuclear Microinjection," *Chromosome Research* 8:183-191 (2000).

Eyestone et al., "Nuclear Transfer from Somatic Cells: Applications in Farm Animal Species," *Journal of Reproduction and Fertility* 54:489-497 (1999).

Grimes et al., "Engineering Mammalian Chromosomes," *Human Molecular Genetics* 7:1635-1640 (1998).

Langford et al., "Production of Pigs Transgenic for Human Regulators of Complement Activation Using YAC Technology," *Transplantation Proceedings* 28:862-863 (1996).

Niemann et al., "Transgenic Livestock: Premises and Promises," *Animal Reproduction Science* 60-61:277-293 (2000).

Prather et al., "Development of the Techniques for Nuclear Transfer in Pigs," *Theriogenology* 51:487-498 (1999).

Sun et al., "Expressed Swine $V_H$ Genes Belong to a Small $V_H$ Gene Family Homologous to Human $V_H$III," *The Journal of Immumnology* 153:5618-5627 (1994).

Zhao et al., "Artiodactyl IgD: The Missing Link," *The Journal of Immunology* 169:4408-4416 (2002).

Zuelke, "Transgenic Modification of Cows Milk for Value-Added Processing," *Reproduction, Fertility, Development* 10:671-676 (1998).

Clark et al., "A future for Transgenic livestock." Nature Reviews: *Genetics* 4:825-833 (2003).

Niemann et al., Transgenic Farm animals: Present and Future. *Rev. Schi. Tech. Off. Int. Spiz* 24:285-298 (2005).

Wheeler et al., "Transgenic Technology and Applications in Swine," *Theriogenology* 56:1345-1369 (2001).

Prelle et al., "Pluripotent Stem Cells- Models of Embryonic Development, Tool for Gene Targeting, and Basis of Cell Therapy," *Anat. Histol. Embryol.* 31:169-186 (2002).

Pennisi et al., "Clones: A Hard Act to Follow," *Science* 288:1722-1727 (2000).

Campbell, "Nuclear Transfer in Farm Animal Species," *Seminars in Cell & Develop. Biol.* 10:245-252 (1999).

Weissman, "Molecular Biology of Transmissible Spongiform Encephalopathies," *FEBS Letters* 389:3-11 (1996).

Hamers-Casterman et al. "Naturally Occurring Antibodies Devoid of Light Chains," *Nature* 363:446-448 (1993).

Bosch et al., "Isolation, Characterization, Gene Modification, and Nuclear Reprogramming of Porcine Mesenchymal Stem Cells," *Biology of Reproduction* 74:46-57 (2006).

Dai et al., "Targeted Disruption of the α1,3-Galactosyltransferase Gene in Cloned Pigs," *Nature Biotechnology* 20:251-255 (2002).

Hyun et al., "Production of Nuclear Transfer-Derived Piglets Using Porcine Fetal Fibroblasts Transfected with the Enhanced Green Fluorescent Protein," *Biology of Reproduction* 69:1060-1068 (2003).

Lai et al., "Production of α1,3-Galactosyltransferase Knockout Pigs by Nuclear Transfer Cloning," *Science* 295:1089-1092 (2002).

Lai et al., "Creating Genetically Modified Pigs by Using Nuclear Transfer," *Reproductive Biology and Endocrinology* 1:1-6 (2003).

Keefer et al., "Generation of Dwarf Goat (*Capra hircus*) Clones Following Nuclear Transfer with Transfected and Nontransfected Fetal Fibroblasts and In Vitro-Matured Oocytes," *Biology of Reproduction* 64:849-856 (2001).

Martinez Diaz et al., "Effect of Fusion/Activation Protocol on In Vitro Development of Porcine Nuclear Transfer Embryos Constructed with Foreign Gene-Transfected Fetal Fibroblasts," *J. Vet. Med. Sci* 65:989-994 (2003).

Park et al., "Developmental Potential of Porcine Nuclear Transfer Embyros Derived From Transgenic Fetal Fibroblasts Infected with the Gene for the Green Fluorescent Protein: Comparison of Different Fusion/Activation Conditions," *Biology of Reproduction* 65:1681-1685 (2001).

Prather et al., "Nuclear Remodeling and Reprogramming in Transgenic Pig Production," *Exp. Biol. Med* 229:1120-1126 (2004).

Ramsoondar et al., "Production of α1,3-Galactosyltransferase-Knockout Cloned Pigs Expressing Human α1,2-Fucosylosyltransferase," *Biology of Reproduction* 69:437-445 (2003).

Watanabe et al., "A Novel Method for the Production of Transgenic Cloned Pigs: Electroporation-Mediated Gene Transfer to Non-cultured Cells and Subsequent Selection with Puromycin," *Biology of Reproduction* 72:309-315 (2005).

Clark et al., "Gene Targeting in Livestock: A Preview," Transgenic Research 9:263-275 (2000).

Denning et al., "Gene Targeting in Primary Fetal Fibroblasts from Sheep and Pig," Cloning and Stem Cells 3:221-231 (2001).

Leno et al., "Initiation of DNA Replication in Nuclei from Quiescent Cells Requires Permeabilization of the Nuclear Membrane," The Journal of Cell Biology 127:5-14 (1994).

U.S. Appl. No. 11/789,961, filed Apr. 26, 2007, Wells et al.

U.S. Appl. No. 60/794,963, filed Apr. 26, 2006, Wells et al.

U.S. Appl. No. 60/621,433, filed Oct. 22, 2004, Wells et al.

\* cited by examiner

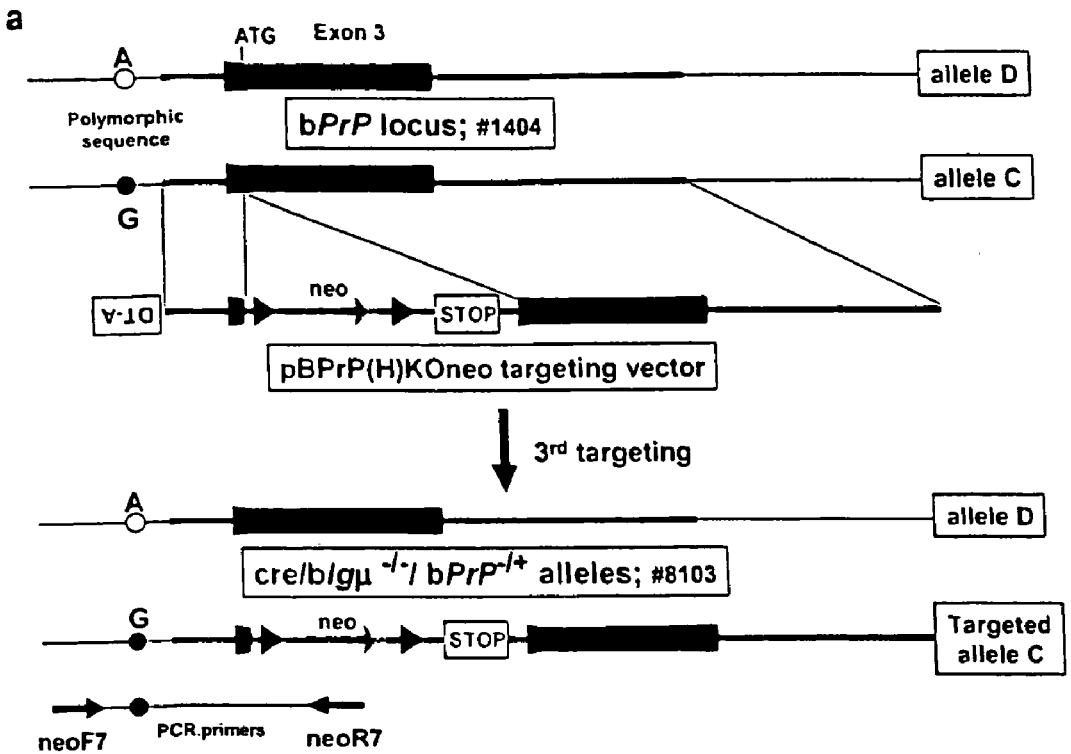
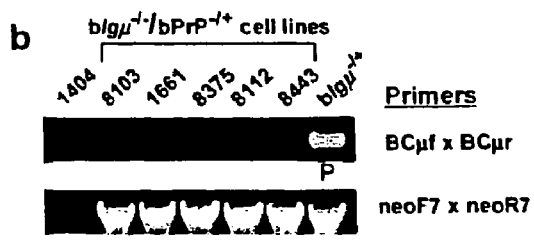
Fig. 5

Fig. 7

```
GTCCTGGTCAACAGTGGGCTGGCCTCAGTGATCTGGTTGTGCTGAGGACTGGGGGCCTGAGTGTGTATAG
TCTTATTGATGACCCCAGACCCCCAGAGCAGGCCCCAGGTGGCTGAGCTGTGGGCAGTGGAGGGTGGGCT
GGTAGGGCTGAGTGTGCCCTCCACTCCACTGTCCCAGAGAGAAGGTAGAGCTGCCCACACCCCCAACCAG
CAGGATGCCTCACACCCCCCTCTTCTCCTGTGTCCTCTCTCGGGTCCCCAGAAGGTGAATCACACCCGAA
AGTCTTCCCCCTGGTGTCCTGCGTGAGCTCGCCATCCGATGAGAGCACGGTGGCCCTGGGCTGCCTGGCC
CGGGACTTCGTGCCCAATTCAGTCAGCTTCTCCTGGAAGTTCAACAACAGCACAGTCAGCAGCGAGAGAT
TCTGGACCTTCCCCGAAGTCCTGAGGGACGGCTTGTGGTCGGCCTCCTCTCAGGTGGTCCTGCCCTCCTC
AAGCGCCTTTCAAGGGCCGGATGACTACCTGGTGTGCGAAGTCCAGCACCCCAAGGGAGGAAAGACCGTC
GGCACCGTGAGGGTGATCGCTACAAGTGAGTCGGGCCCGTCCCGTGGTTGGGTGCAGGGGAGGGTCCAGG
CCCCGCTGACCTCTTGTCCTTCTCTGCAGAGGCGGAAGTGCTGTCCCCAGTCGTGAGTGTCTTTGTCCCG
CCTCGCAACAGCCTCTCTGGTGACGGCAATAGCAAGTCCAGCCTCATCTGCCAGGCCACGGACTTCAGCC
CCAAACAGATCTCGTTGTCCTGGTTTCGTGATGGAAAGCGGATAGTGTCTGGAATTTCTGAAGGCCAGGT
GGAGACTGTGCAGTCCTCACCCATAACCTTCAGGGCCTACAGCATGCTGACCATCACGGAGAGAGACTGG
CTCAGCCAGAACGCGTACACCTGCCAGGTAGAACACAACAAGGAAACCTTCCAGAAGAACGTGTCCTCCT
CATGTGATGTTGGTGAGTGCAGCCCTGGGGGGCGGGCGCTCACCCTCAGGTCTGCAGACACCGCCCCAGA
CCTGCCAGCTGCTCCCTGAGCCTTGGCTTCCCAGAGCGGCAAGGGCAGGAGGGGCTGTGCAGGGCGGCTG
GGGGCCGGCACCCCTCCAACAGGGCCCCAGGTTCACAGGGGACTCAGCCAAGTGGGCCCTGGTCTTTGGG
CGGACCTCTCCCTTCACCTGATTTCACTCCAAGCAACTCTCTCCCACCTCCAGCACCACCATCTCCGATC
GGGGTCTTCACCATCCCCCATCCTTCGCCGACATCTTCCTCACGAAGTCAGCCAAGCTGTCCTGTCTGG
TCACAAACCTGGCCTCCTATGATGGCCTGAACATCAGCTGGTCCCGTCAGAACGCCAAGGCCCTGGAGAC
CCACACGTATTTTGAGCGACACCTCAACGACACCTTCAGCGCCCGGGGTGAGGCCTCGGTCTGCTCGGAG
GACTGGGAGTCCGGAGAGGAGTTCACGTGCACAGTGGCCCACTCGGACCTGCCCTTCCCAGAAAAGAACG
CCGTCTCCAAGCCCAAAGGTAGGCCCTGCCCTGCCCTGCCCTCCACCCCAGACCCTCCCCCGGCTTCTG
CCTTCTGAGGACAGCAGGCTAGGGCCAGCAGAGGTCCCACACTCGCCGATCTCACCACTGTGACCCCCTC
CCCCACCCAGACGTCGCCATGAAACCGCCGTCCGTGTACCTGCTGCCTCCAACGCGGGAACAGCTGAGCC
TGCGCGAGTCGGCCTCCGTCACCTGCCTGGTGAAGGCGTTCGCGCCCGCGGACGTGTTCGTGCAGTGGCT
GCAGAGGGGGGAGCCCGTGACCAAGAGCAAGTACGTGACCAGCGCCCGCGCGCCCGAGCCCCAGGACCCC
AGCGTGGTGTACTTTGTGCACAGCATCCTGACGGTGGCCGAGGAGGACTGGAGCAAAGGGGAGACCTACA
CCTGCGTCGTGCACGAAGCCCTGCCCCACATGGTCACCGAGCGGACCGTGGACAAGTCCACCGGTAAACC
CACCCTGTACAACGTGTCCCTGGTCCTGTCTGACACAGCCAGCACCTGCTACTGATGCCTGGTCAGAGCC
CCCGGGTGACCGTCGCTGTGTGTGTGCATGAGTGCAGACTAACCGTGTCGGTGCGCGAGATGCTGCGTTC
TCTAAAAATTAGAAATAAAAAGATCCATTCAAAGTGTGGTTGTGAGTGAGCAAAGCTCTCCCTGCTAGGC
CCGTGGCTCTCTGCCTCACCTTGCAAGAACCACCTCCATCATCCGCACCCCCGCCTCCCCACTCGCTTCC
AACCCACGCGCAGGAGCCCAGTGCTCCTTGTGGGATGCTCACAGCGGGCCAAGCCCATGCTCGCTGTGCC
TCGAGTCGCTTCCATGGCCACACTGGGGGCACACGGGTGTGCAACACACACACATGCACAGTCACATACA
TACATGCAGAGAGACACATGTGTGCACACACATGCATGGACACGCAGACAGCACGCACATGGACAGAGAC
CTGGGCACACGTGACACAGACATGTATATGATGGAATGGGTGAGCAGGCACACACACATGGACACATGAA
ACATGTGGACACACAGACACACATGTACACGCGCACTCACACGCAAGTGCACACAGTCACTCATAGGCAC
ATGCACATGGGCACTCACAGACACACACGCATGAGGACGAGTCATACACATGTAGACACACACGCACAGA
TGTACACACGCTCATGCACACATGAATGCACTGCACACATCCAGGCTCACACACTCGGATCCCAGCCCTT
GGACACCCCGTGCTCACTCAGTGCCCTGTCTGGGGGGTTCCTCTGCACCATGCCCGTGCTCTGCTTGTCC
CTCTGTCTCAGCTGGGAGGTACATTTGGAGGCCGCCCAAACCCAGCCCCAGACCAGGGTGCGCAGCGGG
CCACTCTGGGCCTGGCCAGAGGCAGCTCCTCAGGAAACTCATGGCCCCTGTCCAGGAGGGATGCTTCTCC
CAGTCCAGGCCCTTGTGAAGGTGGCAGGGCCCCAGCTCTCCCCTTTCCCTGTGAAGAGACAGAGTCAGTC
GTGTCCTGACAGCGGGCCATGCCTGGGAGGCCCCCCTTGGAGTATGCAGCTGCAGGGCCACACGTCAACC
TGGAGTGATAGGCACTGATCCGACGGGCAAGCGGGTCTCCTCTGCCACCCACACCAGTGCCCTTCAGGCT
GACTCCCTACCTCCCCTACACTCCTGGATCTTTATGGACCAAGGGCCCATCAGTGTAGTGTCTGCAGAAC
TAGGTGACTGTCCTCAGCCTTTGTCCCACGTCACTCTCCCTGGGTCTCAGATGTCTATCTGAACTCCTGA
TCCCACAGCTGTGAGTCCTGCAGTTCAGGCCCCAGCGAGGGCCCCACAAGGCCTCTCTCGTACATGCCAT
GTCTTCAAGGCAGAGAGAGATGGAGGCCAGAGGGATGGGCCCCTTGGCACAGGCAGACATCTGCCCCCAG
GGCTTGTGCCTCACTGGCTAGGGAGCCGACCTCAAACCACCAGAGACAGGACGCCCCACCACCGCTGTCA
GCCCCAAGTGGCCCTGAGTCCTCCAGAGGGGTCGAGGACACCTGGCCACTCCCCACCTCCAGCCCAGCG
AGACCCCACCCTTGTGTGTACGCGTGTGCTCTGTCTCGCTCTGTGCCACCCCGGCGCTCCTAGGGCCAGG
CACTCGGGGCCACTGCTTGGCTCAGCCTCAGCCACGCTCTGCCCCTGCAGGCTGTGGAATTGGGCGGCCA
GGGGCCTACCAGTCCTGGCTAAGACGCTGCCTGTCAAGTCCTGGAGCTCCCAACTGCCCCGGGGGTGCCG
GGGAGGCAGGCACACGCCTGCTCGCCTGCCCGCTCGCTTCTGAAGTCCCCCAACCCTTCTGATGGGTCAG
GGCGGCCGAGGGGGGCCAGGCCGGGCTCTGCGGGCAGCTCAGCCGTGTGACCACCGTGCCCTATCTCCCA
```

Fig. 7

```
CAGAGGGGGAGGTGAGCGCCGAGGAAGAAGGCTTTGAAAACCTCAACACCATGGCCTCCACCTTCATCGT
GCTCTTCCTCCTGAGCCTCTTCTACAGCACCACGGTCACCCTGTTCAAGGTAGCCGCATCGTCCCGAGGA
GGGGGTGAGGCCACAGAGCCCCGGGGCCGCAGATGCCCACGCACGCACTCACGCTGTCTCTGTCGCCTGC
AGGTGAAGTGATGGCCAGCCAAGAACATGGGGCACCGGAGACGGAACACGAGGGGCTGCCTTGGGGCCGG
GTCCCTGGCCTATGTGGCTTGTCCGCTTGTACTGAAATTTTCCCTGCGTCCTCTCCAGCTTCAAGCTGTA
AGAAACTGGCTTTTCTCGGAGCAGCTGAGTGCCATGGCCAAGCATGGAGCCCGCAGTAATAGGCTCCACC
TGGCCCTGCTTTGCAATGTCGCATTTGTGGCCTTGAAATAAA
```

Fig. 8

```
TCTAGATGGACTGAGCTGACCCCACTGGACTGTCCTGGTCAACAGTGGGCTGGCCTCAGTGATCTGGTTG
TGCTGAGGACTGGGGGCCTGAGTGTGTATCAGTCTTATTGATGACCCCAGACCCCCAGAGCAGGCCCCAG
GTGGCTGAGCTGTGGGCAGTGAGGGTGGGCTGGTAGGGCTGAGTGTGCCCTCCACTCCACTGTCCCAGAG
AGAAGGTAGAGCTGCCCACACCCCCAACCAGCAGGATGCCTCACACCCCCCTCTTCTCCTGTGTCCTCTC
TCGGGTCCCCAGAAGGTGAATCGCTCCCGAGAGTCTTCCCCCTGGTGTCCTGCATGAGCTCCCCATCCGA
TGAGAGCACGGTGGCCCTGGGCTGCCTGGCCCAGGACTTCATGCCCAATTCAGTCAGCTTCTCCTGGAAG
TTCAACAACAGCACAGTCGGCAGCGAGAGATTCTGGACCTTCCCCGCAGTCCTGAGGGACGGCTTGTGGT
CGGCCTCCTCTCAGGTGGTCCTGCCCTCCTCAAGCGCCTTTCAAGGGCCGGATGACTACCTGGTGTGCGA
AGTCCAGCACCCCAAGGGAGGAAAGACCGTCGGCACCGTGAGGGTGGTCACTCCAAGTGAGTCGGGCCCG
TCCCGTGGTTGGGTGCAGGGGAGGGTCCAGGCCCCGCTGACCTCTTGTCCTTCTCTGCAGAGGCAGAAGT
GCTGTCCCCCATCGTGAGTGTCTTTGTCCCGCCTCGCAACAGCCTCTCTGGTGACGGCAATAGCAAGTCC
AGCCTCATCTGCCAGGCCACGGACTTCAGCCCCAAACAGATCTCCTTGTCCTGGTTTCGTGATGGAAAGC
GGATAGTGTCTGGCATTTCTGAAGGCAGGTGGAGACTGTGCAGTCCTCACCCATAACTTTCAGGGCCTA
CAGCATGCTGACCATCACAGAGAAAGACTGGCTCAGCCAGAACGTGTACACCTGCCAGGTAGAACACAAC
AAGGAAACCTTCCAGAAGAACGTGTCCTCCTCATGTAATGTTGGTGAGTGCAGCCCTGGGGGGCGGGCGC
TCACCCTCAGGTCTGCAGACACCGCCCAGACCTGCCAGCTGCTCCCTGAGCCTTGGCTTCCCAGAGCGG
CCAAGGGCAGGAGGGGCTGTGCAGGGCGGCTGGGGCCGGCACCCCTCCAACAGGGCCCCAGGTTCACAG
GGGACTCAGCCAAGTGGGCCCTGCTCTTTGGGCGGACCTCTCCCTTCACCTGATTTCACTCCAAGCAACT
CTCTCCCACCTCCAGCACCACCATCTCCCATCGGGGTCTTCACCATCCCCCCATCCTTCGCCGACATCTT
CCTCACGAAGTCAGCCAAGCTGTCCTGTCTGGTCACAAACCTGGCCTCCTATGATGGCCTGAACATCAGC
TGGTCCCGTCAGAACGGCAAGGCCCTGGAGACCCACACTTATTTGGGAGACACCTCAACGACACCTTCA
GCGCCCGGGGTGAGGCCTCGGTCTGCTCGGAGGACTGGGAGTCCGGAGAGGAGTTCACGTGCACAGTGGC
CCACTCGGACCTGCCCTTCCCAGAAAAGAACACCGTCTCCAAGCCCAAAGGTAGGCCCTGCCCTGCCCCT
GCCCTCCACCCCAGACCCTCCCCCGGCTTCTGCCTTCTGAGGACAGCAGGCAGGGCCAGCAGAGGACCCA
CACTCGCCGATCTCACCACTGTGACCCCCTCCCCCACCCAGACGTCGCCATGAAACCGCCGTCCGTGTAC
CTGCTGCCTCCAACGCGGGAACAGCTGAGCCTGCGGGAGTCGGCCTCCGTCACCTGCCTGGTGAAGGGCT
TCGCGCCCGCGGACGTGTTCGTGCAGTGGCTGCAGAGGGGGGAGCCCGTGACCAAGAGCAAGTACGTGAC
CAGCAGCCCGGCGCCCGAGCCCCAGGACCCCAGCGTGTACTTTGTGCACAGCATCCTGACGGTGGCCGAG
GAGGACTGGAGCAAAGGGGAGACCTACACCTGCGTCGTGGGCCACGAGGCCCTGCCCCACATGGTCACCG
AGCGGACCGTGGACAAGTCCACCGGTAAACCCACCCTGTACAACGTGTCCCTGGTCCTGTCTGACACAGC
CAGCACCTGCTACTGATGCCTGGTCAGAGCCCCGGGTGACCGTCGCTGTGTGTGCATGAGTGCAGAC
TAACCGTGTCGGTGCGCGAGATGCTGCGTTCTCTAAAAATTAGAAATAAAAAGATCCATTCAAAGCTGCT
GGTTGTGAGTGAGCAAAGCTCTCCCTGCTAGGCCCGTGGCTGTCTGCCCTCACCTTGCAGACCACCTCCA
TCATCCGCACCCCGCCTCCCCACTCGCTTCCAACCCACGCCCAGGAGCCCCAGTGCTCCTTGTGGGATG
CTCACAGCAGGCCAAGCCCATGCTCGCTGTGCCTCGAGTCGCTTCCATGGCCACACTGGGGGCACACGGG
TGTGCAACACACACACATGCACAGTCACATACATACATGCAGAGAGACACATGTGTGCACACACATGCAT
GGACACGCAGACAGCACGCACATGGACAGAGACCTGGGCACACGTGACACAGACATGTATATGATGGAAT
GGGTGAGCAGGCACACACACATGGACACATGAAACATGTGGACACACAGACACACATGTACACGCGCACT
CACACGCAAGTGCACACAGTCACTCATAGGCACATGCACATGGGCACTCACAGACACACACGCATGAGGA
CGAGTCATACACATGTAGACACACACGCACAGATGTACACACGCTCATGCACACATGAATGCACTGCACA
CATCCAGGCTCACACACTCGGATCCCAGCCCTTGGACACCCCGTGCTCACTCAGTGCCCTGTCTGGGGGG
TTCCTCTGCACCATGCCCGTGCTCTGCTTGTCCCTCTGTCTCAGCTGGGAGGTACATTTGGAGGCCGCCC
CAAACCCAGCCCCAGACCAGGGTGCGCAGCGGGCCACTCTGGGCCTGGCCAGAGGCAGCTCCTCAGGAAA
CTCATGGCCCCTGTCCAGGAGGGATGCTTCTCCCAGTCCAGGCCCTTGTGAAGGTGGCAGGGCCCCAGCT
CTCCCCTTTCCCTGTGAAGAGACAGAGTCAGTCGTGTCCTGACAGCGGGCCATGCCTGGGAGGCCCCCT
TGGAGTATGCAGCTGCAGGGCCACACGTCAACCTGGAGTGATAGGCACTGATCCGACGGGCAAGCGGGTC
TCCTCTGCCACCCACACCAGTGCCCTTCAGGCTGACTCCCTACCTCCCCTACACTCCTGGATCTTTATGG
ACCAAGGGCCCATCAGTGTAGTGTCTGCAGAACTAGGTGACTGTCCTCAGCCTTTGTCCCACGTCACTCT
CCCTGGGTCTCAGATGTCTATCTGAACTCCTGATCCCACAGCTGTGAGTCCTGCAGTTCAGGCCCCAGCG
AGGGCCCCACAAGGCCTCTCTCGTACATGCCATGTCTTCAAGGCAGAGAGAGATGGAGGCCAGAGGGATG
GGCCCCTTGGCACAGGCAGACATCTGCCCCAGGGCTTGTGCCTCACTGGCTAGGGAGCCGACCTCAAAC
CACCAGAGACAGGACGCCCCACCACCGCTGTCAGCCCAAGTGGCCCTGAGTCCTCCAGAGGGGTCGAGG
ACACCTGGCCACTCCCCACCTCCAGCCCAGCGAGACCCCACCCTTGTGTGTACGCGTGTGCTCTGTCTC
GCTCTGTGCCACCCCGGCGCTCCTAGGGCCAGGCACTCGGGGCCACTGCTTGGCTCAGCCTCAGCCACGC
TCTGCCCCTGCAGGCTGTGGAATTGGGCGGCCAGGGGCCTACCAGTCCTGGCTAAGACGCTGCCTGTCAA
GTCCTGGAGCTCCCAACTGCCCCGGGGGTGCCGGGAGGCAGGCACACGCCTGCTCGCCTGCCCGCTCGC
TTCTGAAGTCCCCCAACCCTTCTGATGGGTCAGGGCGGCCGAGGGGGGCCAGGCCGGGCTCTGCGGGCAG
```

Fig. 8

```
CTCAGCCGTGTGACCACCGTGCCCTATCTCCCACAGAGGGGGAGGTGAGCGCCGAGGAAGAAGGCTTTGA
AAACCTCAACACCATGGCCTCCACCTTCATCGTGCTCTTCCTCCTGAGCCTCTTCTACAGCACCACGGTC
ACCCTGTTCAAGGTAGCCGCATCGTCCCGAGGAGGGGGTGAGGCCACAGAGCCCCGGGGCCGCAGATGCC
CACGCACGCACTCACGCTGTCTCTGTCGCCTGCAGGTGAAGTGATGGCCAGCCAAGAACATGGGGCACCG
GAGACGGAACACGAGGGGCTGCCTTGGGGCCGGGTCCCTGGCCTATGTGGCTTGTCCGCTTGTACTGAAA
TTTTCCCTGCGTCCTCTCCAGCTTCAAGCTGTAAGAAACTGGCTTTTCTCGGAGCAGCTGAGTGCCATGG
CCAAGCATGGAGCCCGCAGTAATAGGCTCCACCTGGCCCTGCTTTGCAATGTCGCATTTGTGGCCTTGAA
ATAAA
```

Fig. 9

```
GAGAGTCTTCCCCCTGGTGTCCTGCGTGAGCTCGCCATCCGATGAGAGCACGGTGGCCCTGGGCTGCCTG
GCCCGGGACTTCGTGCCCAATTCAGTCAGCTTCTCCTGGAAGTTCAACAACAGCACAGTCAGCAGCGAGA
GATTCTGGACCTTCCCCGAAGTCCTGAGGGACGGCTTGTGGTCGGCCTCCTCTCAGGTGGTCCTGCCCTC
CTCAAGCGCCTTTCAAGGGCCGGATGACTACCTGGTGTGCGAAGTCCAGCACCCCAAGGGAGGAAAGACC
GTCGGCACCGTGAGGGTGATCGCTACAAAGGCGGAAGTGCTGTCCCCAGTCGTGAGTGTCTTTGTCCCGC
CTCGCAACAGCCTCTCTGGTGACGGCAATAGCAAGTCCAGCCTCATCTGCCAGGCCACGGACTTCAGCCC
CAAACAGATCTCCTTGTCCTGGTTTCGTGATGGAAAGCGGATAGTGTCTGGAATTTCTGAAGGCCAGGTG
GAGACTGTGCAGTCCTCACCCGTAACTTTCAGGGCCTACAGCATGCTGACCATCACGGAGAGAGACTGGC
TCAGCCAGAACGTGTACACCTGCCAGGTAGAACACAACAAGGAAACCTTCCAGAAGAACGTGTCCTCCTC
ATGTGATGTTGCACCACCATCTCCCATCGGGGTCTTCACCATCCCCCCATCCTTCGCCGACATCTTCCTC
ACGAAGTCAGCCAAGCTGTCCTGTCTGGTCACAAACCTGGCCTCCTATGATGGCCTGAACATCAGCTGGT
CCCGTCAGAACGGCAAGGCCCTGGAGACCCACACGTATTTTGAGCGACACCTCAACGACACCTTCAGCGC
CCGGGGTGAGGCCTCGGTCTGCTCGGAGGACTGGGAGTCCGGAGAGGAGTTCACGTGCACAGTGGCCCAC
TCGGACCTGCCCTTCCCAGAAAAGAACAGCGTCTCCAAGCCCAAAGACGTCGCCATGAAACCGCCGTCCG
TGTACCTGCTGCCTCCAACGCGGGAACAGCTGAGCCTGCGGGAGTCGGCCTCCGTCACCTGCCTGGTGAA
GGGCTTCGCGCCCGCGGACGTGTTCGTGCAGTGGCTGCAGAGGGGGGAGCCCGTGACCAAGAGCAAGTAC
GTGACCAGCAGCCCGGCGCCCGAGCCTCAGGACCCCAGCGTGTACTTTGTGCACAGCATCCTGACGGTGG
CCGAGGAGGACTGGAGCAAAGGGGAGACCTACACCTGCGTCGTGGGCCACGAGGCCCTGCCCCACATGGT
CACCGAGCGGACCGTGGACAAGTCCACCGGTAAACCCACCCTGTACAACGTGTCCCTGGTCCTGTCTGAC
ACAGCCAGCACCTGCTGCTGATGCCTGGTCAGAGCCCCGGGTGACCGTCGCTGTGTGTGCATGAGTGCA
GACTAACCGTGTCGGTGCGCGAGATGCTGCACTCTATAAAAATTAGAAATAAAAAGATCCATTCAAAAAA
AAAAAAAAAAAA
```

```
CCGGGAATGGCGGCAGAGAGGGGCGGGGTGTCCTTGGGGC ⎤
CCGGGAATGGCGGCAGAGAGGGGCGGGGTGTCCTTGGGGC |  AY
CCGGGAATGGCGGCAGAGAGGGGCGGGGTGTCCTTGGGGC |
CCGGGAATGGCGGCAGAGAGGGGCGGGGTGTCCTTGGGGC ⎦
CCGGGAATGGCGGCAGAGAGGGGTGGGGTGTCCTCGGGGC ⎤
CCGGGAATGGCGGCAGAGAGGGGTGGGGTGTCCTCGGGGC |
CCGGGAATGGCGGCAGAGAGGGGTGGGGTGTCCTCGGGGC |
CCGGGAATGGCGGCAGAGAGGGGTGGGGTGTCCTCGGGGC |  ay
CCGGGAATGGCGGCAGAGAGGGGTGGGGTGTCCTCGGGGC |
CCGGGAATGGCGGCAGAGAGGGGTGGGGTGTCCTCGGGGC |
CCGGGAATGGCGGCAGAGAGGGGTGGGGTGTCCTCGGGGC |
CCGGGAATGGCGGCAGAGAGGGGTGGGGTGTCCTCGGGGC ⎦

CCGGCGTGGCGCCACTGGCCTGGGAGGAGACACACGTCCC ⎤
CCGGCGTGGCGCCACTGGCCTGGGAGGAGACACACGTCCC |  AY
CCGGCGTGGCGCCACTGGCCTGGGAGGAGACACACGTCCC |
CCGGCGTGGCGCCACTGGCCTGGGAGGAGACACACGTCCC ⎦
CCGGCGTGGCGCCACTGGCCTGGGAGGAGACACATGTCCC ⎤
CCGGCGTGGCGCCACTGGCCTGGGAGGAGACACATGTCCC |
CCGGCGTGGCGCCACTGGCCTGGGAGGAGACACATGTCCC |
CCGGCGTGGCGCCACTGGCCTGGGAGGAGACACATGTCCC |
CCGGCGTGGCGCCACTGGCCTGGGAGGAGACACATGTCCC |  ay
CCGGCGTGGCGCCACTGGCCTGGGAGGAGACACATGTCCC |
CCGGCGTGGCGCCACTGGCCTGGGAGGAGACACATGTCCC |
CCGGCGTGGCGCCACTGGCCTGGGAGGAGACACATGTCCC |
CCGGCGTGGCGCCACTGGCCTGGGAGGAGACACATGTCCC ⎦

TTTCCCGTCAGCAATGGGTTCAGCGCTCAGGATTTGCAG- ⎤
TTTCCCGTCAGCAATGGGTTCAGCGCTCAGGATTTGCAG- |  AY
TTTCCCGTCAGCAATGGGTTCAGCGCTCAGGATTTGCAG- |
TTTCCCGTCAGCAATGGGTTCAGCGCTCAGGATTTGCAG- ⎦
TTTCCCATCAGCAATGGGTTCAGCACTTAGGATATGCAG- ⎤
TTTCCCATCAGCAATGGGTTCAGCACTTAGGATATGCAG- |
TTTCCCATCAGCAATGGGTTCAGCACTTAGGATATGCAG- |
TTTCCCATCAGCAATGGGTTCAGCACTTAGGATATGCAG- |  ay
TTTCCCATCAGCAATGGGTTCAGCACTTAGGATATGCAG- |
TTTCCCATCAGCAATGGGTTCAGCACTTCGGATATGCAGG |
TTTCCCATCAGCAATGGGTTCAGCACTTAGGATATGCAG- |
TTTCCCATCAGCAATGGGTTCAGCACTTAGGATATGCAG- ⎦
```

Fig. 13

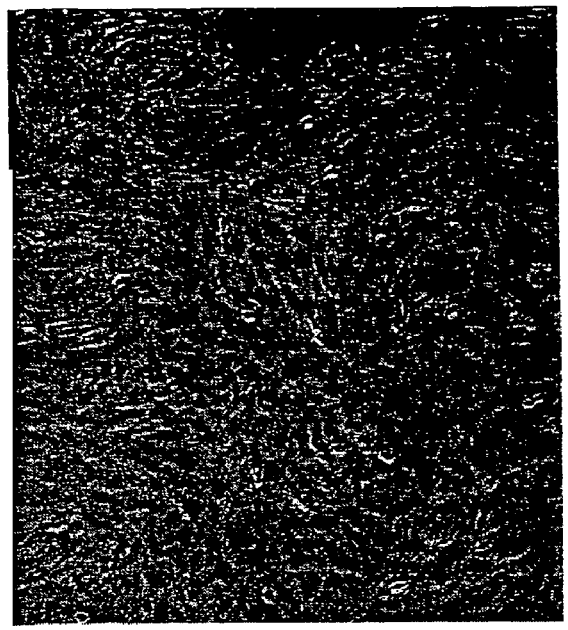
PRNP-/+IGHM-/-
Calf fibroblasts
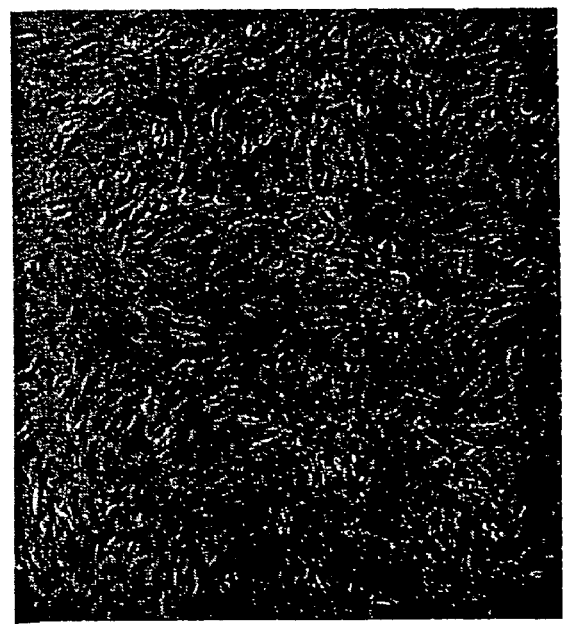
PRNP-/-IGHM-/-
Calf fibroblasts
Fig. 16A

SEQUENCE LISTING

<160> NUMBER OF SEQ ID NOS: 84

<210> SEQ ID NO 1
<211> LENGTH: 20
<212> TYPE: DNA
<213> ORGANISM: Bos taurus

```
<400> SEQUENCE: 1
tggtcactcc aagtgagtcg                                              20

<210> SEQ ID NO 2
<211> LENGTH: 21
<212> TYPE: DNA
<213> ORGANISM: Bos taurus

<400> SEQUENCE: 2
tggagtgaaa tcaggtgaag g                                            21

<210> SEQ ID NO 3
<211> LENGTH: 25
<212> TYPE: DNA
<213> ORGANISM: Bos taurus

<400> SEQUENCE: 3
gcaatagcaa gtccagcctc atctg                                        25

<210> SEQ ID NO 4
<211> LENGTH: 26
<212> TYPE: DNA
<213> ORGANISM: Bos taurus

<400> SEQUENCE: 4
catcctgtct ctggtggttt gaggtc                                       26

<210> SEQ ID NO 5
<211> LENGTH: 23
<212> TYPE: DNA
<213> ORGANISM: Bos taurus

<400> SEQUENCE: 5
gattgaatgg tctccaggat gcc                                          23

<210> SEQ ID NO 6
<211> LENGTH: 21
<212> TYPE: DNA
<213> ORGANISM: Bos taurus

<400> SEQUENCE: 6
gacaagctta atatccgcag g                                            21

<210> SEQ ID NO 7
<211> LENGTH: 25
<212> TYPE: DNA
<213> ORGANISM: Bos taurus

<400> SEQUENCE: 7
gagctgcaag aactcttcct cacgc                                        25

<210> SEQ ID NO 8
<211> LENGTH: 26
<212> TYPE: DNA
<213> ORGANISM: Bos taurus

<400> SEQUENCE: 8
atgtacctcc cagctgagac agaggg                                       26

<210> SEQ ID NO 9
<211> LENGTH: 28
<212> TYPE: DNA
<213> ORGANISM: Bos taurus
```

```
<400> SEQUENCE: 9
tttggtcctg tagtttgcta acacaccc                                         28

<210> SEQ ID NO 10
<211> LENGTH: 26
<212> TYPE: DNA
<213> ORGANISM: Bos taurus

<400> SEQUENCE: 10
ggatcagtgc ctatcactcc aggttg                                           26

<210> SEQ ID NO 11
<211> LENGTH: 20
<212> TYPE: DNA
<213> ORGANISM: Bos taurus

<400> SEQUENCE: 11
tggtcactcc aagtgagtcg                                                  20

<210> SEQ ID NO 12
<211> LENGTH: 21
<212> TYPE: DNA
<213> ORGANISM: Bos taurus

<400> SEQUENCE: 12
tggagtgaaa tcaggtgaag g                                                21

<210> SEQ ID NO 13
<211> LENGTH: 30
<212> TYPE: DNA
<213> ORGANISM: Bos taurus

<400> SEQUENCE: 13
tgtcaaagag acactcctca tttgtcttcc                                       30

<210> SEQ ID NO 14
<211> LENGTH: 25
<212> TYPE: DNA
<213> ORGANISM: Bos taurus

<400> SEQUENCE: 14
tcatagccga atagcctctc caccc                                            25

<210> SEQ ID NO 15
<211> LENGTH: 24
<212> TYPE: DNA
<213> ORGANISM: Bos taurus

<400> SEQUENCE: 15
ttgctccacc ttccgtcttc tgtc                                             24

<210> SEQ ID NO 16
<211> LENGTH: 25
<212> TYPE: DNA
<213> ORGANISM: Bos taurus

<400> SEQUENCE: 16
gttggcgcct accggtggat gtttg                                            25

<210> SEQ ID NO 17
<211> LENGTH: 20
<212> TYPE: DNA
```

<213> ORGANISM: Bos taurus

<400> SEQUENCE: 17
ccacataggc agttggatcc                                       20

<210> SEQ ID NO 18
<211> LENGTH: 20
<212> TYPE: DNA
<213> ORGANISM: Bos taurus

<400> SEQUENCE: 18
ataagaggcc tgctcatggc                                       20

<210> SEQ ID NO 19
<211> LENGTH: 25
<212> TYPE: DNA
<213> ORGANISM: Bos taurus

<400> SEQUENCE: 19
caatagcaag tccagcctca tctgc                                 25

<210> SEQ ID NO 20
<211> LENGTH: 24
<212> TYPE: DNA
<213> ORGANISM: Bos taurus

<400> SEQUENCE: 20
gtggtttctt cggtggaaac aacg                                  24

<210> SEQ ID NO 21
<211> LENGTH: 20
<212> TYPE: DNA
<213> ORGANISM: Bos taurus

<400> SEQUENCE: 21
tggtcactcc aagtgagtcg                                       20

<210> SEQ ID NO 22
<211> LENGTH: 21
<212> TYPE: DNA
<213> ORGANISM: Bos taurus

<400> SEQUENCE: 22
tggagtgaaa tcaggtgaag g                                     21

<210> SEQ ID NO 23
<211> LENGTH: 20
<212> TYPE: DNA
<213> ORGANISM: Bos taurus

<400> SEQUENCE: 23
caaaacctgg aggaggatgg                                       20

<210> SEQ ID NO 24
<211> LENGTH: 20
<212> TYPE: DNA
<213> ORGANISM: Bos taurus

<400> SEQUENCE: 24
ataagaggcc tgctcatggc                                       20

<210> SEQ ID NO 25
<211> LENGTH: 20

<210> SEQ ID NO 25
<211> LENGTH: 20
<212> TYPE: DNA
<213> ORGANISM: Bos taurus

<400> SEQUENCE: 25
acatccgcaa ggacctctac                                              20

<210> SEQ ID NO 26
<211> LENGTH: 20
<212> TYPE: DNA
<213> ORGANISM: Bos taurus

<400> SEQUENCE: 26
aaccgactgc tgtcaccttc                                              20

<210> SEQ ID NO 27
<211> LENGTH: 20
<212> TYPE: DNA
<213> ORGANISM: Bos taurus

<400> SEQUENCE: 27
tggtcactcc aagtgagtcg                                              20

<210> SEQ ID NO 28
<211> LENGTH: 21
<212> TYPE: DNA
<213> ORGANISM: Bos taurus

<400> SEQUENCE: 28
tggagtgaaa tcaggtgaag g                                            21

<210> SEQ ID NO 29
<211> LENGTH: 20
<212> TYPE: DNA
<213> ORGANISM: Bos taurus

<400> SEQUENCE: 29
tctctggtga cggcaatagc                                              20

<210> SEQ ID NO 30
<211> LENGTH: 20
<212> TYPE: DNA
<213> ORGANISM: Bos taurus

<400> SEQUENCE: 30
cttcgtgagg aagatgtcgg                                              20

<210> SEQ ID NO 31
<211> LENGTH: 20
<212> TYPE: DNA
<213> ORGANISM: Bos taurus

<400> SEQUENCE: 31
ccctcctctt tgtgctgtca                                              20

<210> SEQ ID NO 32
<211> LENGTH: 20
<212> TYPE: DNA
<213> ORGANISM: Bos taurus

<400> SEQUENCE: 32
gttcaggcca tcataggagg                                              20

<210> SEQ ID NO 33

```
<211> LENGTH: 20
<212> TYPE: DNA
<213> ORGANISM: Bos taurus

<400> SEQUENCE: 33
tctctggtga cggcaatagc                                              20

<210> SEQ ID NO 34
<211> LENGTH: 20
<212> TYPE: DNA
<213> ORGANISM: Bos taurus

<400> SEQUENCE: 34
cttcgtgagg aagatgtcgg                                              20

<210> SEQ ID NO 35
<211> LENGTH: 25
<212> TYPE: DNA
<213> ORGANISM: Bos taurus

<400> SEQUENCE: 35
ggctgactcc ctacctcccc tacac                                        25

<210> SEQ ID NO 36
<211> LENGTH: 20
<212> TYPE: DNA
<213> ORGANISM: Bos taurus

<400> SEQUENCE: 36
cggagcccct ggagatgagc                                              20

<210> SEQ ID NO 37
<211> LENGTH: 28
<212> TYPE: DNA
<213> ORGANISM: Bos taurus

<400> SEQUENCE: 37
ggtagtgcag tttcgaatgg acaaaagg                                     28

<210> SEQ ID NO 38
<211> LENGTH: 25
<212> TYPE: DNA
<213> ORGANISM: Bos taurus

<400> SEQUENCE: 38
tcaggatttg cagcacacag gagtg                                        25

<210> SEQ ID NO 39
<211> LENGTH: 26
<212> TYPE: DNA
<213> ORGANISM: Bos taurus

<400> SEQUENCE: 39
tggttggctt gtatggagca gcagac                                       26

<210> SEQ ID NO 40
<211> LENGTH: 27
<212> TYPE: DNA
<213> ORGANISM: Bos taurus

<400> SEQUENCE: 40
taggatatgc agcacacagg agtgtgg                                      27
```

-continued

<210> SEQ ID NO 41
<211> LENGTH: 20
<212> TYPE: DNA
<213> ORGANISM: Bos taurus

<400> SEQUENCE: 41
ccctcctctt tgtgctgtca                                              20

<210> SEQ ID NO 42
<211> LENGTH: 20
<212> TYPE: DNA
<213> ORGANISM: Bos taurus

<400> SEQUENCE: 42
gttcaggcca tcataggagg                                              20

<210> SEQ ID NO 43
<211> LENGTH: 30
<212> TYPE: DNA
<213> ORGANISM: Bos taurus

<400> SEQUENCE: 43
tgtcaaagag acactcctca tttgtcttcc                                   30

<210> SEQ ID NO 44
<211> LENGTH: 25
<212> TYPE: DNA
<213> ORGANISM: Bos taurus

<400> SEQUENCE: 44
tcatagccga atagcctctc caccc                                        25

<210> SEQ ID NO 45
<211> LENGTH: 24
<212> TYPE: DNA
<213> ORGANISM: Bos taurus

<400> SEQUENCE: 45
ttgctccacc ttccgtcttc tgtc                                         24

<210> SEQ ID NO 46
<211> LENGTH: 23
<212> TYPE: DNA
<213> ORGANISM: Bos taurus

<400> SEQUENCE: 46
gttggcgcct accggtggat gtg                                          23

<210> SEQ ID NO 47
<211> LENGTH: 20
<212> TYPE: DNA
<213> ORGANISM: Bos taurus

<400> SEQUENCE: 47
ccacataggc agttggatcc                                              20

<210> SEQ ID NO 48
<211> LENGTH: 20
<212> TYPE: DNA
<213> ORGANISM: Bos taurus

<400> SEQUENCE: 48
ataagaggcc tgctcatggc                                              20

```
<210> SEQ ID NO 49
<211> LENGTH: 20
<212> TYPE: DNA
<213> ORGANISM: Bos taurus

<400> SEQUENCE: 49
tggtcactcc aagtgagtcg                                               20

<210> SEQ ID NO 50
<211> LENGTH: 21
<212> TYPE: DNA
<213> ORGANISM: Bos taurus

<400> SEQUENCE: 50
tggagtgaaa tcaggtgaag g                                             21

<210> SEQ ID NO 51
<211> LENGTH: 20
<212> TYPE: DNA
<213> ORGANISM: Bos taurus

<400> SEQUENCE: 51
aagaagcgac caaaacctgg                                               20

<210> SEQ ID NO 52
<211> LENGTH: 21
<212> TYPE: DNA
<213> ORGANISM: Bos taurus

<400> SEQUENCE: 52
gtaacggtgc atgttttcac g                                             21

<210> SEQ ID NO 53
<211> LENGTH: 20
<212> TYPE: DNA
<213> ORGANISM: Bos taurus

<400> SEQUENCE: 53
acatccgcaa ggacctctac                                               20

<210> SEQ ID NO 54
<211> LENGTH: 20
<212> TYPE: DNA
<213> ORGANISM: Bos taurus

<400> SEQUENCE: 54
aaccgactgc tgtcaccttc                                               20

<210> SEQ ID NO 55
<211> LENGTH: 28
<212> TYPE: DNA
<213> ORGANISM: Bos taurus

<400> SEQUENCE: 55
ggtagtgcag tttcgaatgg acaaaagg                                      28

<210> SEQ ID NO 56
<211> LENGTH: 25
<212> TYPE: DNA
<213> ORGANISM: Bos taurus

<400> SEQUENCE: 56
tcaggatttg cagcacacag gagtg                                         25
```

```
<210> SEQ ID NO 57
<211> LENGTH: 26
<212> TYPE: DNA
<213> ORGANISM: Bos taurus

<400> SEQUENCE: 57
tggttggctt gtatggagca gcagac                                      26

<210> SEQ ID NO 58
<211> LENGTH: 27
<212> TYPE: DNA
<213> ORGANISM: Bos taurus

<400> SEQUENCE: 58
taggatatgc agcacacagg agtgtgg                                     27

<210> SEQ ID NO 59
<211> LENGTH: 20
<212> TYPE: DNA
<213> ORGANISM: Bos taurus

<400> SEQUENCE: 59
tctctggtga cggcaatagc                                             20

<210> SEQ ID NO 60
<211> LENGTH: 20
<212> TYPE: DNA
<213> ORGANISM: Bos taurus

<400> SEQUENCE: 60
cttcgtgagg aagatgtcgg                                             20

<210> SEQ ID NO 61
<211> LENGTH: 20
<212> TYPE: DNA
<213> ORGANISM: Bos taurus

<400> SEQUENCE: 61
ccacataggc agttggatcc                                             20

<210> SEQ ID NO 62
<211> LENGTH: 20
<212> TYPE: DNA
<213> ORGANISM: Bos taurus

<400> SEQUENCE: 62
ataagaggcc tgctcatggc                                             20

<210> SEQ ID NO 63
<211> LENGTH: 20
<212> TYPE: DNA
<213> ORGANISM: Bos taurus

<400> SEQUENCE: 63
aggccagcat ctgcgaggat                                             20

<210> SEQ ID NO 64
<211> LENGTH: 20
<212> TYPE: DNA
<213> ORGANISM: Bos taurus

<400> SEQUENCE: 64
```
gtggcagcaa gtagacatcg 20

<210> SEQ ID NO 65
<211> LENGTH: 23
<212> TYPE: DNA
<213> ORGANISM: Bos taurus

<400> SEQUENCE: 65
caggtgcagc tggtgcagtc tgg 23

<210> SEQ ID NO 66
<211> LENGTH: 23
<212> TYPE: DNA
<213> ORGANISM: Bos taurus

<400> SEQUENCE: 66
caggtcacct tgaaggagtc tgg 23

<210> SEQ ID NO 67
<211> LENGTH: 23
<212> TYPE: DNA
<213> ORGANISM: Bos taurus

<400> SEQUENCE: 67
gaggtgcagc tggtggagtc tgg 23

<210> SEQ ID NO 68
<211> LENGTH: 23
<212> TYPE: DNA
<213> ORGANISM: Bos taurus

<400> SEQUENCE: 68
caggtgcagc tgcaggagtc ggg 23

<210> SEQ ID NO 69
<211> LENGTH: 23
<212> TYPE: DNA
<213> ORGANISM: Bos taurus

<400> SEQUENCE: 69
gaggtgcagc tggtgcagtc tgg 23

<210> SEQ ID NO 70
<211> LENGTH: 23
<212> TYPE: DNA
<213> ORGANISM: Bos taurus

<400> SEQUENCE: 70
caggtacagc tgcagcagtc agg 23

<210> SEQ ID NO 71
<211> LENGTH: 23
<212> TYPE: DNA
<213> ORGANISM: Bos taurus

<400> SEQUENCE: 71
caggtgcagc tggtgcagtc tgg 23

<210> SEQ ID NO 72
<211> LENGTH: 25
<212> TYPE: DNA
<213> ORGANISM: Bos taurus

<400> SEQUENCE: 72

```
caccacgctg ctgagggagt agagt                                          25

<210> SEQ ID NO 73
<211> LENGTH: 20
<212> TYPE: DNA
<213> ORGANISM: Bos taurus

<400> SEQUENCE: 73
tcctctgagg agcttcaagc                                                20

<210> SEQ ID NO 74
<211> LENGTH: 20
<212> TYPE: DNA
<213> ORGANISM: Bos taurus

<400> SEQUENCE: 74
agggtttatt gagtgcaggg                                                20

<210> SEQ ID NO 75
<211> LENGTH: 4452
<212> TYPE: DNA
<213> ORGANISM: Bos taurus

<400> SEQUENCE: 75
gtcctggtca acagtgggct ggcctcagtg atctggttgt gctgaggact gggggcctga    60
gtgtgtatag tcttattgat gaccccagac ccccagagca ggcccaggt ggctgagctg    120 tgggcagtgg agggtgggct ggtagggctg agtgtgccct ccactccact gtcccagaga   180
gaaggtagag ctgcccacac ccccaaccag caggatgcct cacaccccc tcttctcctg    240 tgtcctctct cgggtcccca gaaggtgaat cacacccgaa agtcttcccc ctggtgtcct   300
gcgtgagctc gccatccgat gagagcacgg tggccctggg ctgcctggcc cgggacttcg   360
tgcccaattc agtcagcttc tcctggaagt tcaacaacag cacagtcagc agcgagagat   420
tctggacctt ccccgaagtc ctgagggacg gcttgtggtc ggcctcctct caggtggtcc   480
tgccctcctc aagcgccttt caaggccgg atgactacct ggtgtgcgaa gtccagcacc    540
ccaagggagg aaagaccgtc ggcaccgtga gggtgatcgc tacaagtgag tcgggcccgt   600
cccgtggttg ggtgcagggg agggtccagg ccccgctgac ctcttgtcct tctctgcaga   660
ggcggaagtg ctgtccccag tcgtgagtgt cttttgtccc g cctcgcaaca gcctctctgg   720
tgacggcaat agcaagtcca gcctcatctg ccaggccacg gacttcagcc ccaaacagat   780
ctcgttgtcc tggtttcgtg atggaaagcg atagtgtct ggaatttctg aaggccaggt   840
ggagactgtg cagtcctcac ccataacctt cagggcctac agcatgctga ccatcacgga   900
gagagactgg ctcagccaga acgcgtacac ctgccaggta aacacaaca aggaaacctt   960 ccagaagaac gtgtcctcct catgtgatgt tggtgagtgc agccctgggg ggcgggcgct  1020 cacctcagg tctgcagaca ccgccccaga cctgccagct gctccctgag ccttggcttc  1080
ccagagcggc aagggcagga ggggctgtgc agggcggctg ggggccggca ccctccaac   1140 agggccccag gttcacaggg gactcagcca agtgggccct ggtctttggg cggacctctc  1200
ccttcacctg atttcactcc aagcaactct ctcccacctc cagcaccacc atctccgatc  1260
ggggtcttca ccatccccc atccttcgcc gacatcttcc tcacgaagtc agccaagctg  1320
tcctgtctgg tcacaaacct ggcctccat gatggcctga acatcagctg gtcccgtcag   1380
aacgccaagg ccctggagac ccacacgtat tttgagcgac acctcaacga caccttcagc  1440
```

```
gcccggggtg aggcctcggt ctgctcggag gactgggagt ccggagagga gttcacgtgc    1500
acagtggccc actcggacct gcccttccca gaaaagaacg ccgtctccaa gcccaaaggt    1560
aggccctgcc ctgcccctgc cctccacccc agaccctccc ccggcttctg ccttctgagg    1620
acagcaggct agggccagca gaggtcccac actcgccgat ctcaccactg tgacccccte    1680 ccccacccag acgtcgccat gaaaccgccg tccgtgtacc tgctgcctcc aacgcgggaa    1740
cagctgagcc tgcgcgagtc ggcctccgtc acctgcctgg tgaaggcgtt cgcgcccgcg    1800
gacgtgttcg tgcagtggct gcagaggggg gagcccgtga ccaagagcaa gtacgtgacc    1860
agcgcccgcg cgcccgagcc ccaggacccc agcgtggtgt actttgtgca cagcatcctg    1920
acggtggccg aggaggactg gagcaaaggg gagacctaca cctgcgtcgt gcacgaagcc    1980
ctgcccacca tggtcaccga gcggaccgtg gacaagtcca ccggtaaacc caccctgtac    2040
aacgtgtccc tggtcctgtc tgacacagcc agcacctgct actgatgcct ggtcagagcc    2100 cccggggtgac cgtcgctgtg tgtgtgcatg agtgcagact aaccgtgtcg gtgcgcgaga    2160
tgctgcgttc tctaaaaatt agaaataaaa agatccattc aaagtgtggt tgtgagtgag    2220
caaagctctc cctgctaggc ccgtggctct ctgcctcacc ttgcaagaac cacctccatc    2280
atccgcaccc ccgcctcccc actcgcttcc aacccacgcg caggagccca gtgctccttg    2340
tgggatgctc acagcgggcc aagcccatgc tcgctgtgcc tcgagtcgct tccatggcca    2400
cactgggggc acacgggtgt gcaacacaca cacatgcaca gtcacataca tacatgcaga    2460
gagacacatg tgtgcacaca catgcatgga cacgcagaca gcacgcacat ggacagagac    2520
ctgggcacac gtgacacaga catgtatatg atggaatggg tgagcaggca cacacacatg    2580
gacacatgaa acatgtggac acacagacac acatgtacac gcgcactcac acgcaagtgc    2640
acacagtcac tcataggcac atgcacatgg gcactcacag acacacacgc atgaggacga    2700
gtcatacaca tgtagacaca cacgcacaga tgtacacacg ctcatgcaca catgaatgca    2760
ctgcacacat ccaggctcac acactcggat cccagcccct tggacaccccg tgctcactca    2820 gtgccctgtc tgggggggttc ctctgcacca tgcccgtgct ctgcttgtcc ctctgtctca    2880
gctgggaggt acatttggag gccgccccaa acccagcccc agaccagggt gcgcagcggg    2940
ccactctggg cctggccaga ggcagctcct caggaaactc atggcccctg tccaggaggg    3000
atgcttctcc cagtccaggc ccttgtgaag gtggcagggc cccagctctc cccttttccct    3060 gtgaagagac agagtcagtc gtgtcctgac agcgggccat gcctgggagg ccccccttgg    3120
agtatgcagc tgcagggcca cacgtcaacc tggagtgata ggcactgatc cgacgggcaa    3180
gcgggtctcc tctgccaccc acaccagtgc ccttcaggct gactccctac ctcccctaca    3240
ctcctggatc tttatggacc aagggcccat cagtgtagtg tctgcagaac taggtgactg    3300
tcctcagcct ttgtcccacg tcactctccc tgggtctcag atgtctatct gaactcctga    3360
tcccacagct gtgagtcctg cagttcaggc cccagcgagg ccccacaag gcctctctcg    3420 tacatgccat gtcttcaagg cagagagaga tggaggccag agggatgggc cccttggcac    3480
aggcagacat ctgcccccag ggcttgtgcc tcactggcta gggagccgac tcaaaccac    3540 cagagacagg acgccccacc accgctgtca gccccaagtg gccctgagtc ctccagaggg    3600
gtcgaggaca cctggccact cccccacctc cagcccagcg agaccccacc cttgtgtgta    3660
cgcgtgtgct ctgtctcgct ctgtgccacc ccggcgctcc tagggccagg cactcggggc    3720
cactgcttgg ctcagcctca gccacgctct gccctgcag gctgtggaat tgggcggcca    3780
ggggcctacc agtcctggct aagacgctgc ctgtcaagtc ctggagctcc caactgcccc    3840
```

```
gggggtgccg gggaggcagg cacacgcctg ctcgcctgcc cgctcgcttc tgaagtcccc    3900
caacccttct gatgggtcag ggcggccgag ggggccagg ccgggctctg cgggcagctc    3960
agccgtgtga ccaccgtgcc ctatctccca cagaggggga ggtgagcgcc gaggaagaag    4020
gctttgaaaa cctcaacacc atggcctcca ccttcatcgt gctcttcctc ctgagcctct    4080
tctacagcac cacggtcacc ctgttcaagg tagccgcatc gtcccgagga ggggtgagg     4140 ccacagagcc ccggggccgc agatgcccac gcacgcactc acgctgtctc tgtcgcctgc    4200
aggtgaagtg atggccagcc aagaacatgg ggcaccggag acggaacacg aggggctgcc    4260
ttggggccgg gtccctggcc tatgtggctt gtccgcttgt actgaaattt ccctgcgtc     4320 ctctccagct tcaagctgta agaaactggc ttttctcgga gcagctgagt gccatggcca    4380
agcatggagc ccgcagtaat aggctccacc tggccctgct ttgcaatgtc gcatttgtgg    4440
ccttgaaata aa                                                         4452

<210> SEQ ID NO 76
<211> LENGTH: 4485
<212> TYPE: DNA
<213> ORGANISM: Bos taurus

<400> SEQUENCE: 76
tctagatgga ctgagctgac cccactggac tgtcctggtc aacagtgggc tggcctcagt      60
gatctggttg tgctgaggac tgggggcctg agtgtgtatc agtcttattg atgaccccag     120 accccccagag caggccccag gtggctgagc tgtgggcagt gagggtgggc tggtagggct    180
gagtgtgccc tccactccac tgtcccagag agaaggtaga gctgcccaca cccccaacca    240
gcaggatgcc tcacaccccc ctcttctcct gtgtcctctc tcgggtcccc agaaggtgaa    300
tcgctcccga gagtcttccc cctggtgtcc tgcatgagct ccccatccga tgagagcacg    360
gtggccctgg gctgcctggc ccaggacttc atgcccaatt cagtcagctt ctcctggaag    420
ttcaacaaca gcacagtcgg cagcgagaga ttctggacct tccccgcagt cctgagggac    480
ggcttgtggt cggcctcctc tcaggtggtc ctgcctcct caagcgcctt tcaagggccg     540
gatgactacc tggtgtgcga agtccagcac cccaagggag aaagaccgt cggcaccgtg     600 agggtggtca ctccaagtga gtcgggcccg tccgtggtt gggtgcaggg gagggtccag    660
gccccgctga cctcttgtcc ttctctgcag aggcagaagt gctgtccccc atcgtgagtg    720
tctttgtccc gcctcgcaac agcctctctg gtgacggcaa tagcaagtcc agcctcatct    780
gccaggccac ggacttcagc cccaaacaga tctccttgtc ctggtttcgt gatggaaagc    840
ggatagtgtc tggcatttct gaaggccagg tggagactgt gcagtcctca cccataactt    900
tcagggccta cagcatgctg accatcacag agaaagactg gctcagccag aacgtgtaca    960
cctgccaggt agaacacaac aaggaaacct tccagaagaa cgtgtcctcc tcatgtaatg    1020
ttggtgagtg cagccctggg gggcgggcgc tcaccctcag gtctgcagac accgcccag    1080 acctgccagc tgctccctga gccttggctt cccagagcgg ccaagggcag gagggggctgt  1140 gcagggcggc tggggggccgg caccccctcca acagggcccc aggttcacag ggggactcagc  1200 caagtgggcc ctgctctttg gcggacctc tcccttcacc tgatttcact ccaagcaact   1260
ctctcccacc tccagcacca ccatctccca tcggggtctt caccatcccc ccatccttcg   1320
ccgacatctt cctcacgaag tcagccaagc tgtcctgtct ggtcacaaac ctggcctcct   1380
atgatggcct gaacatcagc tggtcccgtc agaacggcaa ggcccctgga acccacactt   1440
```

-continued

```
attttgggag acacctcaac gacaccttca gcgcccgggg tgaggcctcg gtctgctcgg    1500
aggactggga gtccggagag gagttcacgt gcacagtggc ccactcggac ctgcccttcc    1560
cagaaaagaa caccgtctcc aagcccaaag gtaggccctg ccctgcccct gcctccacc    1620
ccagaccctc ccccggcttc tgccttctga ggacagcagg cagggccagc agaggaccca    1680
cactcgccga tctcaccact gtgacccct cccccaccca gacgtcgcca tgaaaccgcc     1740
gtccgtgtac ctgctgcctc caacgcggga acagctgagc ctgcgggagt cggcctccgt    1800
cacctgcctg gtgaagggct tcgcgcccgc ggacgtgttc gtgcagtggc tgcagagggg    1860
ggagcccgtg accaagagca agtacgtgac cagcagcccg gcgcccgagc ccaggaccc    1920
cagcgtgtac tttgtgcaca gcatcctgac ggtggccgag gaggactgga gcaaagggga    1980
gacctacacc tgcgtcgtgg gccacgaggc cctgccccac atggtcaccg agcggaccgt    2040
ggacaagtcc accggtaaac ccaccctgta caacgtgtcc ctggtcctgt ctgacacagc    2100
cagcacctgc tactgatgcc tggtcagagc ccccgggtga ccgtcgctgt gtgtgtgcat    2160
gagtgcagac taaccgtgtc ggtgcgcgag atgctgcgtt ctctaaaaat tagaaataaa    2220
aagatccatt caaagctgct ggttgtgagt gagcaaagct ctccctgcta ggcccgtggc    2280
tgtctgccct caccttgcag accacctcca tcatccgcac ccccgcctcc ccactcgctt    2340
ccaacccacg cccaggagcc ccagtgctcc ttgtgggatg ctcacagcag gccaagccca    2400
tgctcgctgt gcctcgagtc gcttccatgg ccacactggg ggcacacggg tgtgcaacac    2460
acacacatgc acagtcacat acatacatgc agagagacac atgtgtgcac acacatgcat    2520
ggacacgcag acagcacgca catggacaga gacctgggca cacgtgacac agacatgtat    2580
atgatggaat gggtgagcag gcacacacac atggacacat gaaacatgtg gacacacaga    2640
cacacatgta cacgcgcact cacacgcaag tgcacacagt cactcatagg cacatgcaca    2700
tgggcactca cagacacaca cgcatgagga cgagtcatac acatgtagac acacacgcac    2760
agatgtacac acgctcatgc acacatgaat gcactgcaca catccaggct cacacactcg    2820
gatcccagcc cttggacacc ccgtgctcac tcagtgccct gtctgggggg ttcctctgca    2880
ccatgcccgt gctctgcttg tccctctgtc tcagctggga ggtacatttg gaggccgccc    2940
caaacccagc cccagaccag ggtgcgcagc gggccactct gggcctggcc agaggcagct    3000
cctcaggaaa ctcatggccc ctgtccagga gggatgcttc tcccagtcca ggcccttgtg    3060
aaggtggcag ggccccagct ctccccttc cctgtgaaga cacagagtca gtcgtgtcct    3120
gacagcgggc catgcctggg aggccccccct tggagtatga gctgcaggg ccacgtca     3180
acctggagtg ataggcactg atccgacggg caagcgggtc tcctctgcca cccacaccag    3240
tgcccttcag gctgactccc tacctcccct acactcctgg atctttatgg accaagggcc    3300
catcagtgta gtgtctgcag aactaggtga ctgtcctcag cctttgtccc acgtcactct    3360
ccctgggtct cagatgtcta tctgaactcc tgatcccaca gctgtgagtc ctgcagttca    3420
ggccccagcg agggccccac aaggcctctc tcgtacatgc catgtcttca aggcagagag    3480
agatggaggc cagagggatg ggccccttgg cacaggcaga catctgcccc cagggcttgt    3540
gcctcactgg ctagggagcc gacctcaaac caccagagac aggacgcccc accaccgctg    3600
tcagccccaa gtgccctga gtcctccaga ggggtcgagg acacctggcc actcccccac    3660
ctccagccca gcgagacccc accttgtgt gtacgcgtgt gctctgtctc gctctgtgcc    3720
accccggcgc tcctagggcc aggcactcgg ggcactgct ggctcagcc tcagccacgc     3780
tctgccccctg caggctgtgg aattgggcgg ccaggggcct accagtcctg gctaagacgc    3840
```

-continued

```
tgcctgtcaa gtcctggagc tcccaactgc cccgggggtg ccggggaggc aggcacacgc    3900
ctgctcgcct gcccgctcgc ttctgaagtc ccccaaccct tctgatgggt cagggcggcc    3960
gagggggggcc aggccgggct ctgcgggcag ctcagccgtg tgaccaccgt gccctatctc    4020
ccacagaggg ggaggtgagc gccgaggaag aaggctttga aaacctcaac accatggcct    4080
ccaccttcat cgtgctcttc ctcctgagcc tcttctacag caccacggtc accctgttca    4140
aggtagccgc atcgtcccga ggagggggtg aggccacaga gccccggggc cgcagatgcc    4200
cacgcacgca ctcacgctgt ctctgtcgcc tgcaggtgaa gtgatggcca gccaagaaca    4260
tggggcaccg gagacggaac acgaggggct gccttggggc cgggtccctg cctatgtgg    4320
cttgtccgct tgtactgaaa ttttccctgc gtcctctcca gcttcaagct gtaagaaact    4380
ggcttttctc ggagcagctg agtgccatgg ccaagcatgg agcccgcagt aataggctcc    4440
acctggccct gctttgcaat gtcgcatttg tggccttgaa ataaa              4485
```

<210> SEQ ID NO 77
<211> LENGTH: 1482
<212> TYPE: DNA
<213> ORGANISM: Bos taurus

<400> SEQUENCE: 77

```
gagagtcttc cccctggtgt cctgcgtgag ctcgccatcc gatgagagca cggtggccct      60
gggctgcctg gccgggact tcgtgcccaa ttcagtcagc ttctcctgga agttcaacaa     120
cagcacagtc agcagcgaga gattctggac cttccccgaa gtcctgaggg acggcttgtg     180
gtcggcctcc tctcaggtgg tcctgccctc ctcaagcgcc tttcaagggc cggatgacta     240
cctggtgtgc gaagtccagc accccaaggg aggaaagacc gtcggcaccg tgagggtgat     300
cgctacaaag gcggaagtgc tgtccccagt cgtgagtgtc tttgtcccgc ctcgcaacag     360
cctctctggt gacggcaata gcaagtccag cctcatctgc caggccacgg acttcagccc     420
caaacagatc tccttgtcct ggtttcgtga tggaaagcgg atagtgtctg gaatttctga     480
aggccaggtg gagactgtgc agtcctcacc cgtaactttc agggcctaca gcatgctgac     540
catcacggag agagactggc tcagccagaa cgtgtacacc tgccaggtag aacacaacaa     600
ggaaaccttc cagaagaacg tgtcctcctc atgtgatgtt gcaccaccat ctcccatcgg     660
ggtcttcacc atccccccat ccttcgccga catcttcctc acgaagtcag ccaagctgtc     720
ctgtctggtc acaaacctgg cctcctatga tggcctgaac atcagctggt cccgtcagaa     780
cggcaaggcc ctggagaccc acacgtattt tgagcgacac ctcaacgaca ccttcagcgc     840
ccgggggtgag gcctcggtct gctcggagga ctggagtcc ggagaggagt tcacgtgcac     900
agtggcccac tcggacctgc ccttcccaga aaagaacagc gtctccaagc caaagacgt     960
cgccatgaaa ccgccgtccg tgtacctgct gcctccaacg cgggaacagc tgagcctgcg    1020
ggagtcggcc tccgtcacct gcctggtgaa gggcttcgcg cccgcggacg tgttcgtgca    1080
gtggctgcag aggggggagc ccgtgaccaa gagcaagtac gtgaccagca gcccggcgcc    1140
cgagcctcag gaccccagcg tgtactttgt gcacagcatc ctgacggtgg ccgaggagga    1200
ctggagcaaa ggggagacct acacctgcgt cgtgggccac gaggccctgc cccacatggt    1260
caccgagcgg accgtggaca gtccaccgg taaacccacc ctgtacaacg tgtccctggt    1320
cctgtctgac acagccagca cctgctgctg atgcctggtc agagccccg ggtgaccgtc    1380
gctgtgtgtg catgagtgca gactaaccgt gtcggtgcgc gagatgctgc actctataaa    1440
```

```
aattagaaat aaaaagatcc attcaaaaaa aaaaaaaaaa aa                        1482
```

<210> SEQ ID NO 78
<211> LENGTH: 40
<212> TYPE: DNA
<213> ORGANISM: Bos taurus

<400> SEQUENCE: 78

```
ccgggaatgg cggcagagag gggcggggtg tccttggggc                            40
```

<210> SEQ ID NO 79
<211> LENGTH: 40
<212> TYPE: DNA
<213> ORGANISM: Bos taurus

<400> SEQUENCE: 79

```
ccgggaatgg cggcagagag gggtggggtg tcctcggggc                            40
```

<210> SEQ ID NO 80
<211> LENGTH: 40
<212> TYPE: DNA
<213> ORGANISM: Bos taurus

<400> SEQUENCE: 80

```
ccggcgtggc gccactggcc tgggaggaga cacacgtccc                            40
```

<210> SEQ ID NO 81
<211> LENGTH: 40
<212> TYPE: DNA
<213> ORGANISM: Bos taurus

<400> SEQUENCE: 81

```
ccggcgtggc gccactggcc tgggaggaga cacatgtccc                            40
```

<210> SEQ ID NO 82
<211> LENGTH: 39
<212> TYPE: DNA
<213> ORGANISM: Bos taurus

<400> SEQUENCE: 82

```
tttcccgtca gcaatgggtt cagcgctcag gatttgcag                             39
```

<210> SEQ ID NO 83
<211> LENGTH: 39
<212> TYPE: DNA
<213> ORGANISM: Bos taurus

<400> SEQUENCE: 83

```
tttcccatca gcaatgggtt cagcacttag gatatgcag                             39
```

<210> SEQ ID NO 84
<211> LENGTH: 40
<212> TYPE: DNA
<213> ORGANISM: Bos taurus

<400> SEQUENCE: 84

```
tttcccatca gcaatgggtt cagcacttcg gatatgcagg                            40
```

TRANSGENIC ANIMALS AND USES THEREOF

CROSS REFERENCE TO RELATED APPLICATIONS

This application claims benefit from U.S. Provisional Application Ser. No. 60/564,445 (filed Apr. 22, 2004), which is hereby incorporated by reference.

FIELD OF THE INVENTION

The present invention relates to the field of genetic engineering.

BACKGROUND OF THE INVENTION

Gene targeting by homologous recombination is a powerful means to specifically modify a gene of interest. The availability of embryonic stem (ES) cells has been instrumental in the study of gene function in mice. In non-murine mammalian species, the lack of ES cells has been circumvented by gene targeting in primary somatic cells, followed by nuclear transfer. In spite of advances in molecular biology techniques, gene targeting in primary cells remains a challenge given the low frequency of homologous recombination (McCreath et al. (2000) Nature 405:1066-1069), the short lifespan of primary cells, and limitations in methods allowing the selection of properly targeted cells. Currently, primary cell gene targeting and production of offspring has mainly been performed with transcriptionally active genes, which are associated with a higher frequency of homologous recombination relative to silent genes (Denning et al. (2001) Nat. Biotechnol. 19:559-562). Furthermore, the selection of correctly targeted cells may be accomplished by having the targeted gene promoter drive the expression of a selection marker, a process which is not applicable to silent genes (Denning et al., supra; Lai et al. (2002) Science 295:1089-1092; Yifan et al. (2002) Nat. Biotechnol. 20:251-255; Thomson, A. J., et al., (2003) Reprod. Suppl. 61:495-508).

To fully evaluate the consequences of a genetic modification, both alleles of a gene need to be disrupted. In mice, this is generally accomplished by back crossing from a hemizygous transgenic founder animal to produce a homozygous targeted inbred line. Breeding to homozygosity is extremely time consuming in the mouse and represents an even more severe impediment in species that have a long generation interval and that are negatively impacted by the consequences of inbreeding. In the pig, two innovative approaches have been used to circumvent this limitation and produce homozygous β(1,3)-galactocyltransferase knockout animals. Hemizygous targeted primary cells were selected in vitro for the lack of the enzymatic activity resulting either from a spontaneous point mutation in the second allele of the gene (Denning et al., (2003) Reproduction 126:1-11) or for mitotic recombinants (Piedrahita (2000) Theriogenology 53: 105-16) and cloned offspring were made from the homozygous knockout cell lines. Unfortunately, these approaches are not generally useful for silent genes nor widely applicable for active genes. Thus, improved methods to study gene function in non-human mammals are desirable.

Antibody Production in Genetically Modified Animals

In 1890, Shibasaburo Kitazato and Emil Behring reported an experiment with extraordinary results; particularly, they demonstrated that immunity can be transferred from one animal to another by taking serum from an immune animal and injecting it into a non-immune one. This landmark experiment laid the foundation for the introduction of passive immunization into clinical practice. Today, the preparation and use of human immunoglobulin for passive immunization is standard medical practice. In the United States alone, there is a $1.4B per annum market for human immunoglobulin, and each year more than 16 metric tons of human antibody is used for intravenous antibody therapy. Comparable levels of consumption exist in the economies of most highly industrialized countries, and the demand can be expected to grow rapidly in developing countries. Currently, human antibody for passive immunization is obtained from the pooled serum of human donors. This means that there is an inherent limitation in the amount of human antibody available for therapeutic and prophylactic usage. Already, the demand exceeds the supply and severe shortfalls in availability have been routine.

In an effort to overcome some of the problems associated with the inadequate supply of human immunoglobulin, various technologies have been developed. For example, the production of human immunoglobulin by recombinant methods in tissue culture is routine. Particularly, the recombinant expression of human immunoglobulin in CHO expression systems is well known, and is currently utilized for the production of several human immunoglobulins and chimeric antibodies now in therapeutic use.

Mice retaining an unrearranged human immunoglobulin gene have also been developed for the production of human antibodies (e.g., monoclonal antibodies) (see, for example, PCT Publication Nos. WO98/24893; WO96/33735; WO 97/13852; WO98/24884; WO97/07671; and U.S. Pat. Nos. 5,877,397; 5,874,299; 5,814,318; 5,789,650; 5,770,429; 5,661,016; 5,633,425; 5,625,126; 5,569,825; and 5,545,806).

PCT Publication No. WO00/10383 describes modifying a human chromosome fragment and transferring the fragment into certain cells via microcell fusion. U.S. Pat. Nos. 5,849, 992 and 5,827,690 describe the production of monoclonal antibodies in the milk of transgenic animals including mice, sheep, pigs, cows, and goats wherein the transgenic animals expressed human immunoglobulin genes under the control of promoters that provide for the expression of the antibodies in mammary epithelial cells. Essentially, this results in the expression of the antibodies in the milk of such animals, for example a cow. U.S. Patent Publication Nos. 2003-0037347-0 describe the expression of xenogenous human immunoglobulins in cloned, transgenic ungulates.

Notwithstanding the foregoing, further improved methods for producing ungulates that are amenable to being used as hosts for xenogenous antibody production are of great value to this industry.

Production of Prion Protein-deficient Bovines

The cellular prion protein $PrP^C$ is a ubiquitously expressed, plasma membrane, glycosylphosphatidylinositol-anchored glycoprotein. This protein plays a crucial role in the pathogenesis of transmittable spongiform encephalopathies such as BSE, in cattle, and Creutzfeldt-Jakob disease (CJD), in humans. Its disease-associated, protease-resistant isoform, $PrP^{Sc}$, has the ability to convert normal $PrP^C$ to $PrP^{Sc}$ and is considered essential for the pathogenesis and transmittance of spongiform encephalopathies. Although the accumulation of $PrP^{Sc}$ in neurons is associated with fatal neurodegeneration, the normal physiological function of the protein remains unclear. Mice with disruptions restricted to the coding region of the PrP gene have been generated and show only minor phenotypic deficits. Importantly, they are resistant to infection by $PrP^{Sc}$, suggesting that $PrP^C$ is necessary for pathogenesis of prion diseases (Prusiner et al. (1993) Proc. Natl. Acad. Sci. USA 90:10608-10612; Weissmann et al. (1994) Ann. NY Acad. Sci. 724:235-240).

BSE was first recognized in 1986 in the United Kingdom and now has been spread to many countries throughout the world. BSE can be transmitted from cattle to humans by direct consumption of contaminated beef products, resulting in a variant form of CJD (vCJD). Currently, there is no cure for the fatal disease. To reduce risk of exposure to the disease-causing PrP$^{Sc}$ protein, expensive testing programs have been implemented and efforts to remove bovine components from a wide variety of products have been initiated in many countries. Cattle with homozygous null mutation in the PrP gene alleles could be used to alleviate concerns about BSE-contaminated bovine products. Furthermore, these animals could be useful as a model, in addition to the mouse, for investigating the involvement of PrP in BSE.

SUMMARY OF THE INVENTION

In general, the invention features genetically modified non-human mammals (e.g., bovines and other ungulates), and methods of making these mammals. In particular, the invention features transgenic ungulates having reduced levels of endogenous IgM heavy chain and/or prion protein.

Transgenic Ungulates having Reduced IgM Heavy Chain Protein

We discovered that bovines have two IgM heavy chain-encoding genes, each of which is expressed and undergoes VDJ rearrangement. Additionally, we have used homologous recombination to disrupt each of these genes in bovine fibroblasts, which can then be used in cloning methods to make transgenic bovines in which functional IgM is reduced, substantially eliminated, or eliminated.

Although only one IgM-encoding gene has been identified in other ungulates, it is likely, in view of our discovery, that additional such genes are present.

The transgenic ungulates of the invention are useful, for example, for the production of xenogeneic immunoglobulins and xenogeneic hematopoietic stem cells, and for the maintenance of xenogeneic tissues and organs in vivo.

Accordingly, the invention features a transgenic ungulate that is producing less than 10% of endogenous IgM heavy chain, relative to a control ungulate, and whose genome comprises a mutation of a gene encoding IgM heavy chain (e.g., bovine IgμU or bovine IgμAY). Desirably, the ungulate is producing less than 5%, 2%, or even 1%, relative to a matching control ungulate. Most desirably, the ungulate is producing no IgM heavy chain or IgM at levels below detection by western blot.

In one embodiment, the ungulate is a transgenic ungulate ungulate whose genome comprises a mutation in each of two genes encoding IgM heavy chain. Desirably, at least one mutation is a homozygous mutation, and more desirably both mutations are homozygous mutations. The mutation may be an insertion, deletion, or substitution, but most desirably is achieved by insertion of an exogenous nucleic acid, e.g., by homologous recombination. While the ungulate may still make some functional IgM heavy chain, it is most desirable that all functional IgM heavy chain is lost as a result of the mutations.

The invention is exemplified in a bovine, but is equally applicable to other ungulates (e.g., ovines, porcines, and caprines). In the case of bovines, the two IgM-encoding genes are IgμU and IgμAY.

The ungulate may be an adult ungulate, a fetal ungulate, or an ungulate embryo.

The invention also features (i) a transgenic ungulate somatic cell whose genome comprises a mutation of two genes encoding IgM heavy chain, as described above, and (ii) a transgenic bovine somatic cell whose genome comprises a hemizygous or homozygous mutation of IgμAY. Suitable cells include fibroblasts, epithelial cells, endothelial cells, neural cells, keratinocytes, hematopoietic cells, melanocytes, chondrocytes, lymphocytes (B-cells and T-cells), macrophages, monocytes, mononuclear cells, cardiac muscle cells, other muscle cells, and epidermal cells.

The invention further features methods for making xenogenous antibodies. One such method includes the steps of: (a) providing a transgenic ungulate of the invention, the ungulate having engrafted xenogenous hematopoietic stem cells; and (b) recovering xenogenous antibodies from this ungulate (e.g., from the serum or milk).

Another method for producing xenogenous antibodies includes the steps of: (a) providing a transgenic ungulate of the invention, the ungulate having a nucleic acid encoding all or part of a xenogenous immunoglobulin gene that undergoes rearrangement and expresses a xenogenous immunoglobulin; (b) administering one or more antigens of interest to the ungulate; and (c) recovering xenogenous antibodies from the ungulate.

The invention also features a method of expanding xenogenous hematopoietic stem cells by (a) providing a transgenic ungulate of the invention and having engrafted xenogenous hematopoietic stem cells; and (b) allowing the xenogenous hematopoietic stem cells to expand in said transgenic ungulate. If desired, the expanded hematopoietic stem cells can be collected from the transgenic ungulate.

The invention also features a method for maintaining a desired tissue or organ in vivo by: (a) providing a transgenic ungulate of the invention; (b) engrafting desired allogeneic or xenogeneic tissue or organ (e.g., skin, heart, lung, pancreatic, liver or kidney tissue) into the ungulate; and (c) maintaining the tissue or organ in the animal.

In any of the foregoing aspects of the invention, a transgenic ungulate may optionally have one or more nucleic acids encoding all or part of a xenogenous immunoglobulin gene that undergoes rearrangement and expresses one or more xenogenous immunoglobulins. In a preferred embodiment, the nucleic acid encoding all or part of a xenogenous gene is substantially human. Preferably, the nucleic acid encodes a xenogenous antibody, such as a human antibody or a polyclonal antibody. In various embodiments, the immunoglobulin chain or antibody is expressed in serum and/or milk. In other embodiments, the nucleic acid is contained within a chromosome fragment, such as a ΔHAC(FERM BP-7582, the International Patent Organism Depository, National Institute of Advanced Industrial Science and Technology, Tsukuba Central 6, 1-1, Higashi 1-Chome Tsukuba-shi, Ibaraki-ken, 305-8566, Japan) or a ΔΔHAC (FERM BP-7581). In yet other embodiments, the nucleic acid is maintained in an ungulate cell independently from the host chromosome.

In still other embodiments of any of the aspects of the invention, the ungulate has a mutation of one or both alleles of an endogenous alpha-(1,3)-galactosyltransferase gene, PrP gene, and/or J chain gene. In other preferred embodiments, the ungulate has a nucleic acid encoding an exogenous J chain, such as a human J chain. Preferably, the mutation reduces or eliminates the expression of the endogenous alpha-(1,3)-galactosyltransferase enzyme, galactosyl(α1,3) galactose epitope, prion protein, and/or J chain. In still other preferred embodiments, the ungulate contains a xenogenous J chain nucleic acid, such as a human J chain nucleic acid. Preferably, the ungulate produces human IgA or IgM molecules containing human J chain. In various embodiments of the invention, the nucleic acid used to mutate an endogenous ungulate nucleic acid (e.g., a knockout cassette which includes a promoter operably linked to a nucleic acid encoding a selectable marker and operably linked to a nucleic acid having substantial sequence identity to the gene to be mutated) is not contained in a viral vector, such as an adenoviral vector or an adeno-associated viral vector. For example, the nucleic acid may be contained in a plasmid or artificial chromosome that is inserted into an ungulate cell, using a standard method such as transfection or lipofection that does not involve viral infection of the cell. In yet another embodiment, the nucleic acid used to mutate an endogenous ungulate nucleic acid (e.g., a knockout cassette which includes a promoter operably linked to a nucleic acid encoding a selectable marker and operably linked to a nucleic acid having substantial sequence identity to the gene to be mutated) is contained in a viral vector, such as an adenoviral vector or an adeno-associated viral vector. According to this embodiment, a virus containing the viral vector is used to infect an ungulate cell, resulting in the insertion of a portion or the entire viral vector into the ungulate cell.

Preferably, the ungulate is a bovine, ovine, porcine, or caprine. Preferably, the transgenic ungulate expresses an immunoglobulin chain or antibody from another genus, such as an antibody from any other mammal. Particularly preferred ungulates are sheep, big-horn sheep, goats, buffalos, antelopes, oxen, horses, donkeys, mule, deer, elk, caribou, water buffalo, camels, llama, alpaca, pigs, and elephants.

The invention also features a method of producing a transgenic ungulate (for example, a transgenic bovine) that rearranges and expresses a xenogenous (e.g., human) immunoglobulin gene locus. This may be accomplished, for example, by stably introducing a human chromosome fragment containing immunoglobulin genes into the ungulate, in order to produce a transgenic ungulate having B-cells that produce xenogenous immunoglobulins, in addition to or in lieu of endogenous immunoglobulins. This may also be accomplished by integrating a nucleic acid encoding a xenogenous immunoglobulin chain or xenogenous antibody into a chromosome of an ungulate. The transgenic ungulate has a mutation in at least two genes encoding IgM, such that the expression of endogenous IgM has been reduced or eliminated. In one embodiment, the invention features a method of producing a transgenic ungulate (for example, a transgenic bovine) in which at least two mu constant regions have been disrupted, and an artificial chromosome containing a gene locus encoding another species' immunoglobulin, preferably human, has been stably incorporated.

The invention also features a method of producing an ungulate somatic or embryonic stem (ES) cell, preferably a fibroblast or B-cell, wherein one or both alleles of at least two the endogenous IgM heavy chain genes have been disrupted, for example, by homologous recombination.

The invention also features a method of inserting, into an ungulate in which at least two the endogenous IgM heavy chain genes have been disrupted, a nucleic acid (for example, an artificial chromosome) that contains genes sufficient for the functional expression of non-ungulate immunoglobulins or their heavy or light chains. Preferably, these immunoglobulins are human immunoglobulins produced by introduction of nucleic acid encoding these immunoglobulins or immunoglobulin chains into an ungulate somatic cell, preferably a fibroblast, and producing cloned ungulates in which the nucleic acid is transmitted into the germ line.

The invention also features a method for introducing an artificial chromosome, preferably a human artificial chromosome (HAC), that contains genes that provide for immunoglobulin expression into the aforementioned homozygous knockout cells and generate ungulates that express non-ungulate immunoglobulins, preferably human immunoglobulins, in response to immunization and which undergo affinity maturation.

The invention also features methods for producing hybridomas and monoclonal antibodies using B-cells derived from the above-described transgenic ungulates (for example, transgenic bovines).

The invention also features methods for producing ungulate antiserum or milk that includes polyclonal human immunoglobulin by providing a transgenic ungulate described above that is producing polyclonal human immunoglobulins, and collecting ungulate antiserum or milk from the ungulate. Such human immunoglobulin, preferably human IgG, may be used as intravenenous immunoglobulin (IVIG) for the treatment or prevention of disease in humans. The polyclonal human immunoglobulins are preferably reactive against an antigen of interest.

Transgenic Ungulates having Reduced Prion Protein

The present invention also features a bovine or bovine fetus that includes a non-naturally occurring mutation in one or both alleles of an endogenous prion nucleic acid. The mutation reduces, substantially eliminates, or eliminates the expression of functional prion protein, and may be hemizygous or homozygous. In addition, the bovine or bovine fetus may carry a further mutation that reduces the expression of an endogenous antibody. This mutation, for example, may reduce or substantially eliminate the expression of functional IgM heavy chain. Preferably, the bovine fetus is at least 30 days post-fertilization but may be any age up to birth. Preferred bovines include newborns and calves that are at least 1 week of age, and, more preferably, at least 2 months of age.

In a related aspect, the invention further features a product produced from a bovine or bovine fetus of the invention and a method of producing a product that substantially lacks prion protein, the method involving manufacturing the product in, or obtaining the product from, a bovine or bovine fetus of the invention. Exemplary products include milk, gelatin, collagen, and serum obtained from the bovine or bovine fetus, as well as a recombinant protein produced in the bovine or bovine fetus.

Methods for Producing Non-human Mammals and Cells Containing Multiallelic or Multigenic Mutations The invention provides a method of producing a cell having two genetic modifications (e.g., mutations or insertions of transgenes or artificial chromosomes). The method includes the steps of: (a) providing a non-human mammalian somatic cell having a first genetic modification; (b) inserting the cell or a progeny thereof, a chromatin mass from said cell or progeny thereof, or a nucleus from the cell or progeny thereof into a nucleated or enucleated oocyte; (c) transferring the oocyte obtained from step (b) or an embryo formed from the oocyte into a recipient; (d) isolating a cell from the embryo, or from a fetus or juvenile produced therefrom, wherein the cell contains the first genetic modification; and (e) introducing a second genetic modification into the genome of the cell of step (d) or a progeny thereof, thereby producing a cell having two genetic modifications.

The present invention thus provides methods for producing non-human mammals and cells containing multiallelic or multigenic mutations. Examples of such mammals are ungulates (e.g., bovines, ovines, porcines, caprines, equines, or buffaloes), rabbits, mice, rats, or primates (e.g., monkeys, baboons, or gorillas). Using the rejuvenation techniques provided herein, the lifespan of cells is increased, thereby allowing the genetic manipulation of cells on a long-term basis.

In one aspect, the present invention provides for producing a bovine cell containing multiallelic or multigenic mutations, involving the steps of: (a) providing a somatic ungulate cell having a mutation in a first allele of an endogenous gene; (b) inserting the cell or a progeny thereof, a chromatin mass from the cell or a progeny thereof, or a nucleus from the cell or a progeny thereof into a nucleated or enucleated oocyte; (c) transferring the oocyte obtained from step (b) or an embryo formed from this oocyte into the oviduct or uterus of a bovine; (d) allowing the transferred oocyte or the embryo of step (c) to develop into a fetus; (e) isolating a fetal cell from the bovine at between 25 and 90 days of gestation; and (f) introducing a mutation into the second allele of the first endogenous gene or into an allele of a different, second endogenous gene, thereby producing a bovine cell containing multiallelic or multigenic mutations. If desired, the method of the invention further involves, beginning with the cell obtained in step (f) or a progeny thereof, repeating the above method one or more times, thereby introducing mutations in additional alleles or genes.

The invention further provides a method for producing a non-human mammal (e.g., an ungulate) containing two genetic modifications, involving the steps of: (a) providing a non-human mammalian cell containing multiallelic or multigenic mutations (e.g., any one of the cells obtained above); (b) inserting the cell or a progeny thereof, a chromatin mass from the cell or a progeny thereof, or a nucleus from the cell or a progeny thereof into a nucleated or enucleated oocyte; (c) transferring the oocyte obtained from step (b) or an embryo formed from this oocyte into a non-human mammal; (d) allowing the transferred oocyte or the embryo of step (c) to develop into a non-human mammal, thereby producing a non-human mammal containing two genetic modifications. If desired, prior to step (b), the cell provided in step (a) may be permeabilized under conditions that allow chromatin condensation.

Exemplary non-human mammals of the invention are ungulates (e.g., bovines, ovines, porcines, caprines, equines, or buffalos), primates (e.g., monkeys, baboons, or gorillas), rabbits, mice, and rats. Desirably, a bovine (e.g., *Bos taurus* or *Bos indicus*) containing two genetic odifications is produced using the cloning methods described herein.

In all foregoing aspects of the invention, any somatic cell may be used (e.g., a cell from an embryo, fetus, calf, or adult). Exemplary cells include fibroblasts, epithelial cells, neural cells, epidermal cells, keratinocytes, hematopoietic cells, melanocytes, chondrocytes, B-lymphocytes, T-lymphocytes, erythrocytes, macrophages, monocytes, placental cells, and muscle cells. If the non-human mammal is a bovine, desirably, somatic cells are isolated from a fetus at between 25 to 90 days of gestation, between 35 to 60 days of gestation, between 35 and 50 days, between 35 and 45 days, between 38 and 43 days, and most preferably at about 40 days of gestation. Optionally, somatic cells may be permeabilized as described herein prior to the their insertion into oocytes.

One type of genetic modification is a mutation. Mutations may be introduced into transcriptionally active genes or transcriptionally silent genes. Exemplary endogenous genes in which mutations may be introduced are antibody-encoding genes (e.g., J chain or Igμgenes such as IgμU or IgμAY), genes encoding α-(1,3)-galactosyltransferase, or prion genes.

Typically, a mutation is introduced by the insertion of a polynucleotide (e.g., positive selection marker such as an antibiotic resistance gene) into an endogenous gene. Optionally, a mutation that is introduced in an endogenous gene reduces the expression of this gene. Alternatively, a mutation may also include the insertion of xenogenous nucleic acid molecule encoding for a polypeptide, such as an antibody. If desired, the polynucleotide may also contain recombinase sites flanking the positive selection marker, such as loxP sites, so that the positive selection marker may be removed by a recombinase (e.g., Cre recombinase).

Another type of genetic modification is a transgene that has been inserted into the cell's genome without introducing a mutation. One desirable transgene is an artificial chromosome such as a human artificial chromosome. The use of artificial chromosomes for producing xenogenous antibody (e.g., human antibody) is described herein.

As used herein, by "allele" is meant one member of a DNA pair that occupies a specific position on a specific chromosome.

By "artificial chromosome" is meant a mammalian chromosome or fragment thereof which has an artificial modification such as the addition of a selectable marker, the addition of a cloning site, the deletion of one or more nucleotides, the substitution of one or more nucleotides, and the like. By "human artificial chromosome (HAC)" is meant an artificial chromosome generated from one or more human chromosome(s). An artificial chromosome can be maintained in the host cell independently from the endogenous chromosomes of the host cell. In this case, the HAC can stably replicate and segregate along side endogenous chromosomes. Alternatively, it may be translocated to, or inserted into, an endogenous chromosome of the host cell. Two or more artificial chromosomes can be introduced to the host cell simultaneously or sequentially. For example, artificial chromosomes derived from human chromosome #14 (comprising the Ig heavy chain gene), human chromosome #2 (comprising the Ig kappa chain gene), and human chromosome #22 (comprising the Ig lambda chain gene) can be introduced. Alternatively, an artificial chromosome(s) comprising both a xenogenous Ig heavy chain gene and Ig light chain gene, such as ΔHAC, ΔΔHAC, or κHAC may be introduced. Preferably, the heavy chain loci and the light chain loci are on different chromosome arms (i.e., on different side of the centromere). In still other preferred embodiments, the total size of the HAC is less than or equal to approximately 12, 10, 9, 8, or 7 megabases.

By a "bovine fetus" is meant a bovine in utero that is at least 30 days post-fertilization.

By "cells derived from an embryo" is meant cells that result from the cell division of cells in the embryo.

By "chimeric embryo" is meant an embryo formed from cells from two or more embryos. The resulting fetus or offspring can have cells that are derived from only one of the initial embryos or cells derived from more than one of the initial embryos. If desired, the percentage of cells from each embryo that are incorporated into the placental tissue and into the fetal tissue can be determined using standard FISH analysis or analysis of a membrane dye added to one embryo.

By "chimeric ungulate" is meant an ungulate formed from cells from two or more embryos. The ungulate can have cells that are derived from only one of the initial embryos or cells derived from more than one of the initial embryos. If desired, the percentage of cells from each embryo that are incorporated into the placental tissue and into the fetal tissue can be determined using standard FISH analysis or analysis of a membrane dye added to one embryo.

By "chromatin mass" is meant more than one chromosome not enclosed by a membrane. Preferably, the chromatin mass contains all of the chromosomes of a cell. An artificially induced chromatin mass containing condensed chromosomes may be formed by exposure of a nucleus to a mitotic reprogramming media (e.g., a mitotic extract) as described herein. Alternatively, an artificially induced chromatin mass containing decondensed or partially condensed chromosomes may be generated by exposure of a nucleus to one of the following, as described herein: a mitotic extract containing an anti-NuMA antibody, a detergent and/or salt solution, or a protein kinase solution. A chromatin mass may contain discrete chromosomes that are not physically touching each other or may contain two or more chromosomes that are in physical contact.

If desired, the level of chromosome condensation may be determined using standard methods by measuring the intensity of staining with the DNA stain, DAPI. As chromosomes condense, this staining intensity increases. Thus, the staining intensity of the chromosomes may be compared to the staining intensity for decondensed chromosomes in interphase (designated 0% condensed) and maximally condensed chromosomes in mitosis (designated 100% condensed). Based on this comparison, the percent of maximal condensation may be determined. Preferred condensed chromatin masses are at least 20, 30, 40, 50, 60, 70, 80, 90, or 100% condensed. Preferred decondensed or partially condensed chromatin masses are less than 10% condensed.

By "days of gestation" is meant the days from the time that the oocyte or embryo is transferred into a uterus.

By "donor cell" is meant a cell from which a nucleus or chromatin mass is derived, or a permeabilized cell.

By "embryo" or "embryonic" is meant a developing cell mass that has not implanted into the uterine membrane of a maternal host. Hence, the term "embryo" may refer to a fertilized oocyte; an oocyte containing a donor chromatin mass, nucleus, or reprogrammed cell; a pre-blastocyst stage developing cell mass; or any other developing cell mass that is at a stage of development prior to implantation into the uterine membrane of a maternal host and prior to formation of a genital ridge. An embryo may represent multiple stages of cell development. For example, a one cell embryo can be referred to as a zygote; a solid spherical mass of cells resulting from a cleaved embryo can be referred to as a morula, and an embryo having a blastocoel can be referred to as a blastocyst. An "embryonic cell" is a cell isolated from or contained in an embryo.

By "embryo cloning" is meant the process in which an embryo is produced from a cell or cellular materials from another animal. Embryo cloning may be performed, for example, by inserting or fusing a donor cell, nucleus, or chromatin mass with an oocyte. The resulting oocyte or the embryo formed from this oocyte is then transferred into the uterus of an animal, thereby producing a cloned animal.

By "enrichment or depletion of a factor" is meant the addition or removal of a naturally-occurring or recombinant factor by at least 20, 40, 60, 80, or 100% of the amount of the factor originally present in a reprogramming media (e.g., a cell extract). Alternatively, a naturally-occurring or recombinant factor that is not naturally present in the reprogramming media may be added. Preferred factors include proteins such as DNA methyltransferases, histone deacetylases, histones, protamines, nuclear lamins, transcription factors, activators, and repressors; membrane vesicles, and organelles. In one preferred embodiment, the factor is purified prior to being added to the reprogramming media, as described below. Alternatively, one of the purification methods described below may be used to remove an undesired factor from the reprogramming media.

By "fetus" is meant a developing cell mass that has implanted into the uterine membrane of a maternal host. A "fetal cell" is any cell isolated from or contained in a fetus at any stage of gestation including birth.

By "fragment" is meant a polypeptide having a region of consecutive amino acids that is identical to the corresponding region of an antibody of the invention but is less than the full-length sequence. The fragment has the ability to bind the same antigen as the corresponding antibody based on standard assays, such as those described herein. Preferably, the binding of the fragment to the antigen is at least 20, 40, 60, 80, or 90% of that of the corresponding antibody.

By "gene" is meant a hereditary unit consisting of a sequence of DNA that occupies a specific location on a chromosome and determines a particular characteristic in an organism. A gene typically has two alleles.

By "hemizygous mutation" is meant that one allele of an endogenous gene has been mutated and the other allele has not been mutated.

By "homozygous mutation" is meant that two alleles of an endogenous gene have been mutated. According to this invention, the mutation-introducing event at both alleles may or may not be the same. Accordingly, two alleles of an endogenous gene genetically targeted by two different targeting vectors would be considered a homozygous mutation.

By "homozygous knock-out non-human mammal" is meant a mammal other than a human in which the two alleles of an endogenous gene have been genetically targeted, resulting in the marked reduction or elimination of expression of a functional gene product. According to this invention, the genetic targeting event at both alleles may or may not be the same. Accordingly, a non-human mammal, in which the two alleles of an endogenous gene have been genetically targeted by two different targeting vectors resulting in the null expression of the endogenous gene, would be considered as being a homozygous knock-out non-human mammal.

By "immortalized" is meant capable of undergoing at least 25, 50, 75, 90, or 95% more cell divisions than a naturally-occurring control cell of the same cell type, genus, and species as the immortalized cell or than the donor cell from which the immortalized cell was derived. Preferably, an immortalized cell is capable of undergoing at least 2-, 5-, 10-, or 20-fold more cell divisions than the control cell. More preferably, the immortalized cell is capable of undergoing an unlimited number of cell divisions. Immortalized cells include cells that naturally acquire a mutation in vivo or in vitro that alters their normal growth-regulating process. Still other preferred immortalized cells include cells that have been genetically modified to express an oncogene, such as ras, myc, abl, bcl2, or neu, or that have been infected with a transforming DNA or RNA virus, such as Epstein Barr virus or SV40 virus (Kumar et al. (1999) Immunol. Lett. 65:153-159; Knight et al. (1988) Proc. Natl. Acad. Sci. USA 85:3130-3134; Shammah et al. (1993) J. Immunol. Methods 160:19-25; Gustafsson and Hinkula (1994) Hum. Antibodies Hybridomas 5:98-104; Kataoka et al. (1997) Differentiation 62:201-211; Chatelut et al. (1998) Scand. J. Immunol. 48:659-666). Cells can also be genetically modified to express the telomerase gene (Roques et al. (2001) Cancer Res. 61:8405-8507).

By "knock-in mutation" is meant the insertion of an exogenous nucleic acid, optionally, encoding a polypeptide, into the chromosome of a cell.

By "mutation" is meant an alteration in a naturally-occurring or reference nucleic acid sequence, such as an insertion, deletion, frameshift mutation, silent mutation, nonsense mutation, or missense mutation. Preferably, the amino acid sequence encoded by the nucleic acid sequence has at least one amino acid alteration from a naturally-occurring sequence. Examples of recombinant DNA techniques for altering the genomic sequence of a cell, embryo, fetus, or mammal include inserting a DNA sequence from another organism (e.g., a human) into the genome, deleting one or more DNA sequences, and introducing one or more base mutations (e.g., site-directed or random mutations) into a target DNA sequence. Examples of methods for producing these modifications include retroviral insertion, artificial chromosome techniques, gene insertion, random insertion with tissue specific promoters, homologous recombination, gene targeting, transposable elements, and any other method for introducing foreign DNA. All of these techniques are well known to those skilled in the art of molecular biology. A "non-naturally occurring mutation" is one that is introduced artificially, for example, by recombinant means.

By "non-human mammal comprising multiallellic mutations" or "multiallelic non-human mammal" is meant a mammal other than a human in which two alleles of an endogenous gene have been mutated. The mutations in the two alleles may or may not be in the same location, and may or may not be due to the same type of alteration. For example, the alleles of the gene in a multiallelic non-human mammal may be mutated by the insertion of two different polynucleotide sequences.

By "non-human mammal comprising multigenic mutations" or "multigenic non-human mammal" is meant a mammal other than a human in which two or more different genes have been mutated. The mutations in the two genes may or may not be in the same location and may or may not be due to the same type of alteration. For example, two genes in a multigenic non-human mammal may be mutated by the insertion of two different polynucleotide sequences.

By "nucleus" is meant a membrane-bounded organelle containing most or all of the DNA of a cell. The DNA is packaged into chromosomes in a decondensed form. Preferably, the membrane encapsulating the DNA includes one or two lipid bilayers or has nucleoporins.

By "permeabilization" is meant the formation of pores in the plasma membrane or the partial or complete removal of the plasma membrane.

By "placenta" is meant the membranous vascular organ that develops in female mammals during pregnancy, lining the uterine wall and partially enveloping the fetus, to which it is attached by the umbilical cord.

By "purified" is meant separated from other components that naturally accompany it. Typically, a factor is substantially pure when it is at least 50%, by weight, free from proteins, antibodies, and naturally-occurring organic molecules with which it is naturally associated. Preferably, the factor is at least 75%, more preferably, at least 90%, and most preferably, at least 99%, by weight, pure. A substantially pure factor may be obtained by chemical synthesis, separation of the factor from natural sources, or production of the factor in a recombinant host cell that does not naturally produce the factor. Proteins, vesicles, and organelles may be purified by one skilled in the art using standard techniques such as those described by Ausubel et al. Current Protocols in Molecular Biology, John Wiley & Sons, 1995). The factor is preferably at least 2, 5, or 10 times as pure as the starting material, as measured using polyacrylamide gel electrophoresis, column chromatography, optical density, HPLC analysis, or western blot analysis (Ausubel et al., supra). Preferred methods of purification include immunoprecipitation, column chromatography such as immunoaffinity chromatography, magnetic bead immunoaffinity purification, and panning with a plate-bound antibody.

By "recloned" is meant used in a subsequent (e.g., second) round of cloning. In particular, a cell from an embryo, fetus, or adult generated from the methods of the invention may be incubated in a mitotic reprogramming media (e.g., a mitotic cell extract) to form a chromatin mass for insertion into an enucleated oocyte, as described above. Alternatively, the cell may be permeabilized, incubated in a reprogramming media, and inserted into an enucleated oocyte, as described above. Performing two or more rounds of cloning may result in additional reprogramming of the donor chromatin mass or donor cell, thereby increasing the chance of generating a viable offspring after the last round of cloning.

By "reducing the expression of an endogenous antibody" is meant reducing the amount of endogenous, functional antibodies produced by a B-cell or a population of B-cells. This reduction in the amount of endogenous antibodies may be due to a decrease in the amount of endogenous antibodies produced per B-cell, a decrease in the number of functional endogenous B-cells, or a combination thereof. Preferably, the amount of an endogenous antibody secreted by a B-cell or expressed on the surface of a B-cell expressing or secreting endogenous antibody is reduced by at least 25, 50, 75, 90, or 95%. In another preferred embodiment, the number of endogenous B-cells in a sample from the recipient mammal, such as a blood sample, is reduced by at least 25, 50, 75, 90, or 95%.

By "reprogramming media" is meant a solution that allows the removal of a factor from a cell, nucleus, chromatin mass, or chromosome or the addition of a factor from the solution to the cell, nucleus, chromatin mass, or chromosome. Preferably, the addition or removal of a factor increases or decreases the level of expression of an mRNA or protein in the donor cell, chromatin mass, or nucleus or in a cell containing the reprogrammed chromatin mass or nucleus. In another embodiment, incubating a permeabilized cell, chromatin mass, or nucleus in the reprogramming media alters a phenotype of the permeabilized cell or a cell containing the reprogrammed chromatin mass or nucleus relative to the phenotype of the donor cell. In yet another embodiment, incubating a permeabilized cell, chromatin mass, or nucleus in the reprogramming media causes the permeabilized cell or a cell containing the reprogrammed chromatin mass or nucleus to gain or lose an activity relative to the donor cell.

Exemplary reprogramming media include solutions, such as buffers, that do not contain biological molecules such as proteins or nucleic acids. Such solutions are useful for the removal of one or more factors from a nucleus, chromatin mass, or chromosome. Other preferred reprogramming medias are extracts, such as cellular extracts from cell nuclei, cell cytoplasm, or a combination thereof. Exemplary cell extracts include extracts from oocytes (e.g., mammalian, vertebrate, or invertebrate oocytes), male germ cells (mammalian, vertebrate, or invertebrate germ cells such as spermatogonia, spermatocyte, spermatid, or sperm), and stem cells (e.g., adult or embryonic stem cells). Yet other reprogramming media are solutions or extracts to which one or more naturally-occurring or recombinant factors (e.g., nucleic acids or proteins such as DNA methyltransferases, histone deacetylases, histones, protamines, nuclear lamins, transcription factors, activators, repressors, chromatin remodeling proteins, growth factors, interleukins, cytokines, or other hormones) have been added, or extracts from which one or more factors have been removed. Still other reprogramming media include solutions of detergent (e.g., 0.01% to 0.1%, 0.1% to 0.5%, or 0.5% to 2% ionic or non-ionic detergent such as one or more of the following detergents: SDS, Triton X-100, Triton X-114, CHAPS, Na-deoxycholate, n-octyl glucoside, Nonidet P40, IGEPAL, Tween 20, Tween 40, or Tween 80), salt (e.g., ~0.1, 0.15, 0.25, 0.5, 0.75, 1, 1.5, or 2 M NaCl or KCl), polyamine (e.g., ~1 $\mu$M, 10 $\mu$M, 100 $\mu$M, 1 mM or 10 mM spermine, spermidine, protamine, or poly-L-lysine), a protein kinase (e.g., cyclin-dependent kinase 1, protein kinase C, protein kinase A, MAP kinase, calcium/calmodulin-dependent kinase, CK1 casein kinase, or CK2 casein kinase), and/or a phosphatase inhibitor (e.g., ~10 µM, 100 µM, 1 mM, 10 mM, 50 mM, 100 mM of one or more of the following inhibitors: Na-orthovanadate, Na-pyrophosphate, Na-fluoride, NIPP1, inhibitor 2, PNUTS, SDS22, AKAP149, or ocadaic acid) or nucleoplasmin. In some embodiments, the reprogramming medium contains an anti-NuMA antibody. If desired, multiple reprogramming media may be used simultaneously or sequentially to reprogram a donor cell, nucleus, or chromatin mass.

By "reprogrammed cell" is meant a cell that has been exposed to a reprogramming media. Preferably, at least 1, 5, 10, 15, 20, 25, 50, 75, 100, 150, 200, 300, or more mRNA or protein molecules are expressed in the reprogrammed cell that are not expressed in the donor or permeabilized cell. In another preferred embodiment, the number of mRNA or protein molecules that are expressed in the reprogrammed cell, but not expressed in the donor or permeabilized cell, is between 1 and 5, 5 and 10, 10 and 25, 25 and 50, 50 and 75, 75 and 100, 100 and 150, 150 and 200, or 200 and 300, inclusive. Preferably, at least 1, 5, 10, 15, 20, 25, 50, 75, 100, 150, 200, 300, or more mRNA or protein molecules are expressed in the donor or permeabilized cell that are not expressed in the reprogrammed cell. In yet another preferred embodiment, the number of mRNA or protein molecules that are expressed in the donor or permeabilized cell, but not expressed in the reprogrammed cell, is between 1 and 5, 5 and 10, 10 and 25, 25 and 50, 50 and 75, 75 and 100, 100 and 150, 150 and 200, or 200 and 300, inclusive. In still another preferred embodiment, these mRNA or protein molecules are expressed in both the donor cell (i.e., the donor or permeabilized starting cell) and the reprogrammed cell, but the expression levels in these cells differ by at least 2, 5, 10, or 20-fold, as measured using standard assays (see, for example, Ausubel et al., supra).

By "substantially identical" is meant having a sequence that is at least 80, 90, 95, 98, or 100% identical to that of another sequence. Sequence identity is typically measured using BLAST® (Basic Local Alignment Search Tool) or BLASTS 2 with the default parameters specified therein (see, Altschul et al. (1990) J. Mol. Biol. 215:403-410; and Tatiana et al. (1999) FEMS Microbiol. Lett. 174:247-250). These software programs match similar sequences by assigning degrees of homology to various substitutions, deletions, and other modifications. Conservative substitutions typically include substitutions within the following groups: glycine, alanine, valine, isoleucine, leucine; aspartic acid, glutamic acid, asparagine, glutamine; serine, threonine; lysine, arginine; and phenylalanine, tyrosine.

By "viable offspring" is meant an animal that survives ex utero. Preferably, the mammal is alive for at least one second, one minute, one hour, one day, one week, one month, six months, or one year from the time it exits the maternal host. The animal does not require the circulatory system of an in utero environment for survival.

Other features and advantages of the invention will be apparent from the following detailed description and from the claims.

Clear expression from a positive control "P" (commercially available polyA+ bovine spleen RNA) and the wild-type (#6939) fetuses (#1, #2), but not from IgμU$^{-/-}$ fetuses, was detected.

Figure 3:
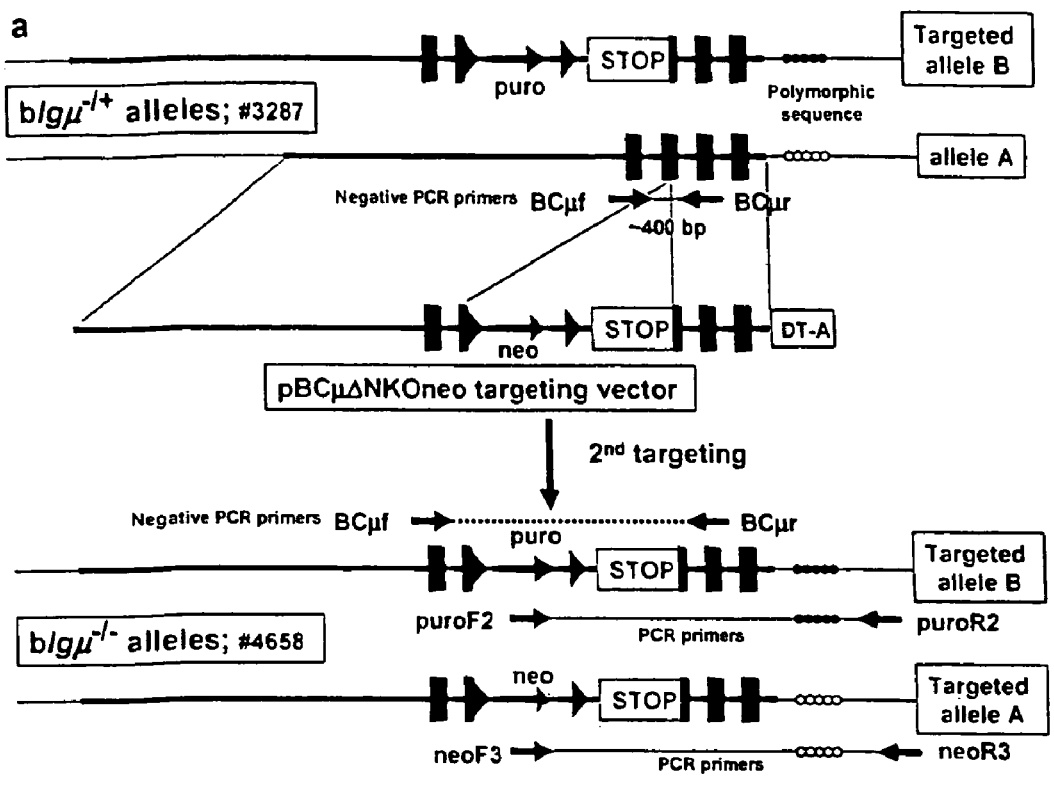
FIG. 3A is a schematic diagram depicting the structure of IgµU$^{-/+}$ #3287 alleles, the neo vector used for targeting the second allele, and the genomic PCR assay for the targeting events. Primer pairs, neoF3×neoR3 were used to identify the neo targeting event at allele A. BCµf×BCµr is a primer pair used to confirm the absence of wild-type alleles. The primers would not amplify sequence from the targeted alleles because of the presence of STOP cassettes.
FIG. 3B is a series of photographs representing the identification of IgµU$^{-/-}$ fetuses and fibroblasts by genomic PCR with puroF2×puroR2, neoF3×neoR3, and BCµf×BCµr primers. "P" is a positive control (mixture of about $10^4$ copies/µl of plasmid DNA covering either puroF2–puroR2 or neoF3–neoR3 region and #6939 genomic DNA). "N" is a negative control (mixture of either the 1st KO or 2nd KO vector and #6939 genomic DNA), and #6939 is the original fibroblast cell line. Cell lines #4658, #3655, #5109, #5139, and #4554 were positive for the targeting events both at allele A (neo-targeting) and B (puro-targeting), but negative for wild-type alleles.
FIG. 3C is a photograph showing RT-PCR analysis of IgµU expression in mRNA extracted from spleen in day 90 fetuses.
Figure 3:
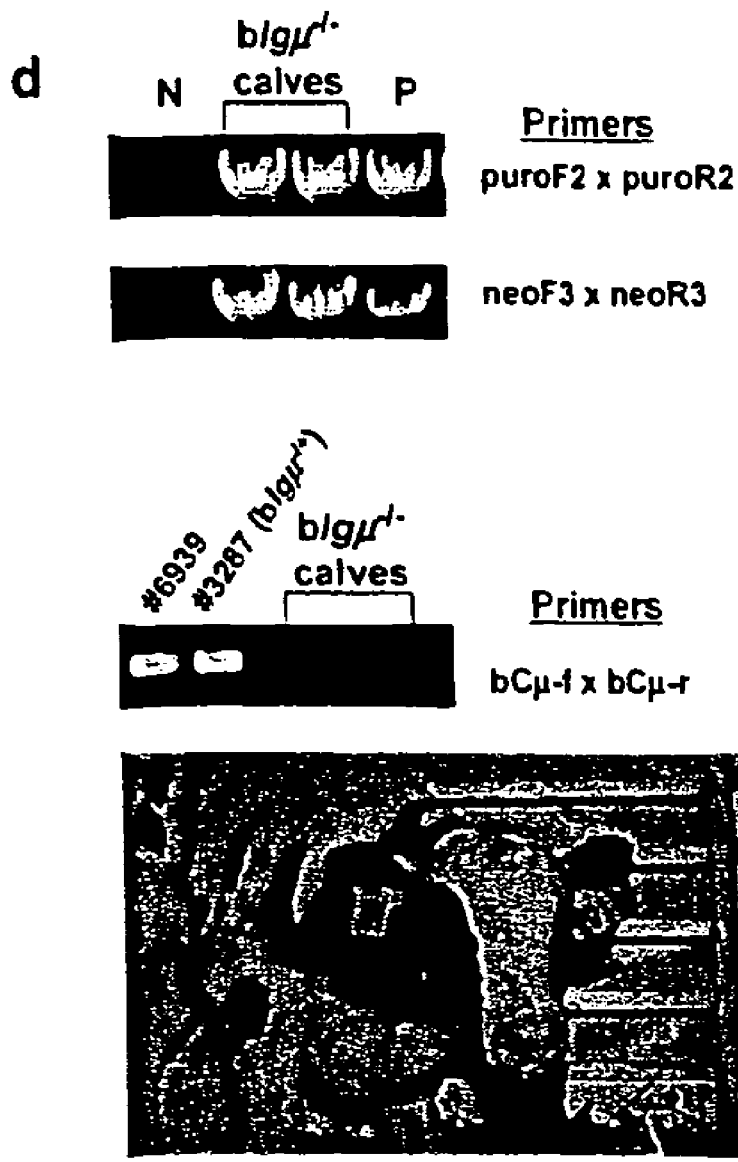

FIG. 3D is a series of photographs showing the genotyping of IgμU$^{-/-}$ calves by genomic PCR with puroF2×puroR2, neoF3×neoR3 and BCμf×BCμr primers. N is a negative control (mixture of either the 1st KO or 2nd KO vector and #6939 genomic DNA) and P is a positive control (mixture of about 10$^4$ copies/μl of plasmid DNA covering either puroF2-puroR2 or neoF3-neoR3 region and #6939 genomic DNA). The two IgμU$^{-/-}$ calves born (one of which is shown in FIG. 3D) were genotyped and were positive for targeting events at both allele B and A of IgμU gene but were negative for the wild-type allele.

Figure 4:
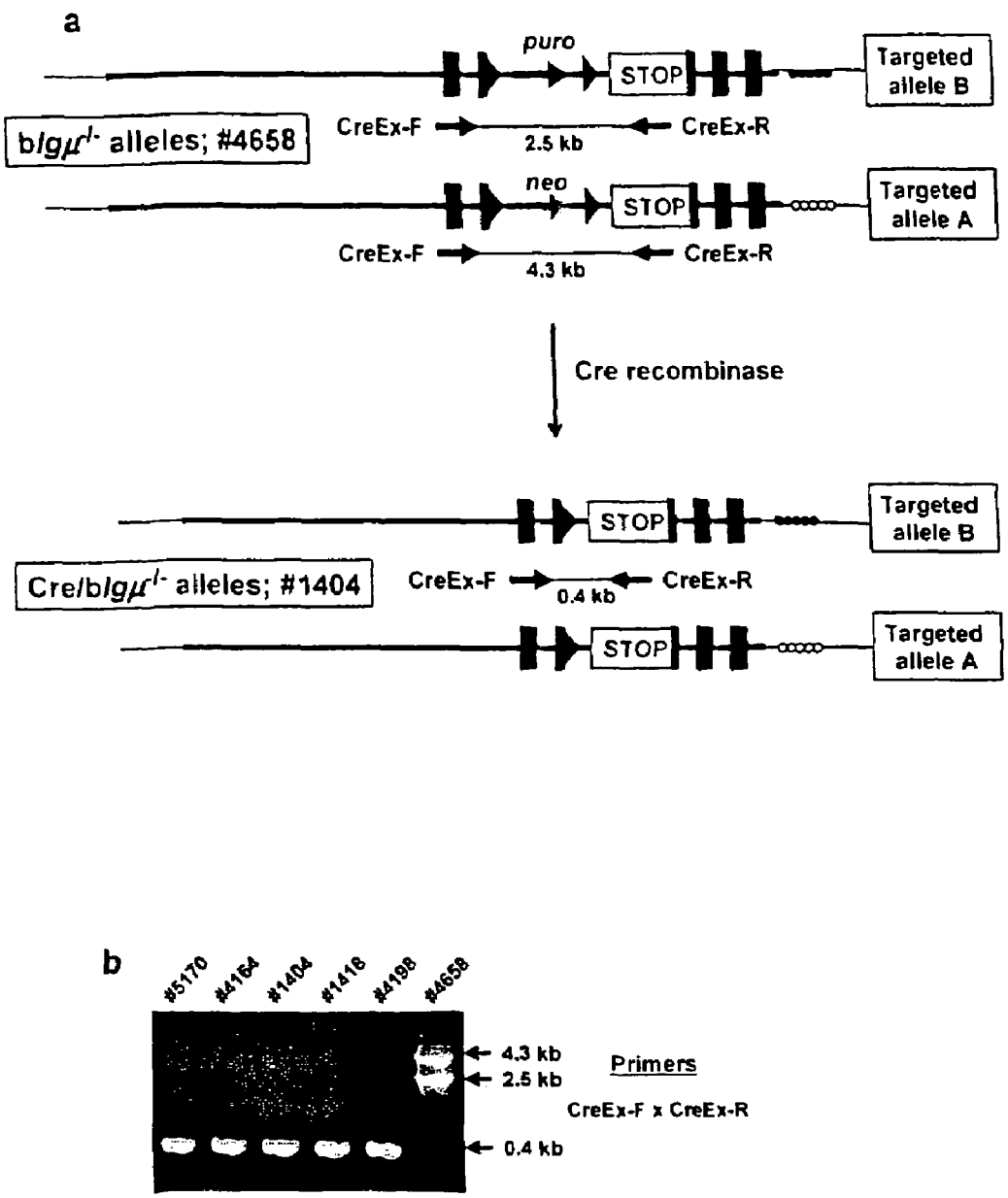

FIG. 4A is a schematic diagram representing the structure of IgμU$^{-/-}$ #4658 alleles and the genomic PCR assay for Cre-loxP mediated removal of selection marker genes. Amplification from primer pairs, CreExF×CreExR, results in a 2.5 kb fragment from the puro targeted allele, a 4.3 kb from the neo targeted allele, or a short 0.4 kb fragment when both selection marker genes are excised.

FIG. 4B is a photograph showing the identification of Cre/IgμU$^{-/-}$ fetuses and fibroblasts by genomic PCR with Cre-ExF×CreExR primers. In #4658 cell line, prior to introduction of Cre, 2.5 kb (puro) and 4.3 kb (neo) PCR products are detected. In the five Cre/IgμU$^{-/-}$ fetuses and cell lines, these bands completely disappear and, instead, a 0.4 kb (without puro and neo) band is detected.

FIG. 5A is a schematic diagram illustrating the structure of PrP locus in Cre/IgμU$^{-/-}$ #1404 cell line, the targeting vector for PrP gene, and the genomic PCR assay for the targeting event. The vector was composed of a 5' homologous arm (1.2 kb), a 3' homologous arm (8.3 kb), STOP cassette, DT-A gene and floxed neo gene. The vector was designed to insert the knockout cassette just behind its initial ATG codon located in exon 3 of the PrP locus. A single base pair polymorphism was found between allele C and allele D as indicated. Primer pair, neoF7×neoR7, was designed to show the neo targeting event and include the polymorphic base. PCR and sequencing products showed that the vector was integrated into allele C.

FIG. 5B is a series of photographs showing the identification of the triple targeted fetuses and fibroblast cell lines (IgμU$^{-/-}$/PrP$^{-/+}$) by genomic PCR with positive PrP primer pair, neoF7×neoR7, and negative IgμU primer pair, BCμf× BCμr. P is a positive control (mixture of about 10$^4$ copies/μl of plasmid DNA covering neoF7-neoR7 region and #6939 genomic DNA) and #1404 is a negative control. Cell lines derived from fetus #8103, 1661, 8375, 8112 and 8443 were positive for the PrP targeting and negative for wild-type IgμU alleles, demonstrating that they were triple targeted cell lines (IgμU$^{-/-}$/PrP$^{-/+}$).

Figure 6:
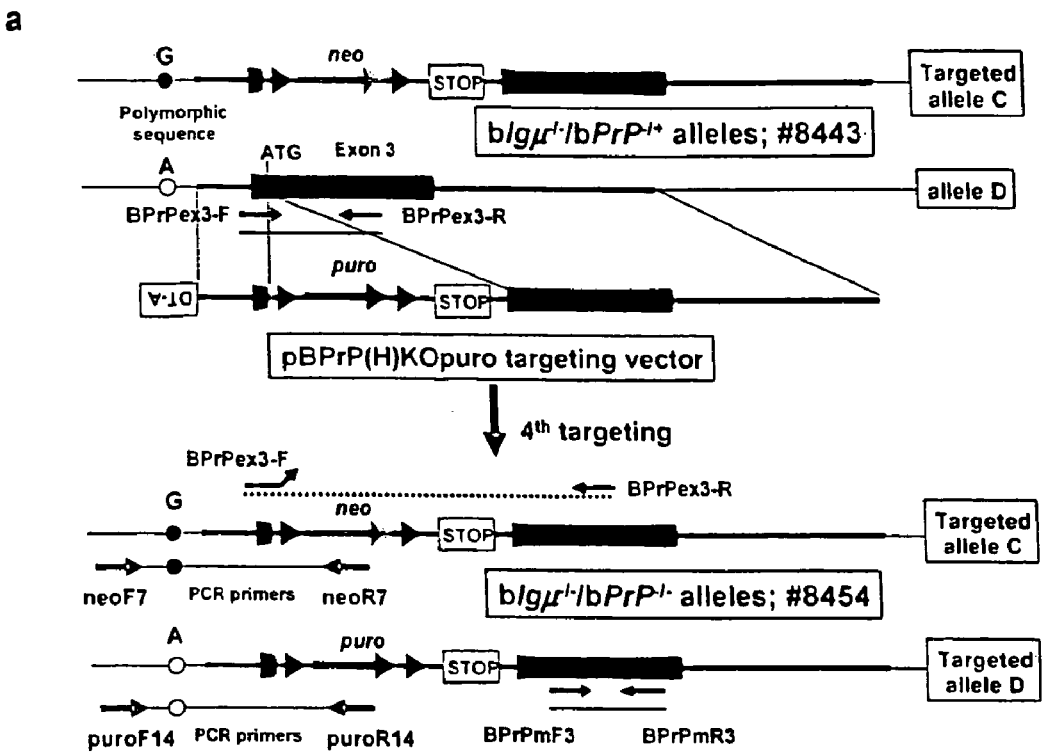

FIG. 6A is a schematic diagram showing the structure of IgμU$^{-/-}$/PrP$^{-/+}$ #8443 alleles, the puro vector used for targeting the second allele and the genomic PCR assay for the targeting events. Primer pairs, puroF14×puroR14 were used to identify the puro targeting event at allele D. BPrPex3F× BPrPex3R is a primer pair used to confirm the absence of wild-type alleles. The primers would not amplify sequence from the targeted alleles because of the disruption of annealing sites of BPrPex3F primer on the both alleles of PrP gene caused by the homozygous insertion.

FIG. 6B is a series of photographs showing the identification of double homozygous KO (IgμU$^{-/-}$/PrP$^{-/-}$) fetuses and fibroblasts by genomic PCR with puroF14×puroR14, neoF7× neoR7 and BPrPex3F×BPrPex3R primers. "P" is a positive control (mixture of about 10$^4$ copies/μl of plasmid DNA covering either puroF14–puroR14 or neoF7–neoR7 region and #6939 genomic DNA). "N" is a negative control (mixture of either the 3rd KO or 4th KO vector and #6939 genomic DNA) and the IgμU$^{-/-}$ fetal cell line (#4658) and the IgμU$^{-/-}$/PrP$^{-/+}$ cell line (#8443) are indicated. Cell line #8454, 8400 and 6397 are three of the double homozygous KO (IgμU$^{-/-}$/PrP$^{-/-}$) fetuses. They were positive to the 3rd and 4th targeting event at allele C (neo-targeting) and D (puro-targeting) of the PrP gene but negative to wild-type alleles.

FIG. 6C is a photograph showing RT-PCR analysis on the double homozygous KO (IgμU$^{-/-}$/PrP$^{-/-}$) fetuses. To detect PrP mRNA, PrPmF3×PrPmR3 primers were used. Clear expression from the #4658 (IgμU$^{-/-}$) and the #8443 (IgμU$^{-/-}$/PrP$^{-/+}$) fetuses, but no expression from the double homozygous KO (IgμU$^{-/-}$/PrP$^{-/-}$) fetuses was observed.

FIG. 7 shows the polynucleotide sequence of GenBank accession no. U63637 (SEQ ID NO: 75).

FIG. 8 shows the polynucleotide sequence of Bos taurus IgμU (GenBank accession no. U636372.2 (SEQ ID NO: 76)).

FIG. 9 shows a partial polynucleotide sequence of Bos taurus IgμAY (GenBank accession no. AY221099 (SEQ ID NO: 77)).

Figure 10:
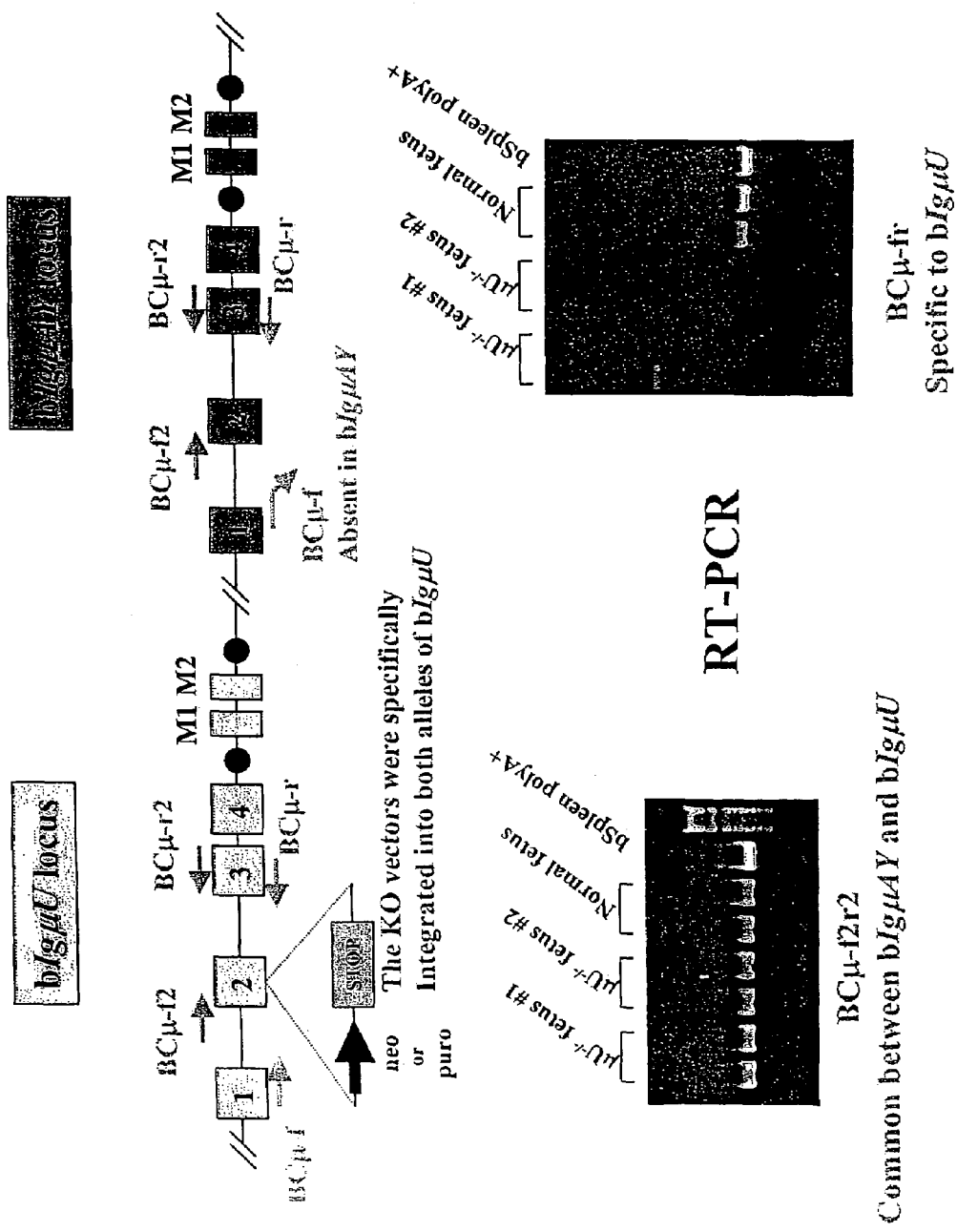

FIG. 10 is a schematic illustration showing that IgμAY could be detected by PCR in IgμU$^{-/-}$ cells.

Figure 11:
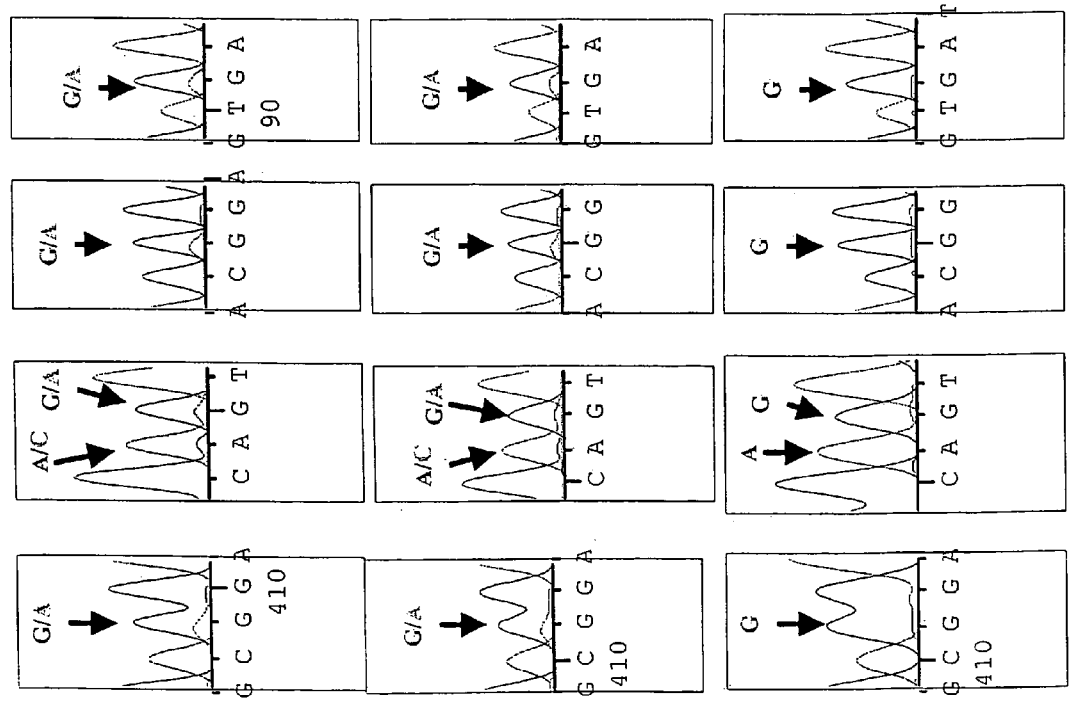

FIG. 11 is an illustration of a sequence trace showing that both IgμAY and IgμU undergo VDJ rearrangement and are expressed.

Figure 12:
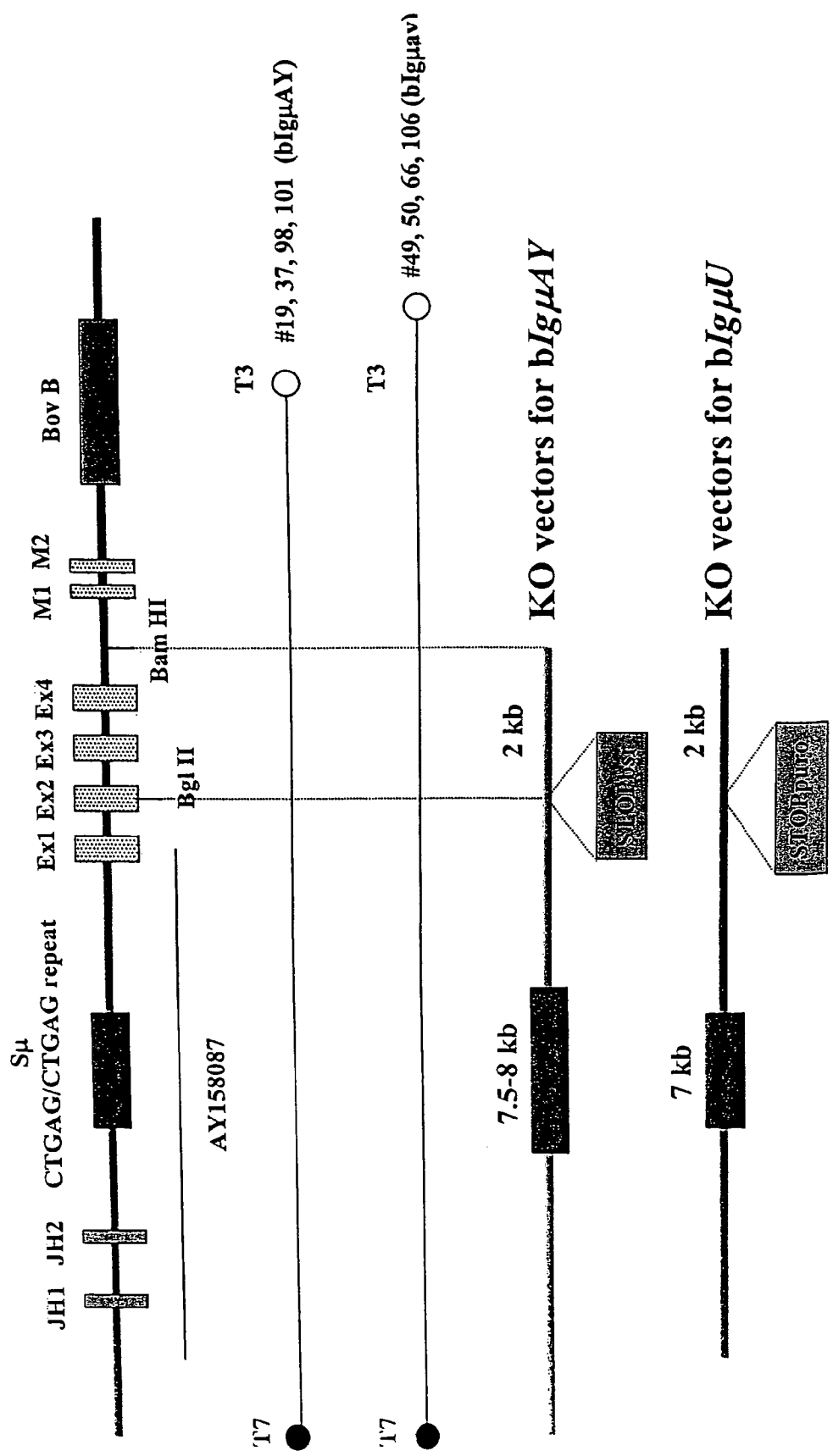

FIG. 12 is a schematic illustration showing the genomic organization of IgμAY.

FIG. 13 shows the sequence of the AY allele (SEQ ID NO: 78; SEQ ID NO: 80; and SEQ ID NO: 82) and ay allele (SEQ ID NO: 79; SEQ ID NO: 81; and SEQ ID NO: 83; and SEQ ID NO: 84) of IgμAY.

Figure 14:
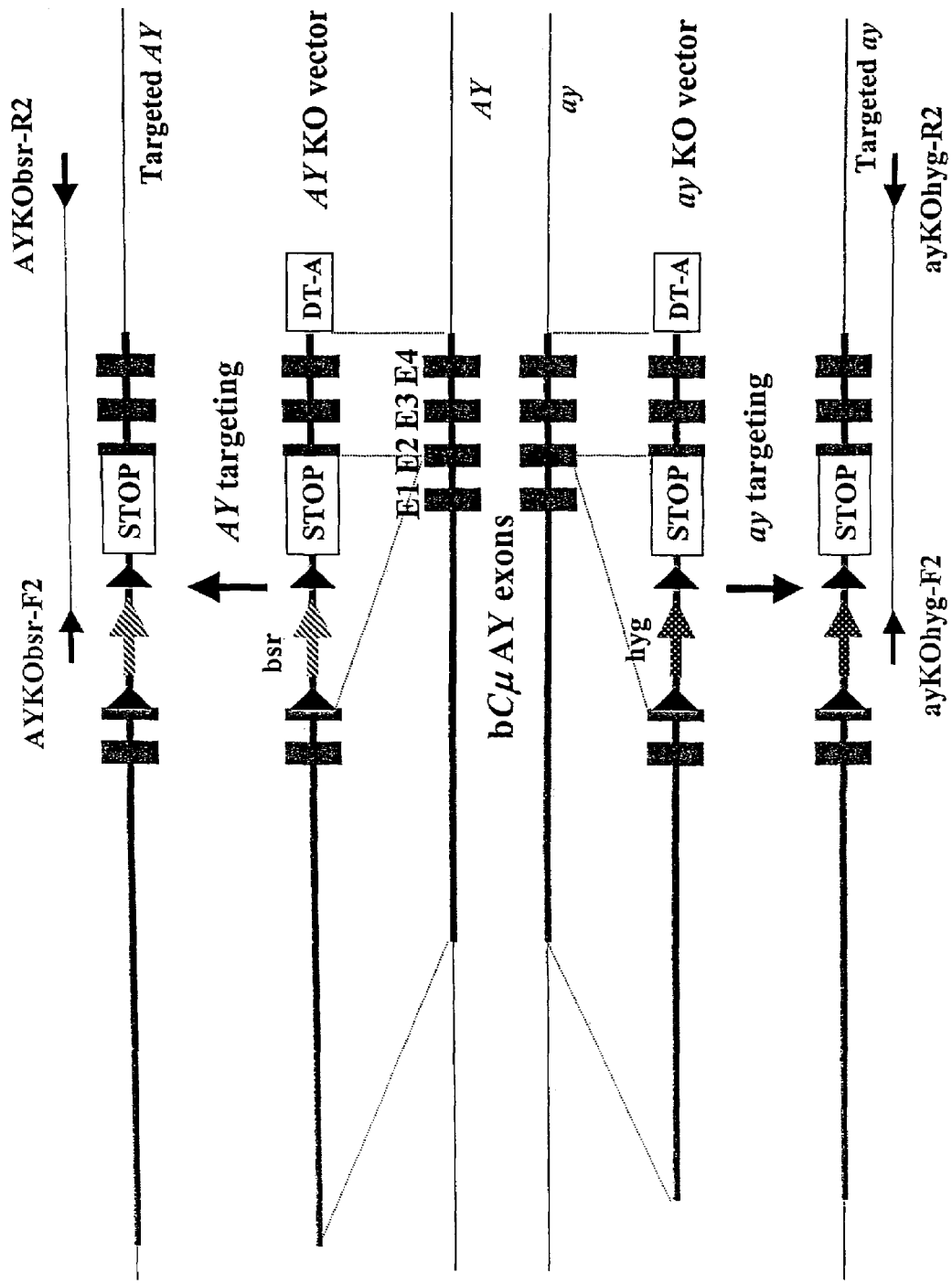

FIG. 14 is a schematic illustration showing the AY KO vector and the ay KO vector.

Figure 15:
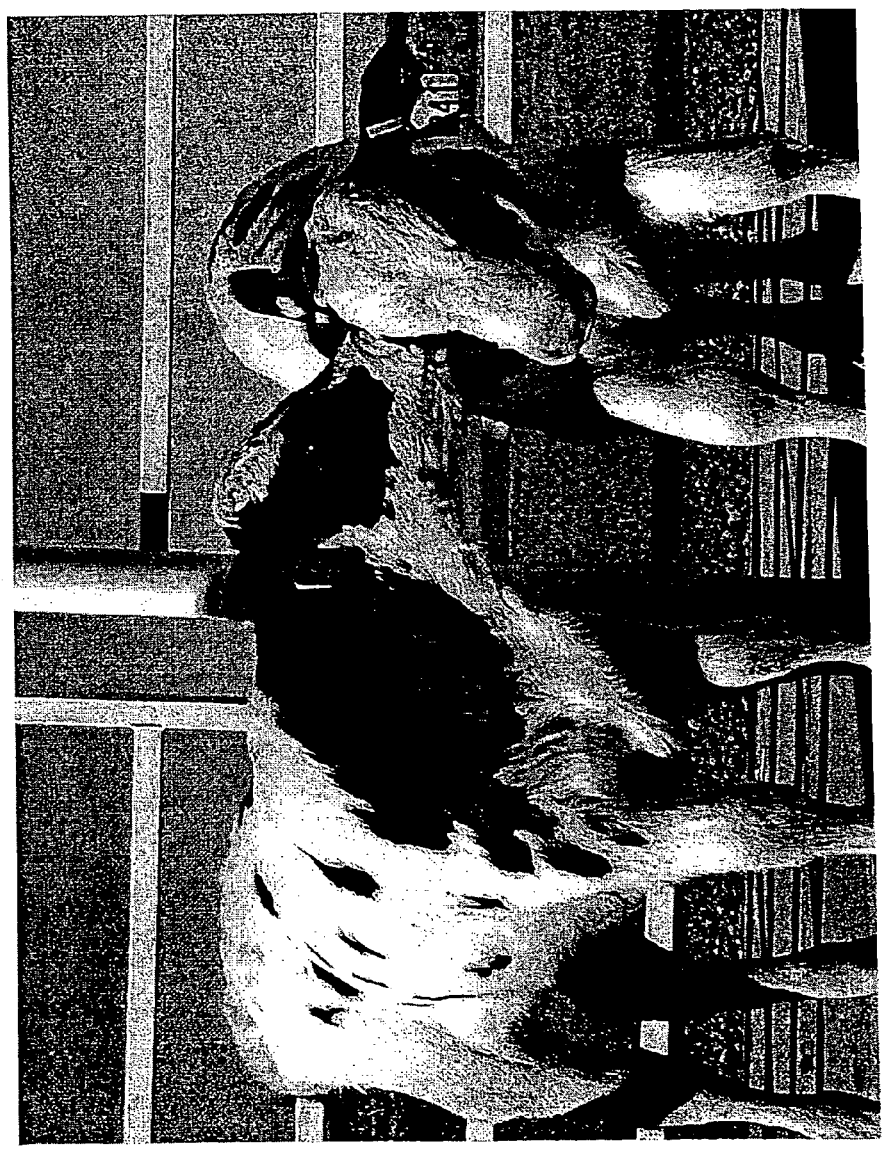

FIG. 15 illustrates PrP$^{+/+}$, PrP$^{-/+}$(341), PrP$^{-/-}$ (342) calves born simultaneously.

Figure 16B:
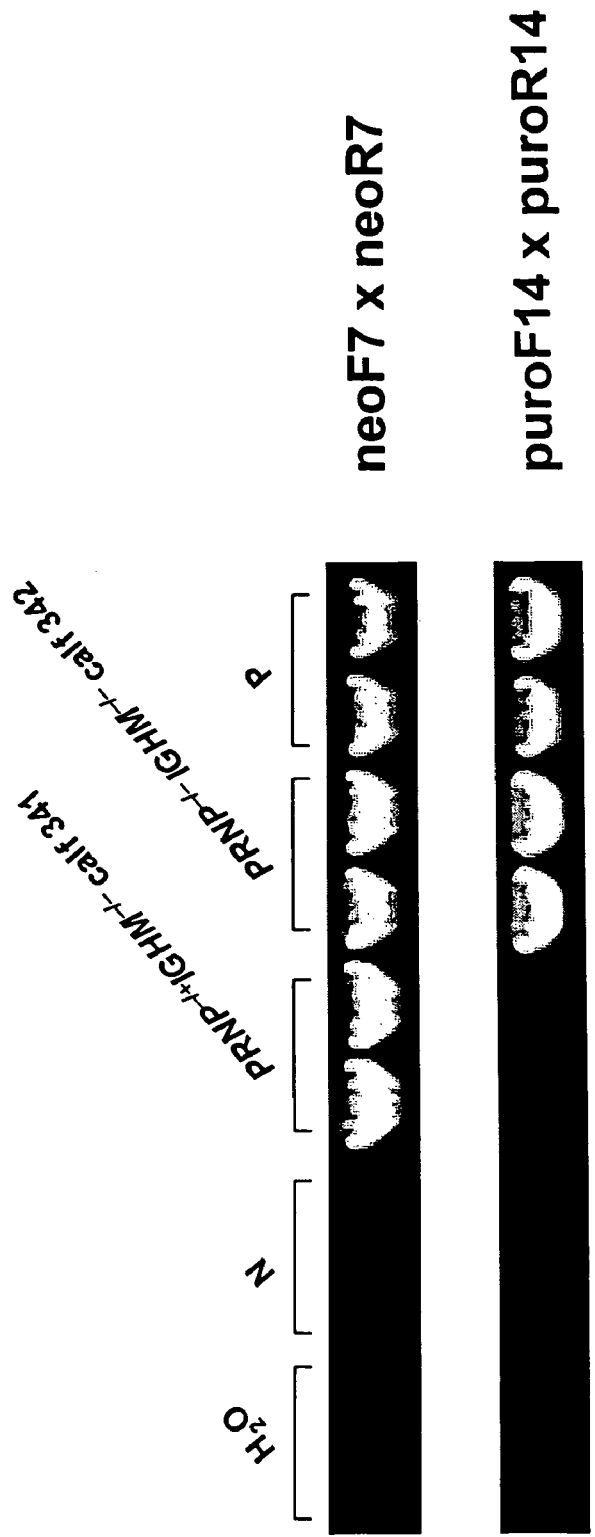
Figure 16C:
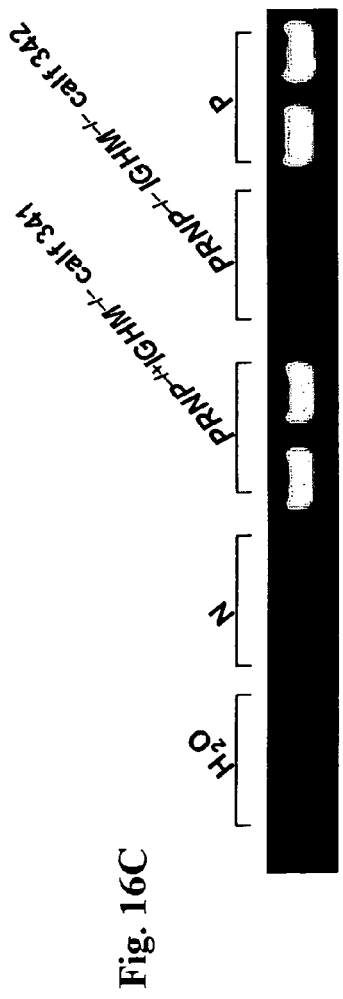
Figure 16D:
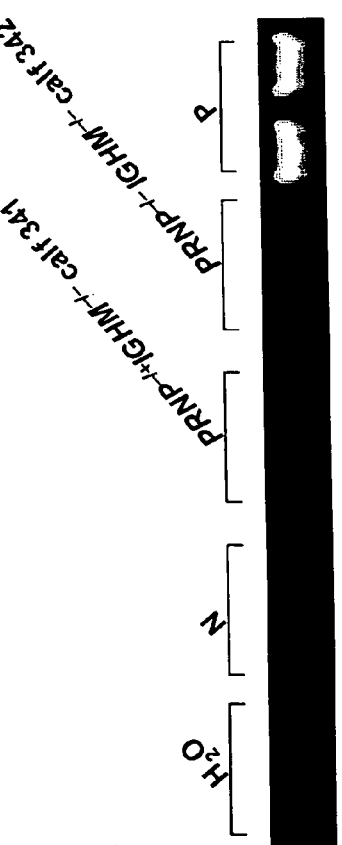

FIGS. 16A-16D illustrate genotyping of the PrP$^{-/-}$ IgμU$^{-/-}$ calf 342. FIG. 16A shows a fibroblast cell line established from an ear biopsy of PrP$^{-/-}$ IgμU$^{-/-}$ calf 342. FIG. 16B shows verification of the PrP$^{-/-}$ IgμU$^{-/-}$ genotype in the ear biopsy fibroblasts by genomic PCR. P, positive control; N, negative control. As indicated, using puroF14×puroR14 and neoF7×neoR7 primers, calf 342 was shown to be PCR-positive for targeting markers at both alleles of the PrP gene. FIG. 16C shows the absence of PrP wild type-derived alleles in the PrP$^{-/-}$ IgμU$^{-/-}$ calf. Calf 342 was PCR-negative for wild-type alleles of the PrP gene using BPrPex3F×BPrPex3R primers. FIG. 16D shows the additional absence of IgμU wild type-derived alleles in the PrP$^{-/-}$ IgμU$^{-/-}$ calf using BCμf×BCμr primers.

Figure 17A:
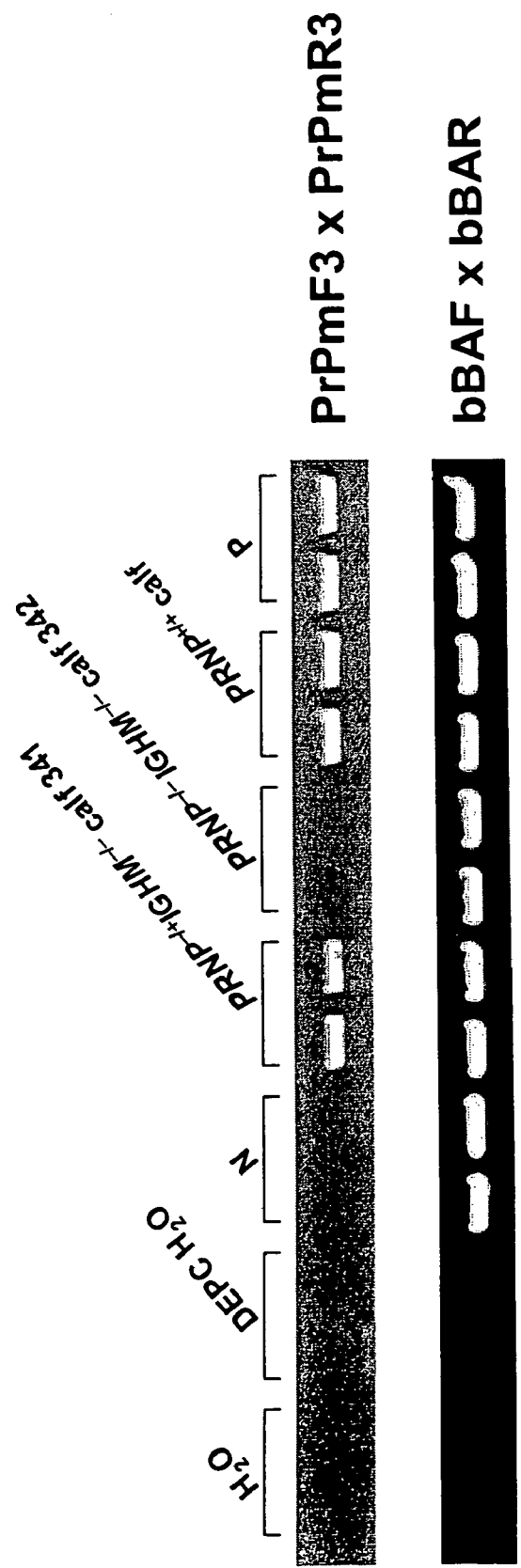
Figure 17B:
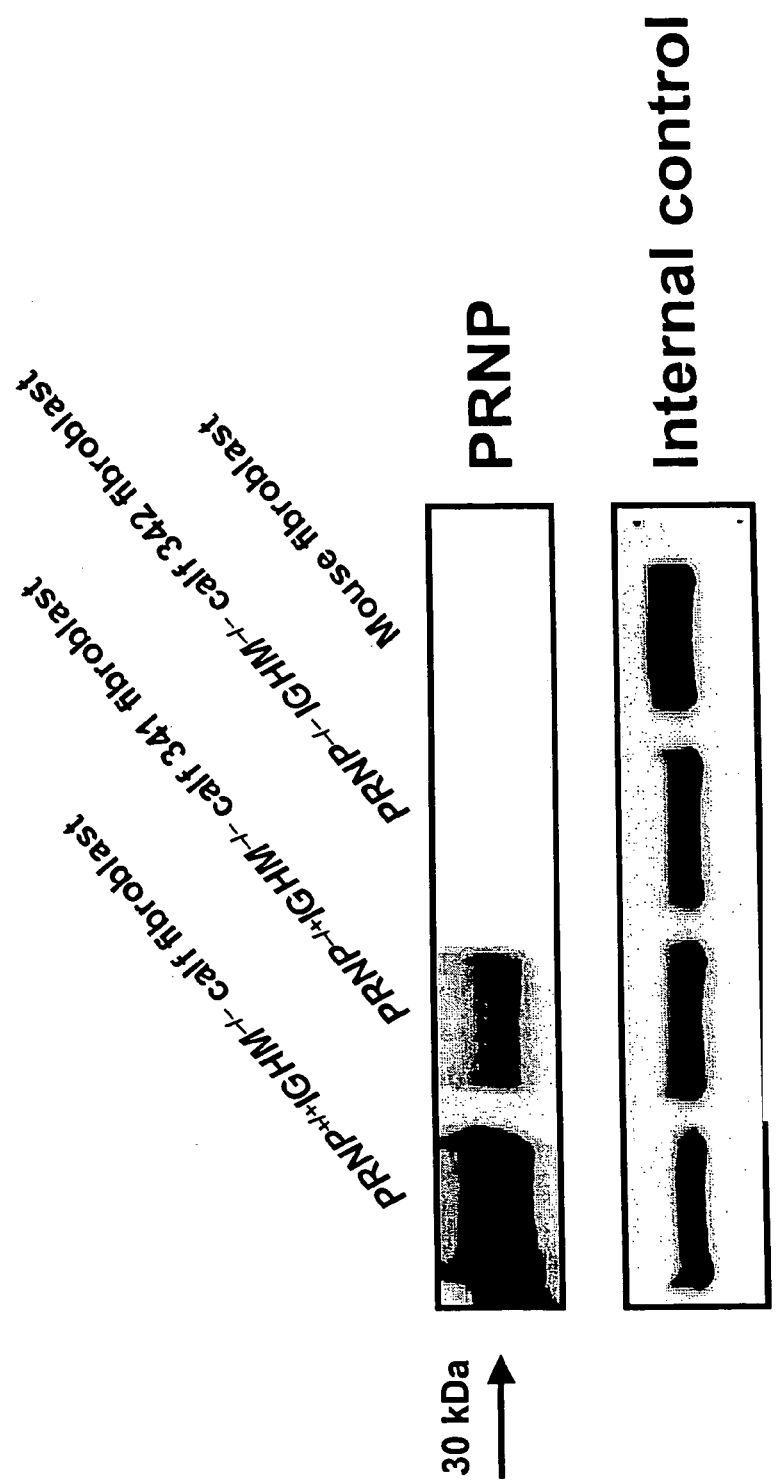

FIGS. 17A-17B illustrate functional inactivation of the PrP gene in PrP$^{-/-}$IgμU$^{-/-}$ calf 342. FIG. 17A shows disruption of mRNA expression in fibroblasts from PrP$^{-/-}$IgμU$^{-/-}$ calf 342. RT-PCR analysis on PrP$^{-/-}$/IgμU$^{-/-}$ calf 342 was carried out. To detect PrP mRNA, PrPmF3×PrPmR3 primers were used. Clear expression was detected in the PrP$^{+/+}$IgμU$^{-/-}$ and PrP$^{-/+}$IgμU$^{-/-}$ (calf 341) calves, but no expression was detected in PrP$^{-/-}$ IgμU$^{-/-}$ calf 342. As an internal positive control, bovine β-actin mRNA expression was also evaluated using primer pair bBAF×bBAR. FIG. 17B shows the absence of PrP protein in fibroblasts of PrP$^{-/-}$IgμU$^{-/-}$ calf 342. Western blot analysis on PrP$^{-/-}$ IgμU$^{-/-}$ calf 342 was performed. As a positive control, a PrP$^{+/+}$IgμU$^{-/-}$ calf was analyzed. As a negative control, protein extracts from mouse fibroblasts were used as the monoclonal antibody utilized for this analysis was stated to be specific for bovine PrP protein. The presence of a 33-35 kDa protein band (the size of bovine PrP) was detected in protein extracts from the PrP$^{+/+}$IgμU$^{-/-}$ and PrP$^{-/+}$IgμU$^{-/-}$ calves, but no positive band was detected in protein extracts from PrP$^{-/-}$IgμU$^{-/-}$ calf 342. The same blot was stained with anti-CDC2 monoclonal antibody as an internal positive control.

Figure 18:
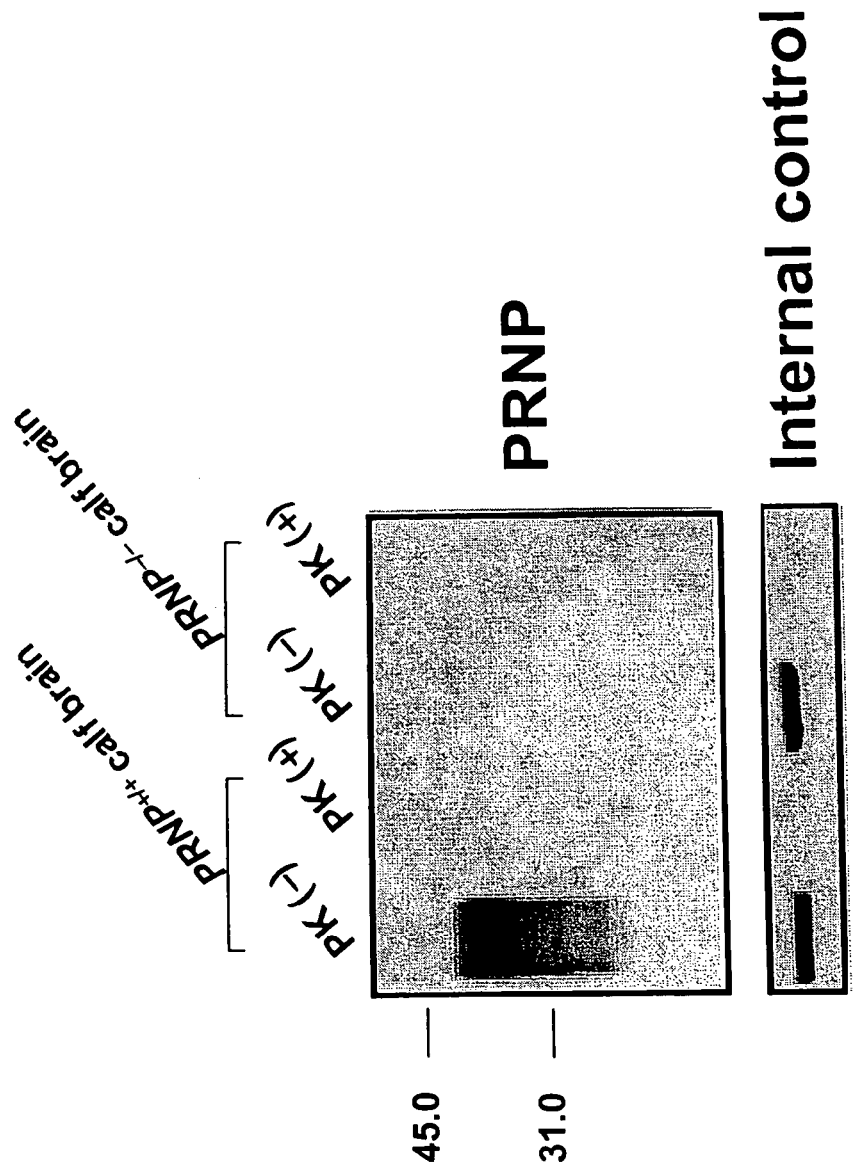

FIG. 18 illustrates the absence of PrP protein in the brain stems of PrP$^{-/-}$ calves. Western blot analysis on the brain stems of PrP$^{-/-}$ calves 354 and 282 was performed as described herein. No band for PrP protein was detected in the PrP$^{-/-}$ calves.

Figure 19:
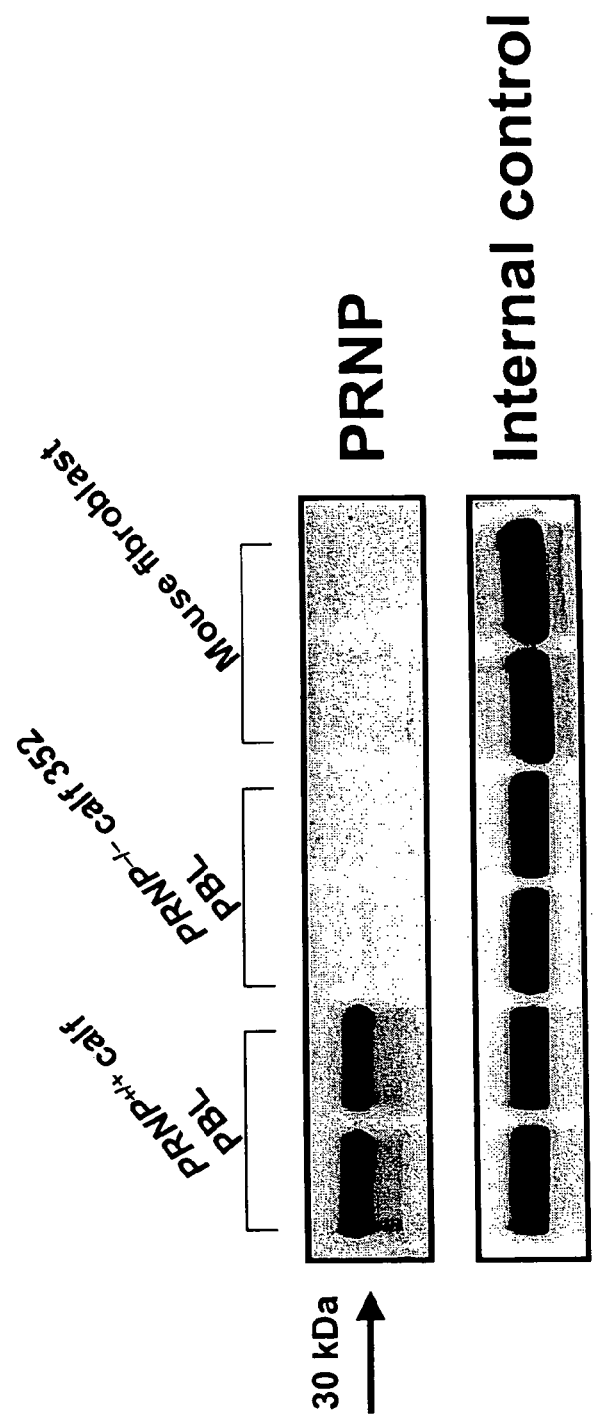

FIG. 19 illustrates the absence of PrP protein in peripheral blood lymphocytes (PBLs) of exemplary PrP$^{-/-}$ calf 352 cloned from a different PrP$^{-/-}$ fibroblast cell line. Western blot analysis of PBLs from PrP$^{-/-}$ calf 352 was performed. No positive band for the 33-35 kDa bovine PrP protein was detected.

DETAILED DESCRIPTION

In general, the invention features transgenic non-human mammals (e.g., bovines and other ungulates), and methods of making these mammals. In particular, the invention features transgenic ungulates having reduced levels of endogenous IgM heavy chain and/or prion protein. The invention is described in more detail below.

Methods for Producing Non-human Mammals and Cells Containing Multiallelic or Multigenic Mutations The present invention provides rapid methods to sequentially target transcriptionally silent and transcriptionally active genes in non-human mammals, such as cattle (e.g., bovine). More specifically, we have discovered a sequential gene targeting system that we first used to knock out both alleles of a silent gene, the bovine immunoglobulin μU (IgμU) gene, producing heterozygous and homozygous knockout calves. IgμU targeting was followed by sequential knockout targeting of both alleles of a transcriptionally active gene in fibroblasts, the bovine prion protein (PrP) gene, in the IgμU$^{-/-}$ cell line to produce double homozygous knockout fetuses. Using the methods of the invention, gene targeting can be performed sequentially in somatic cells, resulting in the production of multiallelic or multigenic non-human mammals. The present invention further employs cloning methods to rejuvenate cell lines following each round of targeting, as described in U.S. Patent Application Publication No. 2003-0046722, hereby incorporated by reference.

The disruption of a gene of interest first involves the production of hemizygous gene knockout cells and the production of a fetus by embryonic cloning. Genetically targeted cells are next harvested from the resulting fetuses at any time during gestation. In a bovine, such cell harvesting desirably occurs at between 25 to 90 days of gestation, at between 35 to 60 days of gestation, at between 35 to 50 days of gestation, preferably at between 35 to 45 days, more preferably at between 38 to 43 days, and most preferably at about 40 days of gestation. Next, the second allele of the same gene locus, or alternatively, an allele of a different endogenous gene is targeted in the harvested cells. These cells are next used to derive fetuses, from which somatic cells such as fibroblasts may further be isolated and used for further rounds of cloning. The above steps may then be repeated until cells containing the desired multiallelic or multigenic mutations are generated. If desired, these cells may be used to produce non-human mammals, such as ungulates.

Using the methods of the present invention, we show that each targeting event required approximately 2.5 months from transfection to establishment of regenerated cell lines, such that a single homozygous genetic modification could be made in calves in 14 months (including five months for targeting two alleles and nine months gestation) and a double homozygous modification could be made in 19 months. In contrast, breeding a heterozygous founder to produce homozygous calves would require approximately five years, making the generation of double homozygous calves from two heterozygous founders impractical. Using the sequential targeting strategy described herein, complex genetic modifications in large animal species are not only feasible but also straightforward and useful for many applications.

Genetically modified large animals are, in many cases, more suitable models for the study of human disease than mice, such as for the study of human cystic fibrosis, for example (Harris (1997) Hum. Mol. Genet. 6:2191-2194). Homozygous knockout targeting may also be useful, for example, for the elimination of bovine antibodies when attempting to produce human polyclonal antibodies in a genetically modified cow (Kuroiwa (2002) Nature Biotechnol. 20:889-894). Furthermore, the inactivation of the IgμU gene, for example, may be useful in investigating bovine immunology, such as the mechanism of B-cell development, which is known to be substantially different from that of humans or mice (Butler (1997) Rev. Sci. Tech. 17:43-70). Pigs carrying multiple KOs, not only for α-1,3-galactosyltransferase gene (Phelps et al. (2003) Science 299:411-414), but also for other genes, such as major histocompatibility complex (MHC) genes, may also be a more suitable source of organs and tissue for xenotransplantion. In agriculture, homozygous knockout targeting could be useful in improving the safety and disease-resistance of animals, such as the inactivation of the bovine prion gene, and elimination of the "mad-cow disease" threat. The methods of the invention are therefore useful for complex genetic modifications in animals for gene-functional analysis, as well as biomedical and agricultural applications, without the necessity of germ line transmission.

Transgenic Ungulates Having Reduced IgM Heavy Chain Protein

We have determined that there are two genes encoding bovine IgM heavy chains. The first published sequence asserted to encode bovine IgM is shown in FIG. 7. This sequence was first published in 1996 as GenBank accession no. U63637 (gi: 1575489) by Hammarstrom and colleagues, and subsequently described by them in Immunology (93: 581-588, 1998). U63637 was replaced on Feb. 27, 2003 with a second sequence (GenBank accession no. U63637.2; gi:2859209; FIG. 8). Later, Hammarstrom and colleagues submitted a third sequence, encoding Bos taurus heavy chain constant region (GenBank accession no. AY221099; gi:33413901; FIG. 9). In the paper accompanying this third submission (Zhao et al. (2003) J. Biol. Chem. 278:35024-35032), the authors concluded that the differences between the second and third sequences (the first having been retracted) were due to polymorphisms.

We now demonstrate that bovines contain and express two Igμ genes, which we refer to as IgμU and IgμAY. As both genes are expressed, to produce a bovine having no IgM heavy chain protein requires mutation of both genes.

Although only one IgM-encoding gene has been identified in other ungulates, it is likely, in view of our discovery of two Igμ genes in bovines, that additional such genes are present. These additional genes can be identified using standard techniques, such as those described herein.

To alter immunoglobulin genes of other ungulates, targeting vectors are designed, to contain three main regions. The first region is homologous to the locus to be targeted. The second region is a drug selection marker that specifically replaces a portion of the targeted locus. The third region, like the first region, is homologous to the targeted locus but is not contiguous with the first region in the wild type genome. Homologous recombination between the targeting vector and the desired wild type locus results in deletion of locus sequences between the two regions of homology represented in the targeting vector and replacement of that sequence with a drug resistance marker. In preferred embodiments the total size of the two regions of homology is approximately 6 kilobases, and the size of the second region that replaces a portion of the targeted locus is approximately 2 kilobases. This targeting strategy is broadly useful for a wide range of species from prokaryotic cells to human cells. The uniqueness of each vector used is in the locus chosen for gene targeting procedures and the sequences employed in that strategy. This approach may be used in all ungulates, including, without limitation, goats (*Capra hircus*), sheep (*Ovis aries*), and the pig (*Sus scrofa*), as well as cattle (*Bos taurus* and *Bos indicus*).

The use of electroporation for targeting specific genes in the cells of ungulates may also be broadly used in ungulates. The general procedure described herein is adaptable to the introduction of targeted mutations into the genomes of other ungulates. Modification of electroporation conditions (voltage and capacitance) may be employed to optimize the number of transfectants obtained from other ungulates.

In addition, the strategy used herein to target the heavy chain locus in cattle (i.e., removal of all coding exons and intervening sequences using a vector containing regions homologous to the regions immediately flanking the removed exons) may also be used equally well in other ungulates. For example, extensive sequence analysis has been performed on one immunoglobulin heavy chain locus of sheep (*Ovis aries*), and the sheep locus is highly similar to the bovine locus in both structure and sequence (GenBank accession nos. Z71572, Z49180 through Z49188, M60441, M60440, AF172659 through AF172703). In addition to the large number of cDNA sequences reported for rearranged *Ovis aries* immunoglobulin chains, genomic sequence information has been reported for the heavy chain locus, including the heavy chain 5' enhancer (GenBank accession no. Z98207), the 3' mu switch region (GenBank accession no. Z98680) and the 5' mu switch region (GenBank accession no. Z98681). The complete mRNA sequence for the sheep secreted-form of the heavy chain has been deposited as GenBank accession no. X59994. This deposit contains the entire sequence of four coding exons, which are very similar to the corresponding bovine sequence.

Thus, the present invention relates to the production of a transgenic ungulate, preferably a transgenic cow, in which endogenous IgM expression has been reduced or eliminated by the mutation of two or more Ig, genes. Optionally, a nucleic acid (e.g., an artificial chromosome) has been stably introduced that comprises genes that are sufficient for the production of functional antibodies of another species, preferably human.

Transgenic Ungulates having Reduced Prion Protein

As described herein, Applicants have successfully produced a healthy PrP-deficient calf by means of sequential gene targeting. Such animals provide an improved population for production of BSE-free bovine-derived agricultural and biomedical materials, including milk, gelatin, collagen, and serum, as well as an improved source for human recombinant protein production for human therapy and medical materials for human xenotransplantation. The bovine or bovine fetuses of the invention may be used to produce any product normally derived agriculturally from such animals. They may also be used to produce any recombinant protein, including, without limitation, human antibodies, for example, by any of the methods described in U.S. Patent Application Publication Nos. 2003-0037347, 2004-0068760, and 2003-0056237, or PCT Publication No. WO2004/044156, all hereby incorporated by reference.

Non-human Mammalian Cells

As discussed herein, the methods of the present invention involve the introduction of mutations into somatic non-human mammalian cells, such as somatic ungulate cells. Suitable somatic cells include cells from embryos, fetuses, calves, or adult animals. Preferred cells for gene targeting include differentiated cells such as fibroblasts, epithelial cells, neural cells, epidermal cells, keratinocytes, hematopoietic cells, melanocytes, chondrocytes, B-lymphocytes, T-lymphocytes, erythrocytes, macrophages, monocytes, placental, and muscle cells. Preferred cells also include those from any organ, such as the bladder, brain, esophagus, fallopian tube, heart, intestines, gallbladder, kidney, liver, lung, ovaries, pancreas, prostate, spinal cord, spleen; stomach, testes, thymus, thyroid, trachea, ureter, urethra, and uterus. Preferably, the donor cell, donor nucleus, donor chromatin mass, or reconstituted oocyte is not tetraploid.

Cells may be derived from any non-human mammal, including an ungulate, rabbit, mouse, rat, or primate. Ungulates include members of the orders Perissodactyla and Artiodactyla, such as any member of the genus Bos. Other preferred ungulates include sheep, big-horn sheep, goats, buffalos, antelopes, oxen, horses, donkeys, mule, deer, elk, caribou, water buffalo, camels, llama, alpaca, pigs, and elephants. Most preferably, the non-human mammal is a bovine (e.g., *Bos taurus* or *Bos indicus*).

If a cell to be genetically targeted is derived from an embryo or a fetus, the cell may be isolated at any time during the gestation period until the birth of the genetically altered non-human mammal. As discussed above, bovine cells are desirably isolated at between 25 to 90 days of gestation, between 35 to 60 days of gestation, between 35 to 50 days, preferably between 35 to 45 days, more preferably between 38 to 43 days, and most preferably at about 40 days of gestation. Ovine cells are desirably isolated at between 25 to 150 days of gestation, between 30 to 100 days, preferably between 35 to 80 days, more preferably between 35 to 60 days, and most preferably at about 40 days of gestation. Equine cells are desirably isolated at between 25 to 300 days of gestation, between 30 to 100 days, preferably between 35 to 80 days, more preferably between 35 to 60 days, and most preferably at about 40 days of gestation. Porcine cells are desirably isolated at between 25 to 110 days of gestation, between 30 to 90 days, preferably between 30 to 70 days, more preferably between 30 to 50 days, and most preferably at about 35 days of gestation. Caprine cells are desirably isolated at between 25 to 150 days of gestation, between 30 to 100 days, preferably between 35 to 80 days, more preferably between 35 to 60 days, and most preferably at about 40 days of gestation. Primate cells are desirably isolated at between 25 to 150 days of estation, between 30 to 100 days, preferably between 35 to 80 days, more preferably between 35 to 60 days, and most preferably at about 40 days of gestation. Rodent cells are desirably isolated at between 6 to 18 days of gestation, between 8 to 16 days, preferably between 10 to 16 days, more preferably between 12 to 16 days, and most preferably at about 14 days of gestation.

The recipient cell is preferably an oocyte, a fertilized zygote, or a two-cell embryo, all of which may or may not have been enucleated. Typically, the donor and the recipient cell are derived from the same species. However, there has been success reported in achieving development from embryos reconstructed using donor and recipient cells from different species.

Gene Targeting

In general, the genetic targeting events of the invention may include inactivation, removal, or modification of a gene; upregulation of a gene; gene replacement; or transgene replacement at a predetermined locus. Examples of genes that may be targeted resulting in their inactivation, removal, or modification are genes encoding antigens which are xenoreactive to humans (e.g., α-1,3 galactosyltransferase); antibody-encoding genes; genes in the PrP locus responsible for the production of the prion protein and its normal counterpart in non-human animals; genes which in humans are responsible for genetic disease and which in modified, inactivated, or deleted form could provide a model of that disease in animals (e.g., the cystic fibrosis transmembrane conductance regulator gene); genes responsible for substances which provoke food intolerance or allergy; genes responsible for the presence of particular carbohydrate residues on glycoproteins (e.g., the cytidine monophospho-N-acetyl neuraminic acid hydroxylase gene in non-human animals); and genes responsible for the somatic rearrangement of immunoglobulin genes, such as RAG1 and RAG2.

Among genes that can be targeted resulting in their upregulation are genes responsible for suppression of complement-mediated lysis (e.g., porcine CD59, DAF, and MCP). Furthermore and as described further below, replacement of genes may also be performed. Genes that may be replaced include genes responsible for the production of blood constituents (e.g., serum albumin), genes responsible for substances that provoke food intolerance or allergy, immunoglobulin genes, and genes responsible for surface antigens.

Using the methods of the present invention, the time necessary for the identification, isolation, analysis, and expansion of primary cell clones carrying targeted events is significantly minimized. This is an important aspect of the invention because reduction of the time in culture increases the likelihood that cells used as nuclear donors are viable, normal, and euploid.

Targeting Constructs

Targeted gene mutation requires generating a nucleic acid construct having regions of homology to the targeted allele in the gene of interest such that integration of the construct into the genomic allele disrupts its expression. Thus, to alter a gene, a targeting vector is designed to contain three main regions. The first region is homologous to the locus to be targeted. The second region is a polynucleotide sequence (e.g., encoding a selection marker such as an antibiotic resistance protein) that specifically replaces a portion of the targeted locus. The third region, like the first region, is homologous to the targeted locus but is not contiguous with the first region in the wild type genome. Homologous recombination between the targeting vector and the desired wild-type locus results in deletion of locus sequences between the two regions of homology represented in the targeting vector and replacement of that sequence, for example, with a drug resistance marker. The uniqueness of each vector used is in the locus chosen for gene targeting procedures and the sequences employed in that strategy. This approach may be used in all mammals, including ungulates such as, goats (*Capra hircus*), sheep (*Ovis aries*), pigs (*Sus scrofa*), and cattle (*Bos taurus* or *Bos indicus*). Exemplary vectors for carrying out such targeted mutation are described herein. Methods for constructing vectors that provide for homologous recombination at other targeted sites are well known to those skilled in the art. Moreover, the construction of a suitable vector is within the level of skill in the art.

In order to facilitate homologous recombination, the vectors used to effect homologous recombination and inactivation of a gene of interest, respectively, contain portions of DNA that exhibit substantial sequence identity to the genes to be targeted. Preferably, these sequences have at least 98% sequence identity, more preferably, at least 99% sequence identity, and even 100% sequence identity with the targeted gene loci to facilitate homologous recombination. In preferred embodiments, the total size of the two regions of homology is approximately 9-9.5 kilobases and the size of the second region that replaces a portion of the targeted locus is approximately 2 kilobases.

Typically, the construct includes a marker gene that allows for the selection of desired homologous recombinants, for example, cells in which the gene of interest has been disrupted by homologous recombination. Marker genes include antibiotic resistance markers, drug resistance markers, and green fluorescent protein, among others. One neomycin resistance construct was assembled as follows. A construct designated "pSTneoB" (Katoh et al. (1987) Cell Struct. Funct. 12:575; Japanese Collection of Research Biologicals (JCRB) deposit number: VE039) was designed to contain a neomycin resistance gene under the control of an SV40 promoter and TK enhancer upstream of the coding region. Downstream of the coding region is an SV40 terminator sequence. The neo cassette was excised from "pSTneoB" as an XhoI fragment. After the ends of the fragment were converted to blunt ends using standard molecular biology techniques, the blunt ended fragment was cloned into the EcoRV site in the vector, pBS246 (Gibco/Life Technologies). This site is flanked by loxP sites. The new construct, designated "pLoxP-STNeoR", was used to generate the mu knockout DNA construct. The desired fragment of this construct is flanked by loxP sites and NotI sites, which were originally present in the pBS246 cloning vector. The desired NotI fragment, which contains loxP-neo-loxP, was used for replacement of the immunoglobulin mu constant region exons. The SV40 promoter operably linked to the neomycin resistance gene activates the transcription of the neomycin resistance gene, allowing cells in which the desired NotI fragment has replaced the mu constant region exons to be selected based on their resulting antibiotic resistance.

The strategy used herein to target genes in cattle (i.e., removal of a portion of the coding region and intervening sequences using a vector containing regions homologous to the regions immediately flanking the removed exons) may also be used in other mammals. For example, extensive sequence analysis has been performed on one immunoglobulin heavy chain locus of sheep (*Ovis aries*), and the sheep locus is highly similar to the bovine locus in both structure and sequence (GenBank accession nos. Z71572, Z49180 through Z49188, M60441, M60440, AF172659 through AF172703). In addition to the large number of cDNA sequences reported for rearranged *Ovis aries* immunoglobulin chains, genomic sequence information has been reported for the heavy chain locus, including the heavy chain 5' enhancer (GenBank accession no. Z98207), the 3' mu switch region (GenBank accession no. Z98680) and the 5' mu switch region (GenBank accession no. Z98681). The complete mRNA sequence for the sheep secreted form of the heavy chain has been deposited as GenBank accession no. X59994. This deposit contains the entire sequence of four coding exons, which are very similar to the corresponding bovine sequence. Accordingly, the GenBank sequence may be used to determine areas of high homology with the bovine IgpU sequence for the design of PCR primers. Because non-isogenic DNA was used to target bovine cells, finding areas of high homology with sheep sequence was used as an indicator that similar conservation of sequences between breeds of cow was likely. Given the similarity between the sequences and structures of the bovine and ovine immunoglobulin loci, the targeting strategies used herein to remove bovine immunoglobulin loci may be applied to the ovine system. In addition, existing information on pigs (*Sus scrofa*; GenBank accession no. S42881) and goats (*Capra hircus*; GenBank accession no. AF140603) indicates that the immunoglobulin loci of both of these species are also sufficiently similar to the bovine loci to utilize the present targeting strategies.

In one method of targeting cells, the targeting construct includes regulatory expression for driving expression of the marker gene, as well as a polyadenylation signal sequence. Such a construct allows for detection of the inserted sequence independent of the expression of the mutagenized gene and thus permits the identification of recombinants in silent genes (i.e., genes that are not expressed in fibroblasts). In order to determine whether the marker gene integrated into the genome by means of homologous recombination rather than through random insertion, one may use standard molecular biology techniques such as Southern blotting, PCR, or DNA sequencing.

Selection of Targeted Cells

Genetically targeted cells are typically identified using a selectable marker. If a cell already contains a selectable marker however, a new targeting construct containing a different selectable marker may be required. Alternatively, if the same selectable marker is employed, cells may be selected in the second targeting round by raising the drug concentration (for example, by doubling the drug concentration).

Targeting constructs may also contain selectable markers flanked by loxP sites to facilitate the efficient deletion of the marker using the Cre/lox system. Thus, at some point after the gene targeting event and preferably before any embryo cloning, such excision may be performed to remove portions of genetic material from the cell. This material may be a selectable marker or an introduced genetic transcription activator. This removal may be carried out by procedures described hereinafter, or by other procedures well known in the art.

In one example, fetal fibroblasts carrying the targeting vector are transfected via electroporation with a Cre containing plasmid (e.g., a Cre plasmid that contains a GFPCre fusion gene as described by Gagneten et al. (1997) Nucleic Acids Res. 25:3326-3331). This allows for the rapid selection of all clones that contain a Cre protein. In this regard, cells are selected either by FACS sorting or by manual harvesting of green fluorescing cells via micromanipulation. Cells that are green are expected to carry actively transcribed Cre recombinase, which would remove the drug resistance marker. Cells selected for Cre expression are cloned and analyzed for the deletion of the drug resistance marker by PCR analysis. Following such confirmation, such cells are used for the next round of genetic targeting or for cloning.

Introduction of Xenogenous Nucleic Acids

If desired, xenogenous nucleic acid molecules encoding a desired polypeptide may be inserted into an endogenous gene as part of the introduced mutation. For example, genes encoding antibodies of a particular species may be introduced into an endogenous gene. Preferably, human artificial chromosomes are used for this purpose, such as those disclosed in PCT Publication Nos. WO97/07671 and WO00/10383, each hereby incorporated by reference. These human artificial chromosomes also are described in a corresponding issued Japanese Patent JP 30300092. The construction of artificial human chromosomes that contain and express human immunoglobulin genes is disclosed in Shen et al. (1997) Hum. Mol. Genet. 6:1375-1382; Kuroiwa et al. (2000) Nature Biotechnol. 18:1086-1090; and Loupert et al. (1998) Chromosome 107:255-259. Following the stable insertion of the artificial chromosome, the cell line (e.g., a bovine fetal fibroblast) may be used as a donor cell for further gene targeting.

As an alternative to the use of human artificial chromosome, polynucleotides encoding genes of interest may also be integrated into the chromosome using a YAC vector, BAC vector, or cosmid vector. Such vectors may be introduced into cells (e.g., fetal fibroblasts cells) using known methods, such as electroporation, lipofection, fusion with a yeast spheroplast comprising a YAC vector, and the like. Desirably, vectors containing genes of interest may be targeted to the endogenous corresponding gene loci of the cells (e.g., fetal fibroblasts), resulting in the simultaneous introduction of the gene of interest and the mutation of the endogenous gene.

Integration of a nucleic acid encoding a gene of interest may also be carried out as described in the patents by Lonberg et al. (U.S. Pat. Nos. 5,545,806, 5,569,825, 5,625,126, 5,633,425, 5,661,016, 5,750,172, 5,770,429, 5,789,650, 5,814,318 5,874,299, 5,877,397, and 6,300,129, all of which are hereby incorporated by reference). In the "knock-in" construct used for the insertion of gene of interest into a chromosome of a host mammal, one or more genes and an antibiotic resistance gene may be operably-linked to a promoter which is active in the cell type transfected with the construct. For example, a constitutively active, inducible, or tissue-specific promoter may be used to activate transcription of the integrated antibiotic resistance gene, allowing transfected cells to be selected based on their resulting antibiotic resistance. Alternatively, a knock-in construct in which the knock-in cassette containing the gene(s) of interest and the antibiotic resistance gene is not operably linked to a promoter may be used. In this case, cells in which the knock-in cassette integrates downstream of an endogenous promoter may be selected based on the resulting expression of the antibiotic resistance marker under the control of the endogenous promoter. These selected cells may be used in the embryo cloning procedures described herein to generate a transgenic non-human mammal containing a gene of interest integrated into a host chromosome. Alternatively, an animal containing exogenous genes of interest may be mated with an animal in which the endogenous gene is inactivated.

Exemplary Gene Mutations

Any number of exemplary gene mutations may be introduced into mammals using the present methods. For example, the endogenous ungulate Ig J chain gene may be knocked out to prevent the potential antigenicity of the ungulate Ig J chain in the antibodies of the invention that are administered to humans. For the construction of the targeting vector, the cDNA sequence of the bovine Ig J chain region found in GenBank accession number U02301 may be used. This cDNA sequence may be used as a probe to isolate the genomic sequence of bovine Ig J chain from a BAC library such as RPC1-42 (BACPAC in Oakland, Calif.) or to isolate the genomic sequence of the J chain from any other ungulate. Additionally, the human J chain coding sequence may be introduced into the ungulates of the present invention for the functional expression of human IgA and IgM molecules. The cDNA sequence of human J chain is available as GenBank accession numbers AH002836, M12759, and M12378. This sequence may be inserted into an ungulate fetal fibroblast using standard methods, such as those described herein. For example, the human J chain nucleic acid in a HAC, YAC vector, BAC vector, cosmid vector, or knock-in construct may be integrated into an endogenous ungulate chromosome or maintained independently of endogenous ungulate chromosomes. The resulting transgenic ungulate cells may be used in the embryo cloning methods described herein to generate the desired ungulates that have a mutation that reduces or eliminates the expression of functional ungulate J chain and that contain a xenogenous nucleic acid that expresses human J chain.

In another example, if a non-human mammal, such as an ungulate, is genetically engineered to produce a human antibody, it may be desirable to also reduce or eliminate the expression of the ungulate α-(1,3)-galactosyltransferase gene, a gene that encodes an enzyme that produces the galactosyl(α1,3)galactose epitope. Glycosylated human antibodies modified by this carbohydrate epitope are sometimes inactivated or eliminated when administered as therapeutics to humans by recipient antibodies reactive with the epitope. To eliminate this possible immune response, the sequence of bovine α-(1,3)-galactosyltransferase gene may be used to design a knockout construct to inactive this gene. The bovine sequence (GenBank accession number J04989; Joziasse et al. (1989) J. Biol. Chem. 264: 14290-14297) or the porcine α-(1,3)-galactosyltransferase sequence (disclosed in U.S. Pat. Nos. 5,821,117 and 6,153,428) may be used to inactivate the genes in those species or to obtain the genomic α-(1,3)-galactosyltransferase sequence from a variety of other ungulates to generate mammals with reduced or eliminated expression of the epitope.

The ungulate PrP gene (encoding prion protein) may also be mutated or inactivated to reduce the potential risk of an infection such as bovine spongiform encephalopathy (BSE). Mutation of the bovine PrP gene is described below.

The additional mutations or the gene inactivation mentioned above may be incorporated into the ungulates of the present invention using various methodologies. Once a transgenic ungulate cell line is generated for each desired mutation, crossbreeding may be used to incorporate these additional mutations into the ungulates of the present invention. Alternatively, fetal fibroblast cells which have these additional mutations can be used as the starting material for the knockout of endogenous immunoglobulin genes and/or the introduction of xenogenous immunoglobulin genes. Also, as is described herein, fetal fibroblast cells having a knockout mutation in endogenous immunoglobulin genes and/or containing xenogenous immunoglobulin genes can be uses as a starting material for these additional mutations or inactivations.

Production of Cloned Non-human Mammals

We have previously disclosed a variety of methods for cloning mammals (e.g., ungulates, such as bovines) that may be used to clone mammals with one or more mutations in genes encoding IgM heavy chain (see, e.g., U.S. Patent Application Publication No. 2002-0046722 and PCT Publication No. WO02/051997). In some of these methods, a permeabilized cell is incubated with a reprogramming media (e.g., a cell extract) to allow the addition or removal of factors from the cell, and then the plasma membrane of the permeabilized cell is resealed to enclose the desired factors and restore the membrane integrity of the cell. Some of these methods also involve the condensation of a donor nucleus (e.g., an isolated nucleus or a nucleus within a donor cell) into a chromatin mass to allow the release of nuclear components such as transcription factors that may promote the transcription of genes that are undesirable for the development of the nuclear transplant embryo into a viable offspring. If desired, the steps of any of these methods may be repeated one or more times or different reprogramming methods may be performed sequentially to increase the extent of reprogramming, resulting in greater viability of the cloned fetuses.

Other methods for the production of cloned mammals (e.g., bovines) and cloned transgenic non-human mammals are known in the art, described, for example, in U.S. Pat. No. 5,995,577, assigned to University of Massachusetts, and in PCT Publication Nos. WO95/16670; WO96/07732; WO97/0669; and WO97/0668 (collectively, "the Roslin methods"). The Roslin methods differ from the University of Massachusetts techniques in that they use quiescent rather than proliferating donor cells. All of these patents are incorporated by reference herein in their entirety. These techniques are not limited to use for the production of transgenic bovines; the above techniques may be used for embryo cloning of other non-human mammals such as ungulates as well.

Following embryo cloning, production of desired animals may be affected either by mating the ungulates or by secondary gene targeting using the homologous targeting vector previously described.

Cre/Lox Excision of the Drug Resistance Marker

In one embodiment of the invention, the Cre/lox system is used to facilitate the efficient deletion of the marker following. Fetal fibroblasts carrying the targeting vector are transfected via electroporation with a Cre containing plasmid. A Cre plasmid that contains a GFPcre fusion gene (Gagneten et al. (1997) Nucleic Acids Res. 25:3326-3331) may be used. This allows the rapid selection of all clones that contain Cre protein. These cells are selected either by FACS sorting or by manual harvesting of green fluorescing cells via micromanipulation. Cells that are green are expected to carry actively transcribed Cre recombinase and hence delete the drug resistance marker. Cells selected for Cre expression are cloned and clones analyzed for the deletion of the drug resistance marker via PCR analysis. Those cells that are determined to have undergone excision are grown to small clones, split and one aliquot is tested in selective medium to ascertain with certainty that the drug resistance gene has been deleted. The other aliquot is used for the next round of targeted deletion.

Methods for Breeding Ungulates

In preferred embodiments of any of the above methods for generating ungulates or ungulate cells, an ungulate of the invention is mated with another ungulate to produce an embryo, fetus, or live offspring with two or more genetic modifications. Preferably, one or more cells are isolated from the embryo, fetus, or offspring, and one or more additional genetic modifications are introduced into the isolated cell(s).

Methods for Producing Antibodies

The invention also provides method for producing antibodies using an ungulate of the invention that expresses xenogenous antibodies (e.g., human antibodies). One such method involves administering one or more antigens of interest to an ungulate of the invention having nucleic acid encoding a xenogenous antibody gene locus. The nucleic acid segments in the gene locus undergo rearrangement resulting in the production of antibodies specific for the antigen. Antibodies are recovered from the ungulate. The antibodies may be monoclonal or polyclonal and are preferably reactive with an antigen of interest. Preferably, the antibodies are recovered from the serum or milk of the ungulate.

In a related aspect, the invention provides another method for producing antibodies that involves recovering xenogenous antibodies from an ungulate of the invention having nucleic acid encoding a xenogenous antibody gene locus. The nucleic acid segments in the gene locus undergo rearrangement resulting in the production of xenogenous antibodies. The antibodies may be monoclonal or polyclonal and are preferably reactive with an antigen of interest. Preferably, the antibodies are recovered from the serum or milk of the ungulate. Preferably, the ungulate antiserum or milk has polyclonal human immunoglobulins. Preferably, the antiserum or milk is from a bovine, ovine, porcine, or caprine. In another preferred embodiment, the immunoglobulins are directed against a desired antigen. In preferred embodiments, the antiserum is used as intravenous immunoglobulin (IVIG) for the treatment or prevention of disease in humans. In another preferred embodiment, an antigen of interest is administered to the ungulate, and immunoglobulins directed against the antigen are produced by the ungulate. Preferably, the nucleic acid segments in the xenogenous immunoglobulin gene locus rearrange, and xenogenous antibodies reactive with the antigen of interest are produced. Preferably, the antiserum and/or milk contains at least 2, 5, 10, 20, or 50 fold more xenogenous antibody than endogenous antibody, or contains no endogenous antibody. If desired, hybridomas and monoclonal antibodies can be produced using xenogenous B-cells derived from the above-described transgenic ungulates (for example, transgenic bovines). It is also contemplated that xenogenous antibodies (e.g., human antibodies) isolated from ungulates may be subsequently chemically modified so that they are covalently linked to a toxin, therapeutically active compound, enzyme, cytokine, radiolabel, fluorescent label, or affinity tag. If desired, the fluorescent or radiolabel may be used for imaging of the antibody in vitro or in vivo.

Ungulates and Donor Cells

Ungulates include members of the orders Perissodactyla and Artiodactyla, such as any member of the genus *Bos*. Other preferred ungulates include sheep, big-horn sheep, goats, buffalos, antelopes, oxen, horses, donkeys, mule, deer, elk, caribou, water buffalo, camels, llama, alpaca, pigs, and elephants.

Preferred cells for gene targeting include differentiated cells such as epithelial cells, neural cells, epidermal cells, keratinocytes, hematopoietic cells, melanocytes, chondrocytes, B-lymphocytes, T-lymphocytes, erythrocytes, macrophages, monocytes, fibroblasts, and muscle cells; and undifferentiated cells such as embryonic cells (e.g., stem cells and embryonic germ cells). In another preferred embodiment, the cell is from the female reproductive system, such as a mammary gland, ovarian cumulus, granulosa, or oviductal cell. Preferred cells also include those from any organ, such as the bladder, brain, esophagus, fallopian tube, heart, intestines, gallbladder, kidney, liver, lung, ovaries, pancreas, prostate, spinal cord, spleen, stomach, testes, thymus, thyroid, trachea, ureter, urethra, and uterus. Preferably, the donor cell, donor nucleus, donor chromatin mass, or reconstituted oocyte is not tetraploid.

Transgenic Ungulate Cells

In one aspect, the invention provides an ungulate cell (e.g., bovine cell) having a mutation (e.g., a mutation after the initial ATC codon, such as a mutation that is within 10, 20, 50, or 100 nucleotides of this codon) in one or both alleles of at least two genes encoding IgM heavy chain. Preferably, the mutations reduce or substantially eliminate the expression of functional IgM protein. In preferred embodiments, expression of functional or total IgM protein is decreased by at least 10, 20, 40, 60, 80, 90, 95, or 100%. The mutations may be hemizygous or homozygous. In some embodiments, the mutations include an insertion of a positive selection marker (e.g., an antibiotic resistance gene) into the nucleic acid. Preferably, the positive selection marker is operably linked to a xenogenous promoter. For ungulates or ungulate cells with an antibiotic resistance gene inserted into both alleles of a gene encoding IgM heavy chain, each allele may contain the same or a different antibiotic resistance gene. In a preferred embodiment, a negative selection marker (e.g., DT-A or Tk) is operably linked to a xenogenous promoter and is present in a vector used to disrupt an endogenous allele. The mutation may or may not include the deletion of one or more nucleotides (e.g., contiguous nucleotides) in the gene.

In preferred embodiments of the above aspect, the ungulate (e.g., bovine) or ungulate cell (e.g., bovine cell) has one or more transgenes and expresses an mRNA or protein (e.g., antibody) encoded by the transgene(s). Preferred ungulates contain naturally arranged segments of human chromosomes (e.g., human chromosomal fragments) or artificial chromosomes that comprise artificially engineered human chromosome fragments (i.e., the fragments may be rearranged relative to the human genome). In some embodiments, the xenogenous nucleic acid is contained within a chromosome fragment. The nucleic acid may be integrated into a chromosome of the ungulate or maintained in the ungulate cell independently from the host chromosome. In various embodiments, the nucleic acid is contained in a chromosome fragment, such as a ΔHAC, ΔΔHAC, or κHAC. In other embodiments, the xenogenous antibody is an antibody from another genus, such as a human antibody.

Preferred ungulates and ungulate cells have one or more nucleic acids having a xenogenous antibody gene locus (e.g., a nucleic acid encoding all or part of a xenogenous immunoglobulin (Ig) gene that undergoes rearrangement and expresses at least one xenogenous Ig molecule) in one or more B-cells. Preferably, the nucleic acid has unrearranged antibody light chain nucleic acid segments in which all of the nucleic acid segments encoding a V gene segment are separated from all of the nucleic acid segments encoding a J gene segment by one or more nucleotides. Other preferred nucleic acids have unrearranged antibody heavy chain nucleic acid segments in which either (i) all of the nucleic acid segments encoding a V gene segment are separated from all of the nucleic acid segments encoding a D gene segment by one or more nucleotides and/or (ii) all of the nucleic acid segments encoding a D gene segment are separated from all of the nucleic acid segments encoding a J gene segment by one or more nucleotides. Other preferred ungulates have one or more nucleic acids encoding all or part of a rearranged xenogenous immunoglobulin gene that expresses at least one xenogenous immunoglobulin.

In other preferred embodiments, the light chain and/or heavy chain of the xenogenous antibodies is encoded by a human nucleic acid. In preferred embodiments, the heavy chain is any class of heavy chain, such as μ, γ, δ, ε, or α, and the light chain is a lambda or kappa light chain. In other preferred embodiments, the nucleic acid encoding the xenogenous immunoglobulin chain or antibody is in its unrearranged form. In other preferred embodiments, more than one class of xenogenous antibody is produced by the ungulate. In various embodiments, more than one different xenogenous Ig or antibody is produced by the ungulate. The xenogenous antibody may be a polyclonal or monoclonal antibody.

Preferably, the ungulate also has a mutation in one or both alleles of an endogenous nucleic acid encoding prion protein, alpha-(1,3)-galactosyltransferase and/or J chain. Preferably, the mutation reduces or eliminates the expression of the endogenous alpha-(1,3)-galactosyltransferase enzyme, galactosyl($\alpha$1,3)galactose epitope, and/or J chain. Preferably, the ungulate produces human IgA or IgM molecules containing human J chain. Preferred ungulate cells (e.g., bovine cells) include somatic cells, such as fetal fibroblasts or B-cells.

The process of producing a transgenic ungulate of the invention involves the mutation (e.g., by homologous recombination) of one or both alleles of at least two IgM heavy chain genes (e.g., bovine Ig$\mu$U and Ig$\mu$AY genes). Gene mutation may be effected by homologous recombination. In a preferred embodiment, fetal fibroblasts are targeted in vitro using a suitable homologous recombination vector. The use of fetal fibroblasts is preferred over some other somatic cells as these cells are readily propagated and genetically manipulated in tissue culture. However, the use of fetal fibroblasts is not essential to the invention, and other cells may be substituted therefor with equivalent results. Suitable somatic cells include fibroblasts, epithelial cells, endothelial cells, neural cells, keratinocytes, hematopoietic cells, melanocytes, chondrocytes, lymphocytes (B-cells and T-cells), macrophages, monocytes, mononuclear cells, cardiac muscle cells, other muscle cells, granulosa cells, cumulus cells, placental cells, and epidermal cells.

Targeted gene mutation requires constructing a DNA construct having regions of homology to the targeted IgM heavy chain allele such that the construct upon integration into an IgM heavy chain allele in the ungulate genome disrupts the expression thereof. Exemplary vectors for carrying out such targeted mutation of bovine Ig$\mu$U and Ig$\mu$AY are described in the examples that follow. Methods for constructing vectors that provide for homologous recombination at other targeted sites are well known to those skilled in the art. Moreover, in the present instance, the construction of a suitable vector is within the level of skill in the art, given especially that the sequences of Ig$\mu$ genes from other ungulates (e.g., sheep and goats) are known (see below). In order to facilitate homologous recombination, the vectors used to effect homologous recombination and inactivation of the IgM gene, respectively, comprise portions of DNA that exhibit substantial sequence identity to the ungulate IgM heavy and Ig light chain genes. Preferably, these sequences possess at least 98% sequence identity, more preferably, at least 99% sequence identity, and still more preferably are isogenic with the targeted gene loci to facilitate homologous recombination and targeted deletion or inactivation.

Typically, the construct includes a marker gene that allows for selection of desired homologous recombinants, for example, fibroblasts, wherein the IgM heavy chain gene has been disrupted by homologous recombination. Exemplary marker genes include antibiotic resistance markers, drug resistance markers, and green fluorescent protein, among others.

One neomycin resistance construct was assembled as follows. A construct designated "pSTneoB" (Katoh et al. (1987) Cell Struct. Funct. 12:575; Japanese Collection of Research Biologicals (JCRB) deposit number: VE039) was designed to contain a neomycin resistance gene under the control of an SV40 promoter and TK enhancer upstream of the coding region. Downstream of the coding region is an SV40 terminator sequence. The neo cassette was excised from "pSTneoB" as a XhoI fragment. After the ends of the fragment were converted to blunt ends using standard molecular biology techniques, the blunt ended fragment was cloned into the EcoRV site in the vector, pBS246 (Gibco/Life Technologies). This site is flanked by loxP sites. The new construct, designated "pLoxP-STNeoR", was used to generate the mu knock-out DNA construct. The desired fragment of this construct is flanked by loxP sites and NotI sites, which were originally present in the pBS246 cloning vector. The desired NotI fragment, which contains loxP-neo-loxP, was used for replacement of the immunoglobulin mu constant region exons. The SV40 promoter operably linked to the neomycin resistance gene activates the transcription of the neomycin resistance gene, allowing cells in which the desired NotI fragment has replaced the mu constant region exons to be selected based on their resulting antibiotic resistance.

After a cell line is obtained in which an IgM heavy chain allele has been effectively disrupted, it is used as a donor cell to produce a cloned ungulate fetus (for example, a cloned bovine fetus) and eventually a fetus or animal wherein one of the IgM heavy alleles is disrupted. Thereafter, a second round of gene targeted mutation can be effected using somatic cells (e.g., fibroblasts) derived from the fetus or animal to produce cells in which a second IgM heavy chain allele is disrupted.

The following examples are meant to illustrate the invention. They are not meant to limit the invention in any way.

EXAMPLES

Example 1

Targeting of the Ig$\mu$U Gene

Figure 1:
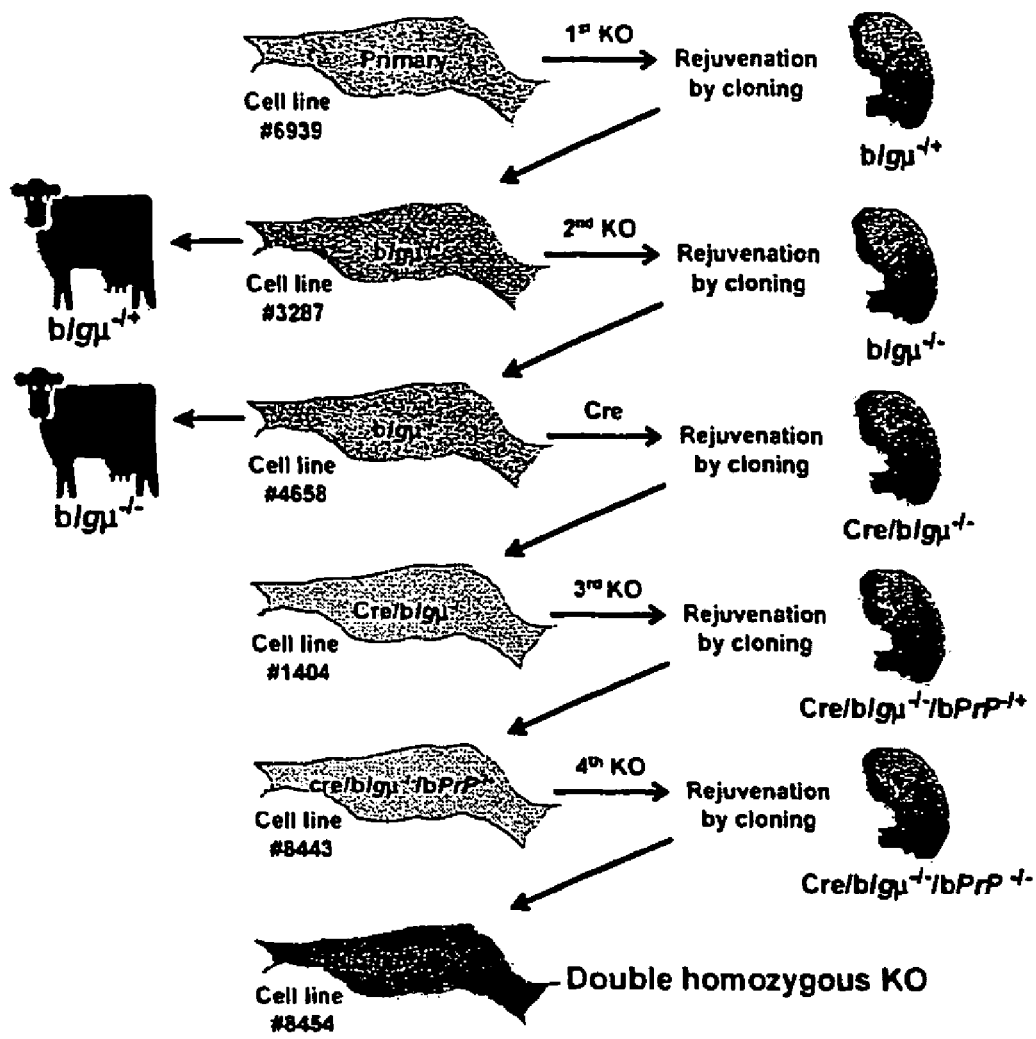
FIG. 1 is a schematic diagram depicting sequential gene targeting in bovine primary fibroblasts. Holstein fetal fibroblasts (#6939) were targeted, after which wells containing targeted cells were selected and cloned, using a chromatin transfer system to generate IgµU$^{-/+}$ fetuses. The IgµU$^{-/+}$ cell line (#3287) was then used for the production of calves and for targeting the second allele of IgµU. Once again, cells were selected and regenerated by production of fetuses. Fetuses were harvested for the production of IgµU–/– cell lines, gene expression analysis, and production of calves. An IgµU$^{-/-}$ cell line (#4658) was transfected with a Cre-recombinase expression plasmid to remove both the neo and puro genes simultaneously, followed by a third round of chromatin transfer to generate cloned fetuses and cell lines, in which both neo and puro selection marker genes were excised. One Cre-excised IgµU$^{-/-}$ fibroblast cell line (#1404) was used for a third round of gene targeting to produce triple targeted, Cre/IgµU$^{-/-}$/PrP$^{-/+}$ fetuses and cell lines. One cell line (#8334) was subjected to the fourth round of gene targeting to produce double homozygous KO (cre/IgµU$^{-/-}$/PrP$^{-/-}$) fetuses and cell lines and for the evaluation of PrP gene expression.
Figure 2:
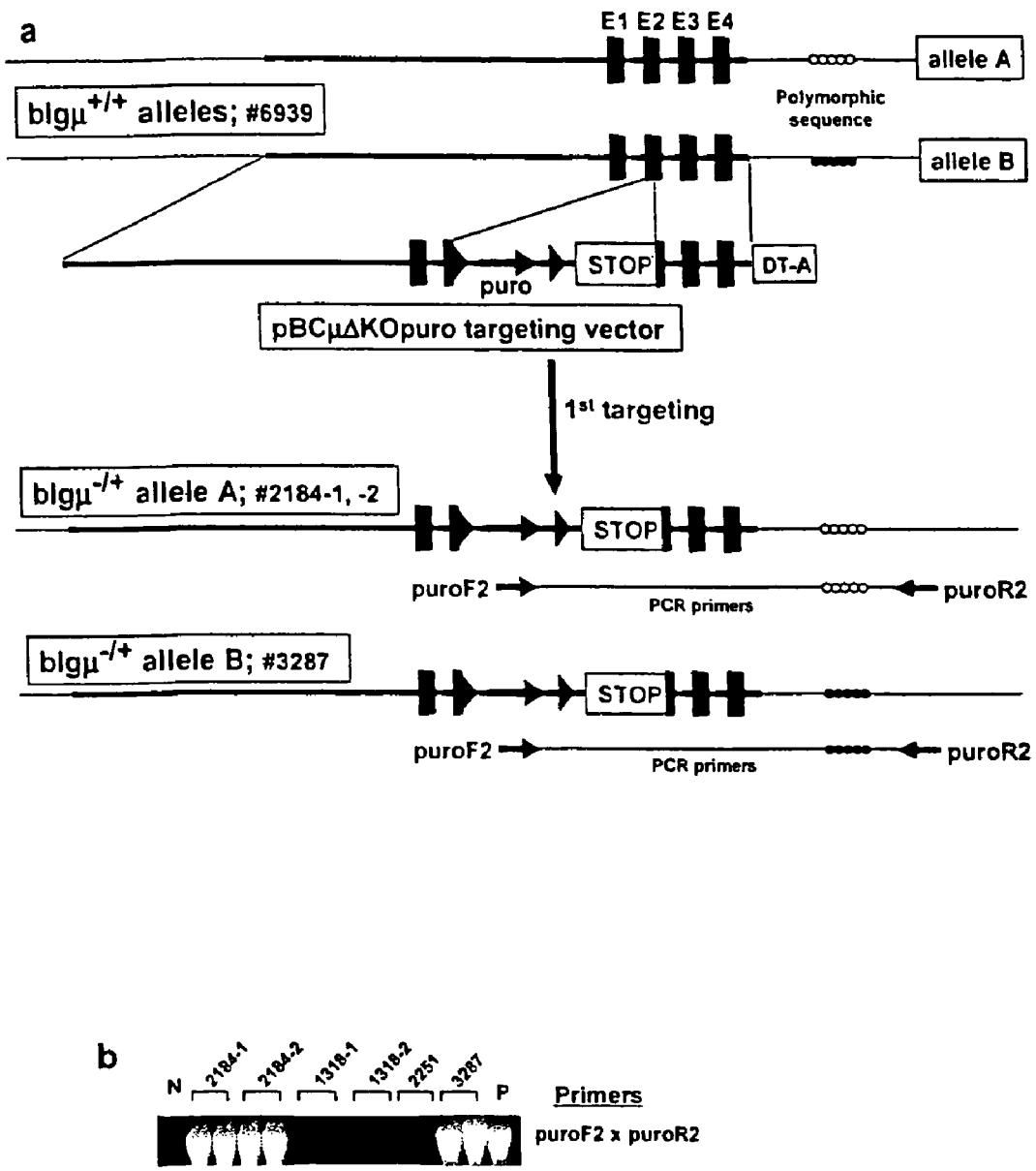
FIG. 2A is a schematic diagram representing the structure of IgµU constant region locus in #6939, the puro vector used for the first round of targeting, and the genomic PCR assay used for the targeting event. The targeting vector was composed of a 5' homologous arm (7.2 kb), a 3' homologous arm (2.0 kb), STOP cassette containing transcriptional and translational stop sequences, DT-A (diphtheria toxin A gene), and a floxed puro gene. The vector was designed to insert the knockout cassette into exon 2 of the IgµU constant region locus. In #6939 fibroblasts, polymorphic sequences were found to distinguish allele A and allele B, as indicated. Primer pairs, puroF2×puroR2 were used to identify the first targeting event. PCR and sequencing product showed that the vector was integrated into allele B in cell line #3287 and in allele A in #2184-1 and 2 cell lines, based on the polymorphic sequences presented in the PCR product.
FIG. 2B is a photograph representing the identification of IgµU$^{-/+}$ fetuses by genomic PCR with puroF2×puroR2 primers. N is a negative control (mixture of the 1st KO vector and #6939 genomic DNA) and P is a positive control (mixture of about $10^4$ copies/µl of plasmid DNA covering puroF2–puroR2 region and #6939 genomic DNA). Cell lines #2184-1, #2184-2 and #3287 were IgµU$^{-/+}$.
FIG. 2C is a photograph representing the genotyping of IgµU$^{-/+}$ calves by genomic PCR with puroF2×puroR2 primers. N is a negative control (mixture of the 1st KO vector and #6939 genomic DNA) and P is a positive control (mixture of about $10^4$ copies/µl of plasmid DNA covering puroF2–puroR2 region and #6939 genomic DNA). Out of 13 IgµU$^{-/+}$ calves born (also shown in FIG. 2C), five were genotyped and found to be positive to the first targeting event.
Figure 2:
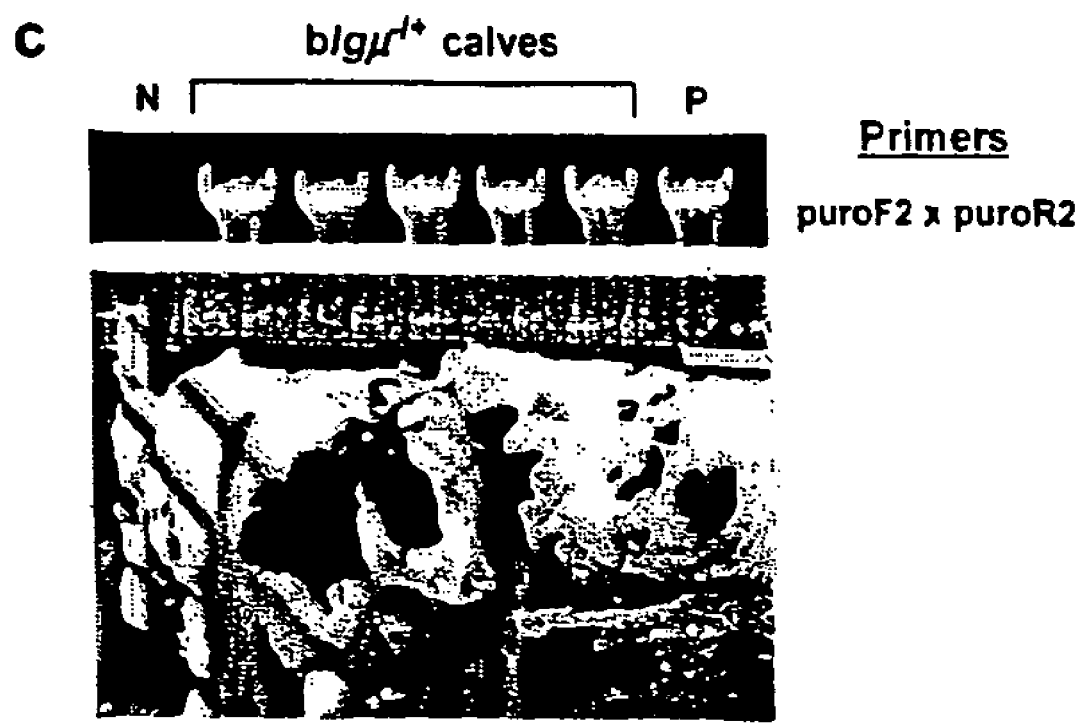

We have developed a broadly applicable and rapid method for generating multiple gene targeting events. As discussed above, sequential application of a highly efficient targeting system and rejuvenation of cell lines by production of cloned fetuses (FIG. 1) were employed. We chose to target the Ig$\mu$U gene, which is transcriptionally silent in fibroblasts. This gene was characterized in a male Holstein fetal fibroblast cell line (#6939) to identify a polymorphic marker DNA sequence, outside the KO vector sequence, which could be used to distinguish the two alleles (FIG. 2A; allele A and allele B as indicated). Fetal fibroblasts from cell line #6939 were electroporated with the first KO vector (pBC$\mu\Delta$KOpuro; FIG. 2A) to produce 446 wells resistant to puromycin. Wells were split on day 14 and half of the cells were used for screening by PCR (primer pairs; puroF2×puroR2, FIG. 2A) to identify wells containing correctly targeted cells. Initially, six wells were positive by PCR. To exclude false positive wells, all of the PCR products were subjected to bi-directional sequencing analysis with the puroF2 and puroR2 primers. Two wells (0.45%; #147, #384) were identified as being targeted correctly. Based on polymorphic differences identified by sequence analysis, the KO vector was integrated into allele A in well #384 and into allele B in well #147. The remaining cells from the two wells were used for embryonic cloning to generate fetuses and to rejuvenate the cell lines. Pregnancy rate at 40 days of gestation was 50% (15/30; two embryos per recipient) and at 60 days of gestation, six fetuses were collected and fibroblasts were re-established.

Three of six fetuses (#2184-1, #2184-2 and #3287) were heterozygous KOs (Ig$\mu$U−/+; FIG. 2B) as confirmed by PCR (primer pairs; puroF2×puroR2) and sequence analysis.

Non-targeted fetuses likely resulted from non-targeted cells that co-existed with the targeted cells in the wells. Both #2184-1 and #2184-2 were derived from well #384 where the KO vector was integrated into allele A, and fetus #3287 was from well #147 where the KO vector was integrated into allele B. Cloned IgμU−/+ embryos produced from all three regenerated cell lines were transferred to 153 recipients to produce 13 (8%) healthy IgμU−/+ calves, confirmed by PCR (FIG. 2C) and sequence analysis.

All three IgμU−/+cell lines (#2184-1 and #2184-2, targeted in allele A; #3287, targeted in allele B) were used for targeting with the second KO vector (pBCμΔKOneo; FIG. 3A) in which the short homologous arm was replaced with a PCR-derived sequence amplified directly from allele A of the #6939 cell line. In #2184-1 and #2184-2 cell lines, a total of 1,211 wells, resistant to G418, were screened by PCR (primer pairs; neoF3×neoR3; FIG. 3A) followed by sequence analysis. Five wells were positive and, in two, the vector was integrated into the intact allele B, producing homozygous KO (IgμU$^{-/-}$) cells, and in three wells the targeting vector in allele A was replaced. In #3287 cell line, 569 wells, resistant to G418, were screened by PCR (primer pairs; neoF3×neoR3; FIG. 3A) followed by sequence analysis. Seven wells were positive and, in six, the vector was integrated into the intact allele A producing IgμU$^{-/-}$ cells and, in one well, the targeting vector in allele B was replaced. Overall, the vector had a bias of 3:1 for allele A and was more efficient for homozygous targeting when used with cell line #3287 (6/569, 1.1% compared to 2/1211, 0.17%), as expected.

Two IgμU$^{-/-}$ wells (#76, #91), derived from cell line #3287, were selected for embryonic cloning to generate fetuses and rejuvenate the cell lines. Overall, the pregnancy rate for IgμU$^{-/-}$ fetuses at 40 to 50 days of gestation was 45% (40/89). At 45 days of gestation, five fetuses derived from well #76 and 15 fetuses from well #91 were collected and evaluated. All five from well #76 (FIG. 3B) and three out of the 15 from well #91 were positive as determined by PCR (primer pairs; puroF2×puroR2 and neoF3×neoR3). PCR results were confirmed by sequence analyses and negative PCR (primer pairs; bCμf×bCμr; FIG. 3A) for the wild-type alleles (FIG. 3B). Confirmation of a functional KO was obtained by generation of 90 day fetuses from regenerated IgμU$^{-/-}$ fibroblasts and evaluation of IgμU gene expression in spleen cells. The absence of expression was confirmed by RT-PCR (primers pairs; bCμf×bCμr, FIG. 3C). Cloned embryos were made from five IgμU$^{-/-}$ cell lines and were transferred to recipients for development to term.

Two calves from this group were born recently and were confirmed to be IgμU$^{-/-}$ by PCR (FIG. 3D) and sequence analysis, verifying that sequential gene targeting and successive rounds of cell rejuvenation are compatible with full term development of healthy calves.

Example 2

Removal of Selection Markers Using the Cre/LoxP System

Sequential targeting requires a strategy for antibiotic selection of a newly integrated targeting vector in a cell line that already contains one or multiple antibiotic selection markers. The simplest approach is to use a different selection marker gene for each targeting event. This approach however, limits the number of targeting events that may be performed in a cell line. Another approach is to remove the selection markers using a Cre-loxP recombination system, as has been done in murine embryonic stem cells (Abuin and Bradley (1996) Mol. Cell Biol. 16:1851-1856). In our regenerated IgμU targeted fibroblasts, the selection marker genes were not expressed, likely because the IgμU locus is silent in fibroblasts. Although selection marker removal was not necessary for further targeting in our IgμU$^{-/-}$ fibroblasts, we evaluated the possibility of removing the selection markers by transfection with a Cre recombinase expression plasmid. Because the intention was for transient expression of Cre recombinase, a closed circular plasmid was used and antibiotic selection was restricted to the first three days of culture. Bovine IgμU$^{-/-}$ cell line #4658 was used for transfection and 24 selected wells were evaluated by PCR for excision of the antibiotic selection genes from the targeted alleles (FIG. 4A). Multiple wells showed evidence of excision of both puro and neo genes and one was chosen for fetal cloning and regeneration of cell lines. Pregnancy rate at 40 to 50 days of gestation was 35% (21/60).

Five fetuses were recovered and all had both selection markers removed (FIG. 4B). The Cre recombinase plasmid integrated into the genome in all fetuses, except #1404. These results indicate that Cre-loxP recombination can be used to remove selection markers in somatic cells. Routine use in this system will require improvements to reduce integration frequency of Cre-expression plasmid.

Example 3

Targeting of the PrP Gene

To evaluate the possibility of sequentially targeting a second gene, Cre-excised IgμU$^{-/-}$ (Cre/IgμU$^{-/-}$) fibroblasts (cell line #1404) were subjected to a third round of targeting to disrupt the PrP gene. This gene was first characterized to identify a polymorphic sequence, outside the KO vector sequence, to distinguish the two alleles (FIG. 5A; allele C and allele D as indicated). Cells were transfected with the third KO vector (pBPrP(H)KOneo, FIG. 5A) and 203 G418-resistant wells were screened by PCR.

Thirteen (6.4%) wells with cells showing a heterozygous KO PrP in Cre/IgμU$^{-/-}$ background (Cre/IgμU$^{-/-}$/PrP$^{-/+}$) were identified (primer pairs; neoF7×neoR7; FIG. 5A). Sequence analysis showed that the third KO vector was integrated into allele C of the PrP gene in all the positive wells. Some wells were used for cloning to generate 28 pregnancies at 45 days of gestation (71%; Table 1). Five fetuses were collected and all were positive for targeting at allele C of the PrP gene as indicated by PCR (FIG. 5B; primer pairs; neoF7×neoR7) and sequencing analyses.

TABLE 1

Embryo development, fetuses and calves with modified cells

| Type of modification | No of cloned embryos produced (%) | No of recipients implanted | Pregnant at 40-45 d (%) | No of positive fetuses/number collected (%) | No of calves born (%) |
|---|---|---|---|---|---|
| IgμU$^{-/+}$ | 55/422 (19) | 30 | 15 (50) | 3/9 (33) | — |
| IgμU$^{-/+}$ | 153/3305 (15) | 153 | 99 (65) | — | 13 (8) |
| IgμU$^{-/-}$ | 438/2379 (26) | 89 | 40 (45) | 20/40 (50) | — |

TABLE 1-continued

Embryo development, fetuses and calves with modified cells

| Type of modification | No of cloned embryos produced (%) | No of recipients implanted | Pregnant at 40-45 d (%) | No of positive fetuses/number collected (%) | No of calves born (%) |
|---|---|---|---|---|---|
| IgµU$^{-/-}$ | 333/4350 (11) | 171 | 107 (63) | — | 8 (6) |
| IgµU$^{-/+}$ Prp $^{-/+}$ | 112/739 (22) | 39 | 28 (71) | 5/19 (26) | — |
| IgµU$^{-/+}$ Prp $^{-/-}$ | 240/1673 (20) | 38 | 26 (68) | 33/33 (100) | — |

TABLE 2

Triple Gene Targeting

| Cell line (IgµU−/−) | No. of colonies screened | No. of triple targeted colonies (IgµU−/−/PrP−/+) | Frequency of triple targeting |
|---|---|---|---|
| #1404 | 203 | 13 | 6.4% |
| #4658 | 181 | 11 | 6.0% |
| #5112 | 187 | 10 | 5.3% |

No amplification was detected following negative IgµU PCR, as expected (FIG. 4B; primer pairs; bCµfxbCµr). As shown in Table 2, targeting efficiency for PrP, a gene that is active in bovine fibroblasts, was substantially higher than for IgµU (6.4% vs. 0.63%, respectively), a gene that is not expressed in fibroblast cells.

To examine the feasibility of quadruple targeting to produce double homozygous KO fetuses and cell lines, the triple targeted cell line (#8443, Cre/IgµU$^{-/-}$/PrP$^{-/+}$) was transfected with a fourth KO vector for the remaining allele of the PrP gene. The vector was constructed by replacing the neo gene with a puro gene (pBPrP(H)KOpuro, FIG. 6A) in the PrP targeting vector used for the first allele. As a result of selection and PCR screening (primer pairs; puroF14× puroR14, FIG. 6A), 17 (5.2%) wells were found to contain cells showing homozygous KO PrP in Cre/IgµU$^{-/-}$ background (Cre/IgµU$^{-/-}$/PrP$^{-/-}$). Sequence analysis indicated that the fourth KO vector was integrated into allele D of the PrP gene in all positive wells, except one, in which the targeted sequence in allele C was replaced. Cells from Cre/IgµU$^{-/-}$/PrP$^{-/-}$ positive wells were used for cloning to produce fetuses and at 45 days of gestation with a pregnancy rate of 71% (28/39). All 18 fetuses that were collected were Cre/IgµU$^{-/-}$/PrP$^{-/-}$ as indicated by positive PCR analysis using the targeting event-specific primer pairs, puroF14×puroR14 and neoF7×neoR7 (FIG. 6B). Sequencing analyses confirmed integration of the third (neo) and fourth (puro) PrP targeting vectors into alleles C and D, respectively. Furthermore, we performed a negative PCR analysis to confirm the absence of wild-type PrP alleles (primer pairs; BPrPex3F× BPrPex3R, FIG. 6B) and IgµU alleles (primer pairs; bCµfx bCµr) and, as expected, all four KOs were confirmed. To evaluate PrP mRNA expression, fibroblasts from a IgµU$^{-/-}$, a IgµU$^{-/-}$/PrP$^{-/+}$ and Cre/IgµU$^{-/-}$/PrP$^{-/-}$ cell lines were examined by RT-PCR. Functional disruption of PrP gene expression was confirmed (FIG. 6C). Table 3 shows the frequency of quadruple targeting in the Cre/IgµU$^{-/-}$/PrP$^{-/-}$ cell line #8018.

TABLE 3

Quadruple Gene Targeting

| Cell line (IgµU−/−/PrP−/+) | No. of colonies screened | No. of quadruple targeted colonies (IgµU−/−/PrP−/−) | Frequency of quadruple targeting |
|---|---|---|---|
| #8018 | 325 | 3 | 0.92% |

Our results indicate that multiple rounds of gene targeting, both for active and silent genes, are readily accomplished in somatic cells using a cell rejuvenation approach. The system proved effective for targeting both transcriptionally silent and active genes, demonstrating broad application, and was compatible with development of healthy calves through at least two rounds of targeting. Furthermore, there is no indication that additional rounds of targeting compromised development of cloned embryos.

Methods

The results described in Examples 1-3 were obtained using the following methods.

Construction of KO Vectors

A bovine genomic fragment around exon 2 of the IgµU constant region locus was obtained from non-isogenic Holstein genomic library by probing with a $^{32}$P-labeled PCR fragment amplified with primer pair: 5'-TGGTCACTC-CAAGT GAGTCG-3' (SEQ ID NO: 1) and 5'-TGGAGT-GAAATCAGGTGAAGG-3' (SEQ ID NO: 2). One genomic clone was, analyzed further by restriction mapping. The 7.2 kb of BglII-XhoI genomic fragment (5' homologous arm) and 2.0 kb of BamHI-BglII fragment (3' homologous arm) around the exon 2 were subcloned into pBluescript II SK(−) (Stratagene), and then puro, STOP cassettes (pBS302, Stratagene) and DT-A (diphtheria toxin A) genes were inserted (pBCµΔ-Kopuro). For construction of the second targeting vector, genomic PCR was performed from #6939 by using primer pair: 5'-GCAATAGCAAGTCCAGC CTCATCTG-3' (SEQ ID NO: 3) and 5'-CATCCTGTCTCTGGTGGTTTGAGG TC-3' (SEQ ID NO: 4). After digestion with BamHI-BglII, the fragment replaced the 3' short arm of the pBCµΔKOpuro vector. By sequencing, the BamHI-BglII fragment was confirmed to be amplified from "allele A".

The puro gene was replaced with a neo gene (pBCµΔKO-neo vector). Bovine genomic fragment around exon 3 of the PrP locus was obtained by screening of the same Holstein genomic λ phage library with a $^{32}$P-labeled DNA fragment amplified by PCR primer pair: 5'-GATTGAATGGTCTC-CAGGATG CC-3' (SEQ ID NO: 5) and 5'-GACAAGCT-TAATATCCGCAGG-3' (SEQ ID NO: 6). One genomic clone was analyzed further by restriction mapping. The 8.3 kb of Bam HI genomic fragment (3' homologous arm) and 1.2 kb of BamHI-BglII fragment (5' homologous arm) containing exon 3 were subcloned into pBluescript II SK(−), and then both neo and STOP cassettes were inserted at the BamHI site, which is behind the initial ATG codon. The DT-A gene was also subcloned (pBPrP(H)KOneo vector). Similarly, another KO vector containing the puro gene was constructed (pBPrP(H)KOpuro vector).

Cell Culture and Transfection

Holstein fetal male fibroblasts were cultured as previously described (Kuroiwa et al. supra) and electroporated with 30 µg of each targeting vector at 550 V and 50 µF by using a GenePulser II (Bio-rad). After 48 hours, the cells were selected under 500 µg/ml of G418 or 1 µg/ml of puromycin for two weeks and the drug-resistant colonies were picked and transferred to replica plates; one for genomic DNA extraction (24-well plates) and the other for embryonic cloning (48-well plates).

Genomic PCR Analyses

From the replica 24-well plates, fetus or ear biopsy genomic DNA from calves was extracted using a Puregene DNA extraction kit (GentraSystem). To identify each homologous recombination event that occurred at IgµU targeting, puroF2 (5'-GAGCTGCAAGAACTCTTCCT-CACGC-3', SEQ ID NO: 7), puroR2 (5'-ATGTACCTC-CCAGCTGAGACAGAGGG-3', SEQ ID NO: 8), neoF3 (5'-TTTGGTCCTGTAGTTTGCTAACACACCC-3', SEQ ID NO: 9) and neoR3 (5'-GGATCAGTGCCTATCACTCCAG-GTTG-3', SEQ ID NO: 10) primer pairs were used. PCR was performed in 30 cycles comprising 98° C.-10 s, 68° C.-8 min. For negative PCR, BCµf (5'-TGGTCACTCCAAGT-GAGTCG-3', SEQ ID NO: 11) and BCµr (5'-TGGAGT-GAAATCAGGTGAAGG-3', SEQ ID NO: 12) were used in 40 cycles of PCR composed of 98° C.-10 s, 62° C.-30 s, 72° C.-1 min. In the case of the PrP locus, neoF7 (5'-TGTCAAA-GAGACACTCCTCATTTGTCT TCC-3', SEQ ID NO: 13), neoR7 (5'-TCATAGCCGAATAGCCTCTCCACCC-3', SEQ ID NO: 14), puroF14 (5'-TTGCTCCACCTTCCGTCTTCT-GTC-3', SEQ ID NO: 15) and puroR14 (5'-GTTGGCGC-CTACCGGTGGATGTTTG-3', SEQ ID NO: 16) primer pairs were used. PCR was performed in 30 cycles comprising 98° C.-10 s, 68° C.-5 min. For negative PCR, BPrPexF (5'-CCA-CATAGGCAGTTG GATCC-3', SEQ ID NO: 17) and BPrPexR (5'-ATAAGAGGCCTGCTCATG GC-3', SEQ ID NO: 18) primer pairs were used in the 40 cycles of PCR composed of 98C-10 s, 62C-30 s, 72C-1 min. To detect the Cre-mediated excision, PCR was carried out with CreExF (5'-CAATAGCAAGTCCAGCCTCATCTGC-3', SEQ ID NO: 19) and CreExR (5'-GTGGTTTCTTCGGTGGAAA-CAACG-3', SEQ ID NO: 20) primer pair in 40 cycles of PCR composed of 98° C.-10 s, 68° C.-7 min. All the PCR products were run on 0.8% agarose gels.

Sequencing of PCR Products

To confirm whether homologous recombination correctly occurred at each targeting step, the PCR products amplified above were sequenced. The PCR products were purified through CHROMA SPIN-TE400 column (BD Biosciences Clontech) and sent to ACGT Inc. (Wheeling, Ill.) to sequence. Sequence was bi-directionally done both with forward and reverse primers which were used for PCR. The allele into which each KO vector was integrated was determined by polymorphisms in the sequence of the PCR products.

Permeabilized Cell Transfer

Cloned fetuses and calves were produced using a permeabilized cell transfer procedure as described previously (Sullivan et al. (2004) Biol. Reprod. 70:146-153). In vitro matured oocytes were enucleated at 20 h post maturation. Correctly targeted clones were permeabilized by incubation of about 50,000-100,000 cells in suspension with 31.2 U Streptolysin O (SLO; Sigma) in 100 µl HBSS for 30 min in a 37° C. H$_2$O bath.

Permeabilized cells were sedimented, washed and incubated with 40 µl mitotic extract containing an ATP generating system (1 mM ATP, 10 mM creatine phosphate and 25 µg/ml creatine kinase) for 30 min at 38° C. At the end of the incubation, the reaction mix was diluted, sedimented and washed.

These cells were fused to enucleated oocytes, activated at 28 h post maturation with 5 µM calcium ionophore for 4 min followed by 10 µg/ml cycloheximide and 2.5 µg/ml cytochalasin D for 5 h. After activation, embryos were washed and co-cultured with mouse fetal fibroblasts to the blastocyst stage in vitro. Grade 1 and 2 blastocysts were selected and transferred into synchronized recipients. All animal work was done following a protocol approved by the Transova Genetics Institutional Animal Care and Use Committee.

RT-PCR

RNA was extracted from spleen of wild-type (#6939) and IgµU−/− fetuses using an RNeasy mini kit (Qiagen) and first strand cDNA synthesis was done using the superscript first strand synthesis system for RT-PCR (Invitrogen). PCR was done using BCµf (5'-TGGTCACTCCAAGTGAGTCG-3', SEQ ID NO: 21) and BCµr (5'-TGGAGTGAAATCAGGT-GAAGG-3', SEQ ID NO: 22) primers in 40 cycles of PCR composed of 98° C.-10 s, 62° C.-30 s, 72° C., 1 min. RNA was also extracted from #4658 (IgµU$^{-/-}$), #8443 (IgµU$^{-/-}$/PrP$^{-/+}$) and double homozygous KO (IgµU$^{-/-}$/PrP$^{-/-}$) fibroblasts and first strand cDNA synthesis was done as above. PCR was done by using PrPmF3 (5'-CAAAACCTGGAGGAG-GATGG-3', SEQ ID NO: 23) and PrPmR3 (5'-ATAAGAG-GCCTGCTCATGGC-3', SEQ ID NO: 24) primers in 40 cycles of 98° C.-10 s, 62° C.-30 s, 72° C.-1 min. For detection of bovine α-actin mRNA expression, bBAF (5'-ACATCCG-CAAGGACCTCT AC-3', SEQ ID NO: 25) and bBAR (5'-AACCGACTGCTGTCACCTTC-3', SEQ ID NO: 26) primers were used in the same PCR condition. To exclude the possibility of genomic DNA contamination, another RT-PCR was performed without reverse-transcriptase. The PCR products were ran on 0.8% agarose gel.

Example 4

Identification of IgµAY

During our analysis of IgµU$^{-/-}$ fibroblasts we identified expression of a transcript that could be detectable by primers designed to amplify IgµU$^{-/-}$. To determine the identity of this transcript, total RNA was extracted by using RNeasy Mini kit (QIAGEN) from spleen of IgµU$^{-/-}$ fetuses collected at 90 days of gestation. One microliter of total RNA was subjected to first-strand cDNA synthesis (SuperScript First-Strand Synthesis System for RT-PCR, Invitrogen), followed by RT-PCR, which was carried out as below. The primer pair used was 5'-TGGTCACTCCAAGTGAGTCG-3' (BCµf; SEQ ID NO: 27) and 5'-TGGAGTGAAATCAG GTGAAGG-3' (BCµr; SEQ ID NO: 28). The PCR reaction mixtures contained 32.5 µl water, 5 µl of 10× Ex Taq buffer (TAKARA), 8 µl of dNTP mixture, 10 µmol forward primer, 10 µmol of reverse primer, 2 µl of the first-strand cDNA, and 0.5 µl of Ex Taq (TAKARA). Thirty five cycles of PCR were performed by incubating the reaction mixtures at the following conditions: 85° C. for three minutes, 94° C. for one minute, 98° C. for 10 seconds, 62° C. for 30 seconds and 72° C. for 1 minute. After PCR, the reaction mixtures were analyzed by electrophoresis. There were no positive PCR products in the IgµU$^{-/-}$ fetuses. However, when another primer pair 5'-TCTCTGGT- GACGGC AATAGC-3' (BCµf2; SEQ ID NO: 30) and 5'-CT-TCGTGAGGAAGATGTC GG-3' (BCµr2; SEQ ID NO: 31) was used for RT-PCR, a positive PCR product was detected in the IgµU$^{-/-}$ fetuses (FIG. 10). To determine the source of this discrepancy, each primer sequence was analyzed by BLAST. The results indicated that the BCµf primer sequence was specific to the bovine Igµsequence corresponding to U63637.2. On the other hand, BCµf2 and BCµr2 sequences matched U63637.2 and another sequence AY230207, which had been previously reported as being a polymorphic variant of U63637.2. We conclude that U63637.2 and AY230207 are not polymorphic variants of the same gene, but rather are different Igµ genes in bovine. We refer to U63637.2 Igµ gene as IgµU, and to AY230207 as IgµAY.

To determine whether both IgµAY and IgµU genes are expressed following VDJ rearrangement, mRNA was similarly extracted from spleens of #6939 (original cell line)-derived and IgµU$^{-/-}$ fetuses. RT-PCR was performed using 5'-CCCTCCTCTTTGTGCTGTCA-3' (BL17; SEQ ID NO: 32) and 5'-GTTCA GGCCATCATAGGAGG-3' (mBCµ-R2; SEQ ID NO: 33) in thirty five cycles composed of conditions: 85° C. for three minutes, 94° C. for one minute, 98° C. for 10 seconds, 62° C. for 30 seconds and 72° C. for 1 minute. The PCR products were purified through CHROMA SPIN TE-100 column (BD) and sent to ACGT Inc. to directly sequence them with mBCµ-R2 primer. According to sequence peak chart, IgµAY transcript was mainly expressed, in addition to a very small amount of that of IgµU in #6939 fetuses, revealing that both IgµAY and IgµU underwent VDJ rearrangement to be expressed and that both of them are functional in terms of transcription (FIG. 11). However, in the IgµU KO fetuses, it is IgµAY that is expressed following VDJ rearrangement (FIG. 11).

Example 5

Mutation of IgµAY

IgµAY KO vectors were generated as follows. To isolate genomic DNA around exon 2 of the IgµAY gene, a DNA probe was amplified by PCR using 5'-TCTCTGGTGACG-GCAATAGC-3' (SEQ ID NO: 34) and 5'-CTTCGTGAGGA AGATGTCGG-3' (SEQ ID NO: 35) (BCµ-f2 and BCµ-r2). Using this probe, a bovine (Holstein) genomic λ phage library derived from #4658 IgµU homozygous KO cell line was screened, and 83 positive λ phage clones were identified. These clones should contain both alleles of intact IgµAY gene and both alleles of targeted IgµU gene. To distinguish intact IgµAY clones from the targeted IgµU clones, λDNA isolated from each clone was subjected to PCR using primer pair BCµ-f2 and BCµ-r2. In the case of clones containing the targeted IgµU gene, the PCR product cannot be amplified because of presence of the KO cassette integrated at exon 2. On the other hand, the PCR product can be amplified from intact IgµAY locus; clones producing the PCR product should be ones including intact IgµAY gene, but clones not producing the PCR products should be ones including the targeted IgµU gene. Out of 83 λ phage clones, 26 produced the PCR products and these were confirmed to be clones containing intact IgµAY gene by sequence (primer AYU-F2; 5'-GGCT-GACTCCCTACCTCCCCTACAC-3' (SEQ ID NO: 36). At least other 10 clones that did not produce the PCR products proved to contain the targeted IgµU gene, confirmed by sequence (primer AYU-F2). The foregoing demonstrated that there are at least two Igµ genes in bovine, and that one gene (which we refer to as IgµU) is disrupted in our KO cell line (#4658) but the other gene (IgµAY) is still intact (FIG. 12).

To distinguish both alleles of IgµAY, we sequenced all the λ phage DNA using primer AYU5' (5'-CGGAGCCCCTG-GAGATGAGC-3') (SEQ ID NO: 37). According to this sequencing, we found polymorphic sequences to differentiate the alleles of IgµAY gene, which we named the AY allele and ay allele (FIG. 13). Out of the 26 clones, 5 clones contained AY allele and 21 clones contained ay allele. To construct AY- or ay-specific KO vectors, we chose #37 clone for AY and #49 for ay. Each of #37 and #49 was analyzed further by restriction mapping. The 9 kilobases of SalI-BamHI genomic fragment containing all of the CµAY exons was subcloned into pBluescript II SK(−) in which the KpnI site is already replaced with an SrfI site. Then, both the bsr and STOP cassettes were inserted at the BglII site, which is just located in exon 2 of Cµ. Both bsr and the STOP cassettes were in a sense strand-orientation related to the IgµAY gene. A diphtheria toxin gene (DT-A, Gibco) was then added to the NotI site in the pBluescript II SK(−). DT-A was inserted in forward orientation relative to the bsr gene in the targeting cassette to kill cells in which the targeting cassette was randomly integrated in the genome (pBCgAYKObsr vector; FIG. 14). Similarly, another KO vector for ay allele containing hyg gene was constructed (pBCµayKOhyg vector; FIG. 14).

Transfection of IgµU homozygous KO cell lines with IgµAY KO vectors was performed using the following standard electroporation protocol. The medium used to culture the bovine fetal fibroblasts contained 500 ml alpha MEM (Gibco, 12561-049), 50 ml fetal calf serum (Hy-Clone #ABL13080), 5 ml penicillin-streptomycin (SIGMA), and 1 ml 2-mercaptoethanol (Gibco/BRL #21985-023). On the day prior to transfection, cells were seeded on a T175 tissue culture flask with a confluency of 80-100%, as determined by microscopic examination. On the day of transfection, about 1 bovine fibroblasts cells were trypsinized and washed once with alpha-MEM medium. After resuspension of the cells in 800 µl of alpha-MEM, 30 µg of the SrfI-digested KO vector (pBCµAYKObsr vector) dissolved in HEPES buffer saline (HBS) containing 1 mM spermidine was added to the cell suspension and mixed well by pipetting. The cell-DNA suspension was transferred into an electroporation cuvette and electroporated at 550 V and 50 µF. After that, the electroporated cells were plated onto thirty 48-well plates with the alpha-MEM medium supplemented with the serum. After a 48 hour-culture, the medium was replaced with medium containing 10 µg/ml of blasticidine, and the cells were cultured for 2-3 weeks to select blasticidine resistant cells. After selection, all colonies which reached close to 100% confluency were divided into two replica plates (24-well and 48-well plates): one for genomic DNA extraction, and the other plate for embryo cloning. Genomic DNA was extracted from the colonies to screen for the desired homologous recombination events by PCR.

Genomic DNA was independently extracted from each 24-well using the PUREGENE DNA isolation Kit (Gentra SYSTEMS) according to the manufacturer's protocol. Each genomic DNA sample was resuspended in 20 µl of 10 mM Tris-Cl (pH 8.0) and 1 mM EDTA (EDTA). Screening by PCR was performed using the following primer pair AYKObsrF2 (5'-GGTAGTGCAGT TTCGAATGGACAAAAGG-3'; SEQ ID NO: 38) and AYKObsrR2 (5'-TCAGG ATTTGCAG-CACACAGGAGTG-3'; SEQ ID NO: 39). The sequence of one primer is located in the KO vector, and the sequence of the other primer is located just outside of the integrated vector in the targeted endogenous locus. Therefore, the expected PCR product is detected only when the KO vector is integrated into the targeted locus by homologous recombination. The PCR reaction mixtures contained 17.9 µl water, 3 µl of 10× LA PCR buffer II (Mg$^{2+}$ plus), 4.8 µl of dNTP mixture, 10 µmol of forward primer, 10 µmol of reverse primer, 2 µl of genomic DNA, and 0.3 µl of LA Taq. Forty cycles of PCR were performed by incubating the reaction mixtures under the following conditions: 85° C. for three minutes, 94° C. for one minute, 98° C. for 10 seconds, and 68° C. for 8 minutes. After PCR, the reaction mixtures were analyzed by electrophoresis. Out of 322 screened clones, 22 clones generated the expected PCR products. As a result of sequencing of the PCR products, the KO vector designed to target AY allele was exclusively integrated into the AY allele in all the clones.

pBCµayKOhyg vector also was transfected to IgµU homozygous KO cell lines, except that the vector was digested with SalI before electroporation. As a result of screening of 453 hygromycin-resistant colonies, 29 clones were identified as a positive by PCR using the following primer pair ayKOhygF2 (5'-TGGTTGG CTTGTATGGAG-CAGCAGAC-3'; SEQ ID NO: 40) and ayKOhygR2 (5'-TAGG ATATGCAGCACACAGGAGTGTGG-3'; SEQ ID NO: 41). Sequencing of the PCR products demonstrated that the KO vector designed to target ay allele was exclusively integrated into the ay allele. Judging from the above results, it can be said that both the AY and ay KO vectors specifically target each allele in an allele-specific manner and produce correct targeted clones at a frequency of 7-8%. Chromatin transfer was performed as follows. In vitro-matured oocytes were enucleated at 20 hpm. Bovine IgµU knockout fibroblasts were trypsinized and washed in Ca/Mg Hank's Balanced Salt Solution (HBSS) and permeabilized by incubation of 50,000-100,000 cells in 31.25 units Streptolysin O (SLO; Sigma, St. Louis, Mo.) in 100 µl for 30 minutes in a 37° C. H$_2$O bath. Cell samples were incubated with propidium iodide and observed by fluorescent microscopy to monitor permeabilization based on uptake of the dye. Permeabilized fibroblasts were washed, pelleted, and incubated in 40 µl of mitotic extract prepared from MDBK cells containing an ATP-generating system (1 mM ATP, 10 mM creatine phosphate, and 25 µg/ml creatine kinase) for 30 minutes in a 37° C. H$_2$O bath. Cell samples were stained with Hoechst 33342 and observed by florescent microscopy to monitor chromatin condensation. At the end of incubation, the reaction mix was diluted with 500 µl cell culture media (alpha MEM with 10% FBS). These cells were pelleted and resuspended in TL HEPES and used for chromatin transfer in enucleated oocytes. Twelve fetuses were determined to be hemizygous IgµAY KO fetuses in which the bsrKO vector is integrated into AY allele of the IgµAY gene. Likewise, eleven fetuses were determined to be hemizygous IgµAY KO fetuses in which the hygKO vector is integrated into ay allele of the IgµAY gene. These fetuses were also IgµU$^{-/-}$. One of the IgµAY$^{-/+}$/IgµU$^{-/-}$ cell lines (A227, targeted in AY allele) was used for a second targeting experiment with pBCµayKOhyg. As a result of screening of 197 hygromycin-resistant colonies, 18 clones were identified as a positive by PCR using the primer pair (ayKOhygF2 and ayKOhygR2). Sequencing of the PCR products demonstrated that the KO vector designed to target ay allele was exclusively integrated into the ay allele, producing double homozygous knockout (IgµAY$^{-/-}$/IgµU$^{-/-}$) cells.

We produced IgµAY$^{-/-}$/IgµU$^{-/-}$ fetuses using the methods described herein. To examine whether these fetuses were B cell-deficient, we collected IgµAY$^{-/-}$/IgµU$^{-/-}$ fetuses at 180 days of gestation. From spleen, total RNA was extracted by using RNeasy Mini kit (QIAGEN). One microliter of total RNA was subjected to first-strand cDNA synthesis (SuperScript First-Strand Synthesis System for RT-PCR, Invitrogen), followed by RT-PCR. One RT-PCR reaction was carried out as below. The primer pair used (5'-CCCTCCTCTTTGT-GCTGTCA-3' (BL17; SEQ ID NO: 42) and 5'-GTTCAGGC-CATCATAGGAGG-3' (nBCpR2; SEQ ID NO: 43)) is compatible both with IgµAY and IgµU amplification. The PCR reaction mixtures contained 32.5 µl water, 5 µl of 10× Ex Taq buffer (TAKARA), 8 µl of dNTP mixture, 10 µmol forward primer, 10 µmol of reverse primer, 2 µl of the first-strand cDNA, and 0.5 µl of Ex Taq (TAKARA). Thirty five cycles of PCR were performed by incubating the reaction mixtures at the following conditions: 85° C. for three minutes, 94° C. for one minute, 98° C. for 10 seconds, 62° C. for 30 seconds and 72° C. for 1 minute. After PCR, the reaction mixtures were analyzed by electrophoresis. There were no positive PCR products in the IgµAY$^{-/-}$/IgµU$^{-/-}$ fetuses. After PCR, the reaction mixtures were analyzed by electrophoresis. No expression of IgµAY or IgµU could be detected. We also performed flow cytometry analysis to detect the presence of IgM heavy chain protein. No such protein could be detected.

To determine if the IgµU gene can, by itself, support B cell development, we generated IgµAY knockouts similarly as described above by using pbCFµayKOhyg and pbC-µAYKObsr vectors. From one IgµAY$^{-/-}$ cell line, we generated 180 day fetuses and performed RT-PCR on spleen tissue in an attempt to detect VDJ-rearranged IgµU transcripts. Sequence of the RT-PCR products showed VDJ-rearranged sequence of IgµU transcripts, exclusively, and disruption of IgµAY gene expression was confirmed. We confirmed, from sequence analysis, the presence of possible $V_H$ and $D_H$ segments associated with $J_H$-$C\mu_L$ segments, which comprise the corresponding FR1, CDR1, FR2, CDR2, FR3 and CDR3 regions. Furthermore, direct sequencing of the RT-PCR products clearly showed diversified sequence in the CDR3 region of IgµU transcripts as well as that of IgµAY. The sequence of IgµU cDNA appears to encode functional IgM-like polypeptides, which are slightly different from IgµAY, especially in FR4 and the constant region. These data demonstrate that the IgµU gene can be expressed independently of IgµAY expression, following functional VDJ-rearrangement, which included diversification of CDR3.

To investigate whether functional expression of IgµU could sufficiently execute B cell development independently of the classical pathway through IgµAY, we performed flow cytometry analysis in IgµAY$^{-/-}$ 180 day fetuses. We recognized significant populations of developing B cells (IgM$^+$B220$^+$), comparable to controls. This result indicates that IgµU protein can be displayed on the B cell surface. Next, to investigate generation of immature B cells (IgM$^+$Igλ$^+$), staining was done with both an anti-bovine IgM polyclonal antibody and an anti-bovine Igλ monoclonal antibody. Double positive B cells were detected, suggesting the presence of immature B cells where IgµU heavy chain couples with Igλ light chain to form B cell-receptors. Furthermore, we detected generation of mature B cells, recognized by anti-CD21 antibody, and confirmed gene expression of VDJ-rearranged bIgD gene by RT-PCR. This observation suggests that IgµU can support mature B cell development and elicit the expression of a VDJ-C$_\delta$ gene. Moreover, we detected the occurrence of class switching and expression of VDJ-rearranged bIgG, even though the γ constant region segment has not been identified as part of the IgµU gene cluster. Interestingly, the extent of diversification of CDR3 in the bIgG transcripts, from IgµAY$^{-/-}$ fetuses, was significantly less than that detected in IgµU$^{-/-}$ fetuses. However, CDR3 in IgµU transcripts in IgµAY$^{-/-}$ fetuses was diversified at a level comparable to that of IgµAY transcripts in IgµU fetuses. This result suggests that IgµU may be less efficient at generation of well-diversified IgG compared to the classical IgµAY locus, probably because the IgµU locus does not link, in cis, with the bIgG constant region. These data strongly suggest that IgμU can largely substitute for lack of IgμAY function in driving B cell development, but likely recruits γ constant region segments from the IgμAY locus by some trans-class switch mechanism.

From these results, it is demonstrated that there are two functional IgM loci, IgμAY and IgμU, in bovine and that double homozygous knockouts IgμAY$^{-/-}$/IgμU$^{-/-}$ are useful for B cell-deficiency.

Example 6

Production of Bovines that are Deficient in Prion Protein Expression

The present invention features the production of bovines that are deficient in prion protein expression. Although PrP$^{-/-}$ mice are viable and appear healthy, in cattle the effect of knocking out the gene had not previously been determined. In an attempt to generate PrP$^{-/-}$ cattle, we exploited a sequential gene targeting system for bovine fibroblasts described above. Male Holstein fibroblasts (cell line 4685, which is also IgμU$^{-/-}$) were transfected with a knockout vector (pBPrP(H) KOneo), and correctly targeted cells were cloned to generate PrP$^{-/+}$ fetuses at 40 days of gestation that were used to establish PrP$^{-/+}$ cell lines. Fetal cell lines were evaluated to confirm correct targeting by PCR genotyping. The PrP$^{-/+}$ cell line was then transfected with a second knockout vector (pBPrP(H) KOpuro) followed by selection and cloning to generate PrP$^{-/-}$ fetuses and cell lines. Correct targeting in cell lines was verified by PCR genotyping. Wild type, PrP$^{+/+}$/IgμU$^{-/-}$ (cell line 5112), heterozygous knockout, PrP$^{-/+}$IgμU$^{-/-}$ (cell line 8018), and homozygous knockout, PrP$^{-/-}$/IgμU$^{-/-}$ (cell line 1718) fibroblasts were used for embryonic cloning to produce calves (Table 4). In our first cloning series we obtained one calf each from PrP$^{+/+}$/IgμU$^{-/-}$ (calf 347; 5.9%), PrP$^{-/+}$/IgμU$^{-/-}$ (calf 341; 4.3%) and PrP$^{-/-}$/IgμU$^{-/-}$ (calf 342; 3.2%) cell lines (FIG. 15).

TABLE 4

Production of first series of cloned calves from PrP$^{-/-}$ fibroblast cell lines

| Genotype | Cell line ID | No. of recipients implanted | No. of calves born (%) | No. of calves survived (%) |
| --- | --- | --- | --- | --- |
| PrP$^{+/+}$/IgμU$^{-/-}$ | 5112 | 17 | 1 (5.9) | 1 (5.9) |
| PrP$^{-/+}$/IgμU$^{-/-}$ | 8018 | 23 | 2 (8.6) | 1 (4.3) |
| PrP$^{-/-}$/IgμU$^{-/-}$ | 1718 | 31 | 2 (6.4) | 1 (3.2) |

In order to verify the genotype of calves 341 and 342, we collected a small biopsy of skin from each calf and established fibroblast cell lines (FIG. 16A). No differences were observed in morphology or growth rate of fibroblasts from the two knockout genotypes and control fibroblasts. Genotyping was done by PCR using primer pairs that were specific for each targeted PrP gene allele (primer pairs; neoF7×neoR7 and puroF14×puroR14; FIG. 16B) followed by sequence analysis for confirmation. Additionally, we performed a second PCR (Kuroiwa et al., supra) to confirm the absence of the wild type PrP alleles (primer pairs; BPrPex3F×BPrPex3R, FIG. 16C). The results confirmed that calf 341 was a heterozygous PrP knockout and calf 342 was a homozygous PrP knockout. In addition, we performed a similar PCR analysis to confirm the absence of wild-type IgμU alleles using primer pairs: bCμf×bCμr (FIG. 16D) in calves 341 and 342, and, as expected, all four targeting events (PrP$^{-/-}$/IgμU$^{-/-}$) were confirmed. This represented the first generation of a double homozygous knockout (PrP$^{-/-}$/IgμU$^{-/-}$) calf, demonstrating that four rounds of gene targeting in primary somatic cells followed by embryonic cloning are compatible with generation of live calves.

To demonstrate functional inactivation of the PrP gene in calf 342, we extracted mRNA and total protein from the fibroblasts. As controls, we analyzed PrP$^{+/+}$/IgμU$^{-/-}$ calf 347 and PrP$^{-/+}$/IgμU$^{-/-}$ calf 341. For mRNA expression analysis, we performed RT-PCR (primer pairs; PrPmF3×PrPmR3, FIG. 17A) and then confirmed the disruption of PrP mRNA expression in PrP$^{-/-}$/IgμU$^{-/-}$ calf 342, while clear expression was detected in PrP$^{+/+}$/IgμU$^{-/-}$ calf 347 and PrP$^{-/+}$/IgμU$^{-/-}$ calf 341. For protein expression analysis, we performed a western blot using a mouse anti-bovine PrP monoclonal antibody. We detected appropriate bands for PrP$^{+/+}$/IgμU$^{-/-}$ calf 347 and PrP$^{-/+}$/IgμU$^{-/-}$ calf 341 but no band was observed for PrP$^{-/-}$/IgμU$^{-/-}$ calf 342 or negative control mouse fibroblasts (FIG. 17B). In addition, we collected brain samples from two PrP$^{-/-}$ calves that died within the first week after birth and performed western blot analysis on the samples. No PrP-positive bands were detected from the brain samples (FIG. 18). This result was also confirmed with a different mouse anti-bovine PrP monoclonal antibody (6H4, Prionics) in a separate laboratory. These data clearly demonstrate that the PrP gene is functionally inactivated in the PrP$^{-/-}$/IgμU$^{-/-}$ and PrP$^{-/-}$ calves.

All calves have been evaluated by either a licensed veterinarian or trained animal care technician. At one week and one month, calves 341 and 342, along with controls, were given physicals which included evaluation of the following parameters: body weight, body temperature, heart rate, heart sound, jugular vein distension, respiratory rate, respiratory sound, cough, presence of nasal discharge or eye abnormalities, appetite, general behavior (alert and active, sluggish, hyperactive), gait, posture, joints, hooves, feces (diarrhea, constipation), genitalia, and umbilical cord (dry, enlarged, inflamed, infected). In addition, blood samples were taken for standard hematology and serum chemistry. To date all parameters for calves 341 and 342 have been normal for these age groups.

For added verification, a second set of cloned PrP$^{-/-}$ embryos, which were only PrP$^{-/-}$ without any other genetic modification, were produced and transferred into 51 recipients. From these transfers, seven calves (14%) have been born (Table 5). These calves were verified by PCR genotyping and western blot analysis of peripheral blood lymphocytes (PBLs) isolated from blood biopsy (FIG. 19) to be PrP$^{-/-}$. Physical examination of the calves at one week did not reveal any obvious abnormalities, and there have been no apparent differences in phenotype between the PrP$^{-/-}$/IgμU$^{-/-}$ and PrP$^{-/-}$ calves to date.

TABLE 5

Production of first series of cloned calves from PrP$^{-/-}$ fibroblast cell lines

| Genotype | Cell line ID | No. of recipients implanted | No. of calves born (%) | No. of calves survived (%) |
| --- | --- | --- | --- | --- |
| PrP$^{-/-}$ | 5211 | 30 | 7 (23) | 5 (16) |
| PrP$^{-/-}$ | 5232 | 21 | 3 (14) | 2 (10) |

Methods

The results described in Example 6 were obtained using the following methods.

Embryonic Cloning

Cloned calves were produced using a chromatin transfer procedure. In vitro matured oocytes were enucleated at 20 h post maturation. Correctly targeted clones were permeabilized by incubation of about 50,000-100,000 cells in suspension with 31.2 U Streptolysin 0 (SLO; Sigma) in 100 µl HBSS for 30 min in a 37° C. $H_2O$ bath. Permeabilized cells were sedimented, washed, and incubated with 40 µl mitotic extract containing an ATP generating system (1 mM ATP, 10 mM creatine phosphate and 25 µg/ml creatine kinase) for 30 min at 38° C. At the end of the incubation, the reaction mix was diluted, sedimented, and washed. These cells were fused to enucleated oocytes, activated at 28 h post maturation with 5 µM calcium ionophore for 4 min, followed by 10/g/ml cycloheximide and 2.5 µg cytochalasin D for 5 h. After activation, CT embryos were washed and co-cultured with mouse fetal fibroblasts to blastocyst stage in vitro. Grade 1 and 2 blastocysts were selected and transferred into synchronized recipients. All animal work described in this section was done following a protocol approved by the Transova Genetics institutional animal care and use committee.

Cell Culture and Transfection

Holstein fetal male fibroblasts were cultured and electroporated with 30 µg of each knockout vector at 550 V and 50 µF using a GenePulser II (Bio-Rad). After 48 hours, the cells were selected using 500 µg/ml G418 or 1 µg/ml puromycin for two weeks, and the drug-resistant colonies were picked and transferred to replica plates; one for genomic DNA extraction (24-well plates) and the other for embryonic cloning (48-well plates).

Genomic PCR Analyses

Genomic DNA was extracted from fibroblasts originated from either ear biopsy or blood of $PrP^{-/-}$ homozygous KO calves using a PUREGENE DNA isolation Kit (Gentra SYSTEMS) and the manufacture's protocol. Each genomic DNA sample was resuspended in 50-100 µl of 10 mM Tris-Cl (pH 8.0) and 1 mM EDTA (EDTA). Confirmation by PCR was performed using the following primer pairs neoF7; 5'-TGT-CAAAGAGACACTCCTCATTTGTCTTCC-3' (SEQ ID NO: 44) and neoR7; 5'-TCATAGCCGAATAGCCTCTC-CACCC-3' (SEQ ID NO: 45) to detect the first targeted allele, and puroF14; 5'-TTGCTCCACCTTCC GTCTTCTGTC-3' (SEQ ID NO: 46) and puroR14; 5'-GTTGGCGCCTACCGG TGGATGTG-3' (SEQ ID NO: 47) to detect the second targeted allele. The PCR reaction mixtures contained 17.9 µl water, 3 µl of 10×LA PCR buffer II ($Mg^{2+}$ plus), 4.8 µl of dNTP mixture, 10 µmol forward primer, 10 µmol of reverse primer, 2 µl of genomic DNA, and 0.3 µl of LA Taq. Thirty cycles of PCR were performed by incubating the reaction mixtures at the following conditions: 85° C. for three minutes, 94° C. for one minute, 98° C. for 10 seconds, and 68° C. for 5 minutes. In addition, another PCR was performed to confirm the absence of (i) wild type PrP alleles using the following primer pairs: BPrPex3F; 5'-CCACATA GGCAGTTG-GATCC-3' (SEQ ID NO: 48) and BPrPex3R; 5'-ATAAGAGGCC TGCTCATGGC-3' (SEQ ID NO: 49) and (ii) IgµU alleles (for $PrP^{-/-}IgµU^{-/-}$ calves only) using the following primer pairs: BCµf; 5'-TGGTCACTCCAAGT GAGTCG-3' (SEQ ID NO: 50) and BCElr; 5'-TGGAGT-GAAATCAGGTGAA GG-3' (SEQ ID NO: 51). The PCR reaction mixtures contained 17.9 µl water, 3 pt of 10× Ex Taq buffer, 4.8 µl of dNTP mixture, 10 µmol forward primer, 10 µmol of reverse primer, 2 µl of genomic DNA, and 0.3 µl of Ex Taq. Thirty cycles of PCR were performed by incubating the reaction mixtures at the following conditions: 85° C. for three minutes, 94° C. for one minute, 98° C. for 10 seconds, 60-62° C. for 30 seconds, and 72° C. for 1 minute. Following PCR, the reaction mixtures were analyzed by electrophoresis.

RT-PCR

From biopsy samples, total RNA was extracted using an RNeasy Mini kit (QIAGEN). One microliter of total RNA was subjected to first-strand cDNA synthesis (SuperScript First-Strand Synthesis System for RT-PCR, Invitrogen), followed by RT-PCR. The RT-PCR was carried out using the primer pair: 5'-AA GAAGCGACCAAAACCTGG-3' (SEQ ID NO: 52) and 5'-GTAACGGTGCAT GTTTTCACG-3' (SEQ ID NO: 53). The PCR reaction mixtures contained 32.5 pt water, 5 µl of 10× Ex Taq buffer (TAKARA), 8 µl of dNTP mixture, 10 µmol forward primer, 10 µmol of reverse primer, 2 µl of the first-strand cDNA, and 0.5 µl of Ex Taq (TAKARA). Thirty five cycles of PCR were performed by incubating the reaction mixtures at the following conditions: 85° C. for three minutes, 94° C. for one minute, 98° C. for 10 seconds, 62° C. for 30 seconds and 72° C. for 1 minute. For detection of bovine β-actin mRNA expression, primers bBAF (5'-ACATCCGCAAGGACCTCTAC-3'; SEQ ID NO: 54) and bBAR (5'-AACC GACTGCTGTCACCTTC-3'; SEQ ID NO: 55) were used under the same PCR conditions. To exclude the possibility of genomic DNA contamination, another set of RT-PCR reactions without reverse-transcriptase was also performed. Following PCR, the reaction mixtures were analyzed by electrophoresis. There were no positive PCR products in any biopsy sample prepared from a $PrP^{-/-}$ or $PrP^{-/-} IgµU^{-/-}$ KO calf. This result verified the complete absence of prion gene expression in the calves.

Western Blotting

From biopsy or blood samples of live calves or brain samples of dead calves, total protein was extracted and the protein content was quantified using a Bio-Rad protein assay reagent. Western blot analysis was carried out by running approximately 75 µg of protein sample on a 12% SDS PAGE gel under non reducing conditions. The proteins were then transferred to a nitrocellulose membrane, and the membrane was stained using an anti-bovine prion protein monoclonal antibody (F 89/160.1.5; Alexis Biochemicals) as a primary antibody and secondarily stained with peroxidase-labeled affinity purified antibody directed to mouse IgG(H+L). The stained membrane was developed using an ECL plus western blotting detection system (Amersham Bioscience) and exposed to a Biomax light film by film developer. As a positive control, recombinant bovine PrP protein (Alexis Biochemicals) was used. As a negative control, protein extracts from murine fibroblasts were analyzed. As an internal positive control, the same blot was similarly stained with an anti-CDC2 monoclonal antibody. No prion protein band was detected in any biopsy sample prepared from a $PrP^{-/-}$ or $PrP^{-/-}IgµU^{-/-}$KO calf. This result verified the complete absence of prion protein expression in the calves.

Example 7

Production of Bovines that are Deficient in Prion Protein and IgM Heavy Chain Expression Transfection of $IgµU^{-/-} PrP^{-/-}$ cell line 8454 with pBC-µAYKObsr vector was performed using the following standard electroporation protocol. The medium used to culture the bovine fetal fibroblasts contained 500 ml Alpha MEM (Gibco, 12561-049), 50 ml fetal calf serum (Hy-Clone #ABL13080), 5 ml penicillin-streptomycin (SIGMA), and 1 ml 2-mercaptoethanol (Gibco/BRL #21985-023). On the day prior to transfection, cells were seeded on a T175 tissue culture flask with a confluency of 80-100%, as determined by microscopic examination. On the day of transfection, about 107 bovine fibroblasts cells were trypsinized and washed once with alpha-MEM medium. After resuspension of the cells in 800 µl of alpha-MEM, 30 µg of the SrfI-digested KO vector (pBCµAYKObsr vector) dissolved in HEPES-buffered saline (HBS) containing 1 mM spermidine was added to the cell suspension and mixed well by pipetting. The cell-DNA suspension was transferred into an electroporation cuvette and electroporated at 550 V and 50 µF. After that, the electroporated cells were plated onto thirty 48-well plates with the alpha-MEM medium supplemented with the serum. After a 48 hour-culture, the medium was replaced with medium containing 10 µg/ml of blasticidine, and the cells were cultured for 2-3 weeks to select blasticidine resistant cells. After selection, all colonies which reached close to 100% confluency were divided into two replica plates (24-well and 48-well plates): one for genomic DNA extraction, and the other plate for nuclear transfer. Genomic DNA was extracted from the colonies to screen for the desired homologous recombination events by PCR.

As described above, the genomic DNA was independently extracted from each 24-well using the PUREGENE DNA isolation Kit (Gentra SYSTEMS) according to the manufacture's protocol. Each genomic DNA sample was resuspended in 20 µl of 10 mM Tris-Cl (pH8.0) and 1 mM EDTA (EDTA). Screening by PCR was performed using the following primer pair AYKObsrF2 (5'-GGTAGTGCAGTTTCGAATGGA-CAAAAGG-3'; SEQ ID NO: 56) and AYKObsrR2 (5'-TCAGGATTTGCAGCACACAGGAGTG-3'; SEQ ID NO: 57). The sequence of one primer is located in the KO vector, and the sequence of the other primer is located just outside of the integrated vector in the targeted endogenous locus. Therefore, the expected PCR product is detected only when the KO vector is integrated into the targeted locus by homologous recombination. The PCR reaction mixtures contained 17.9 µl water, 3 µl of 10× LA PCR buffer II ($Mg^{2+}$ plus), 4.8 µl of dNTP mixture, 10 µmol of forward primer, 10 µmol of reverse primer, 2 µl of genomic DNA, and 0.3 µl of LA Taq. Forty cycles of PCR were performed by incubating the reaction mixtures under the following conditions: 85° C. for three minutes, 94° C. for one minute, 98° C. for 10 seconds, and 68° C. for 8 minutes. After PCR, the reaction mixtures were analyzed by electrophoresis. Out of 198 screened clones, 14 clones generated the expected PCR products. As a result of sequencing of the PCR products, the KO vector designed to target AY allele was exclusively integrated into the AY allele in all the clones.

The above knockout ($IgµAY^{-/+}IgµU^{-/-}PrP^{-/-}$) cells or the nuclei from these cells were used in any of the nuclear transfer methods described herein to generate an $IgµAY^{-/+}IgµU^{-/-}PrP^{-/-}$ knockout ungulate (e.g., a knockout bovine calf). If desired, cells from a knockout fetus or live ungulate can be used as described below to generate homozygous prion knockout cells. In one particular method, fibroblasts (e.g., bovine primary fetal fibroblasts) were synchronized in mitosis with 1 µg/ml nocodazole for 18 hours, harvested by mitotic shake-off, and washed twice in phosphate buffered saline and once in cell lysis buffer (20 mM Hepes, pH 8.2, 5 mM $MgCl_2$, 10 mM EDTA, 1 mM DTT and protease inhibitors). Sedimented cells were resuspended in one volume of ice-cold cell lysis buffer, allowed to swell on ice for one hour, and Dounce-homogenized using a tight-fitting glass pestle. The lysate was centrifuged at 15,000×g for 15 minutes at 4° C., and the supernatant (mitotic extract) was aliquoted, frozen in liquid nitrogen, and stored at −80° C. Fresh or frozen extracts were used. In vitro-matured oocytes were enucleated at 20 hpm. Transfected bovine fetal fibroblasts from selected colonies were washed in $Ca^{2+}/Mg^{2+}$-free Hank's Balanced Salt Solution (HBSS) and permeabilized by incubation of cells in suspension with 31.2 U Streptolysin 0 (SLO; Sigma) in 100 µl HBSS for 30 minutes in an approximately 37° C. water bath. Permeabilization was assessed by uptake of the membrane impermeant DNA stain, propidium iodide (0.1 µg/ml). Permeabilized fibroblasts were sedimented, washed, and incubated in 40 µl mitotic extract containing an ATP-generating system (1 mM ATP, 10 mM creatine phosphate, and 25 µg/ml creatine kinase) for 30-45 minutes at approximately 37° C. Aliquots were labeled with 0.1 µg/ml Hoechst 33342 to monitor chromatin condensation. At the end of incubation, the reaction mixture was diluted with 500 µl Alpha MEM/10% fetal bovine serum (Hyclone). Cells were fused to enucleated oocytes; oocytes were activated at 28 hpm, and embryos cultured to the blastocyst stage in vitro. Two embryos were transferred per recipient female. Pregnancies were monitored by ultrasonography, and C-sections were performed on recipients to recover fetuses for cell line production.

pBCµayKOhyg vector was transfected to the above $IgµAY^{-/+}IgµU^{-/-}PrP^{-/-}$ cell lines, except that the vector was digested with SalI before electroporation. As a result of screening of 119 hygromycin-resistant colonies, four clones were identified as being positive by PCR using primer pair ayKOhygF2 (5'-TGGTTGG CTTGTATGGAGCAGCA-GAC-3'; SEQ ID NO: 58) and ayKOhygR2 (5'-TAGG ATAT-GCAGCACACAGGAGTGTGG-3'; SEQ ID NO: 59). Sequencing result of the PCR products demonstrated that the KO vector designed to target ay allele was exclusively integrated into the ay allele. From the above results, we conclude that both the AY and ay KO vectors can specifically target each allele in an allele-specific manner and produce correct targeted clones.

Using the methods described herein, we performed chromatin transfer from the identified $IgµAY^{-/-}IgµU^{-/-}PrP^{-/-}$ colonies and finally generated four $IgµAY^{-/-}IgµU^{-/-}PrP^{-/-}$ fetuses, from which we established four cell lines. Moreover, we obtained one $IgµAY^{-/-}IgµU^{-/-}PrP^{-/-}$ calf. Genotyping was performed as follows. The genomic DNA was extracted from fibroblasts originated from ear biopsy or from blood of the $IgµAY^{-/-}IgµU^{-/-}PrP^{-/-}$ triple homozygous KO calf using the PUREGENE DNA isolation Kit (Gentra SYSTEMS) according to the manufacture's protocol. Each genomic DNA sample was resuspended in 50-100 µl of 10 mM Tris-Cl (pH8.0) and 1 mM EDTA (EDTA). Confirmation by PCR was performed using the following primer pair 5'-TCTCTGGT-GACGGCAATAGC-3' (BCpf2; SEQ ID NO: 60) and 5'-CT-TCGTGAGGAAGATGTCGG-3' (BCtr2; SEQ ID NO: 61), which is compatible both with IgµAY and IgµU amplification, to confirm the absence of wild-type alleles of the IgµAY and IgµU genes, and another primer pair BPrPex3F (5'-CCA-CATAGGCAGTTGGATCC-3' (SEQ ID NO: 629) and BPrPex3R (5'-ATAAGAGGCCTGCTCATGGC-3' (SEQ ID NO: 63) to confirm the absence of wild-type alleles of the PrP gene. The PCR reaction mixtures contained 17.9 µl water, 3 µl of 10× Ex Taq buffer, 4.8 µl of dNTP mixture, 10 µmol forward primer, 10 µmol of reverse primer, 2 µl of genomic DNA, and 0.3 µl of Ex Taq. Thirty cycles of PCR were performed by incubating the reaction mixtures at the following conditions: 85° C. for three minutes, 94° C. for one minute, 98° C. for 10 seconds, 60-62° C. for 30 seconds and 72° C. for 1 min. After PCR, the reaction mixtures were analyzed by electrophoresis. The results demonstrated that the calf born was $IgµAY^{-/-}IgµU^{-/-}PrP^{-/-}$.

Example 8

Verification of the Absence of Prion Protein Expression in the IgμAY$^{-/-}$IgμU$^{-/-}$PrP$^{-/-}$ Triple Homozygous KO Calf From blood samples taken from the IgμAY$^{-/-}$IgμU$^{-/-}$PrP$^{-/-}$ triple homozygous KO calf, total protein was extracted and the protein content was quantified by using Bio-Rad protein assay reagent. Western blot analysis was carried out by running approximately 75 μg of protein sample on a 12% SDS page gel at non-reducing condition. The proteins were transferred to nitrocellulose membrane and the membrane was stained with anti-bovine Prion protein monoclonal antibody (F 89/160.1.5 from Alexis Biochemicals) as a primary antibody, followed by a peroxidase-labeled affinity purified secondary antibody to mouse IgG(H+L). The stained membrane was developed by ECL plus western blotting detection system (Amersham Bioscience) and exposed to Biomax light film by film developer. As a positive control, recombinant bovine PrP protein (Alexis Biochemicals) was used. As a negative control, protein extract from murine fibroblasts was used.

In the biopsy sample prepared from the IgμAY$^{-/-}$IgμU$^{-/-}$PrP$^{-/-}$ triple homozygous KO calf, no band was stained with antibody. This result verifies the complete absence of prion protein expression in the calf.

Example 9

Verification of the Absence of IgM Protein Expression in the IgμAY$^{-/-}$IgμU$^{-/-}$PrP$^{-/-}$ Triple Homozygous KO Calf To confirm that the IgμAY$^{-/-}$IgμU$^{-/-}$PrP$^{-/-}$ triple homozygous KO calf lacked IgM protein, we performed flow cytometry analysis as described below. Peripheral blood was collected from the newborn calf by jugular venipuncture into heparinized tubes. Whole white blood cells (leukocytes) were isolated from heparinized blood by red blood cell lysing using RBC-lysis buffer (Sigma, St. Louis, Mo.) and washing twice with sterile Hanks Buffered Salt Solution (HBSS) (Sigma, St. Louis, Mo.). Cells were resuspended in FACS staining medium (Phosphate Buffered Saline containing 4% horse serum or goat serum, 2 mM EDTA, and 0.2% sodium azide) and incubated for 30 minutes at room temperature for blocking non-specific binding. Sheep anti-bovine IgM-FITC (Bethyl Laboratories, Mongomery, Tex.) or donkey anti-sheep/bovine Ig-biotin antibody (Amersham Biosciences, Piscataway, N.J.) followed by Strepavidin-FITC or Sterpavidin-PE secondary antibody (Caltag Laboratories, Burlingame, Calif.) was used to label bovine surface IgM (sIgM) on the B cells. To label surface B220 marker on developing bovine B cells, mouse anti-bovine B220 (CD45R) antibody clone GS5A (VMRD, Pullman, Wash.) followed by anti-mouse IgG1-PE secondary antibody (Caltag Laboratories, Burlingame, Calif.) was used. Mouse anti-bovine CD21 Clone MCA1424 and mouse anti-ruminant CD43 Clone 1096 from Serotec Inc. (Raleigh, N.C.) antibodies followed by anti-mouse IgG1-PE secondary antibody (Caltag Laboratories, Burlingame, Calif.) were used to label surface CD21 and CD43 markers on bovine B cells. Fifty microliter cell suspension containing 10$^6$ cells (WBCs) in FACS staining medium were used for staining with each surface marker antibody alone as well as in combinations in V-bottom microtiter wells or tubes. Cells were incubated with primary antibodies at room temperature in dark for 20-30 minutes and washed twice with FACS wash buffer (Phosphate Buffered Saline containing 2 mM EDTA and 0.2% sodium azide) by centrifugation. Cells were resuspended again in 50 μl of FACS staining medium and incubated with appropriate fluorescent labeled secondary antibodies for 15-20 minutes at room temperature in dark. Finally cells were washed twice with FACS wash buffer and fixed with 2-4% formaldehyde in PBS. Surface labeled fixed cells were then analyzed and data acquired in FACScan flow cytometer (BD Biosciences, San Diego, Calif.). The list mode file data were finally analyzed using WinMDI software for single color or dual color profiles. The FACS result demonstrated complete absence of any developing B cell in the triple homozygous KO calf.

Example 10

HAC Transfer into IgμAY$^{-/-}$/IgμU$^{-/-}$ Cell Lines

One use of animals having reduced IgM levels is the generation of xenogenous antibodies. One method of producing xenogenous antibody is to produce an animal having one or more human artificial chromosomes expressing antibody heavy chain and/or light chain. To this end, ΔΔHAC (λHAC) and κHAC were transferred from DT40 cell hybrids to Chinese hamster ovary (CHO) cells using microcell-mediated chromosome transfer (MMCT) (Kuroiwa et al. (2000) Nature Biotech. 18:1086-1090). The CHO clone containing λHAC ("ΔΔC10 clone") was cultured in F12 (Gibco) medium supplemented with 10% FBS (Gibco), 1 mg/ml of G418, and 0.2 mg/ml of hygromycin B at 37° C. and 5% CO$_2$. The ΔΔC10 clone was expanded into twelve T25 flasks. When the confluency reached 80-90%, colcemid (Sigma) was added to the medium at a final concentration of 0.1 μg/ml. After three days, the medium was exchanged with DMEM (Gibco) supplemented with 10 μg/ml of cytochalacin B (Sigma). The flasks were centrifuged for 60 minutes at 8,000 rpm to collect microcells. The microcells were purified through 8, 5, and 3-μm filters (Costar) and then resuspended in DMEM medium. The microcells were used for fusion with bovine fibroblasts as described below.

Bovine fetal fibroblasts were cultured in A-MEM (Gibco) medium supplemented with 10% FBS (Gibco) at 37° C. and 5% CO$_2$. The fibroblasts were expanded in a T175 flask. When the confluency reached 70-80%, the cells where detached from the flask with 0.05% trypsin. The fibroblast cells were washed twice with DMEM medium and then overlayed on the microcell suspension. After the microcell-fibroblast suspension was centrifuged for five minutes at 1,500 rpm, PEG1500 (Roche) was added to the pellet according to the manufacturer's protocol to enable fusion of the microcells with the bovine fibroblasts. After fusion, the fused cells were plated into six 24-well plates and cultured in α-MEM medium supplemented with 10% FBS for 24 hours. The medium was then exchanged with medium containing 0.8 mg/ml of G418. After growth in the presence of the G418 antibiotic for about two weeks, the G418 resistant, fused cells were selected. These G418-resistant clones were used for chromatin transfer, as described herein.

Example 11

Expression of Human IgM, IgG, and Igλ in HAC/IgμAY$^{-/-}$/IgμU$^{-/-}$ Fetuses at 180 Days of Gestation To examine whether HAC/IgμAY$^{-/-}$IgμU$^{-/-}$ fetuses could express human immunoglobulin such as IgM, IgG, Igλ and Igκ, we collected HAC/IgμAY$^{-/-}$/IgμU$^{-/-}$ fetuses at 180 days of gestation. Total RNA was extracted from the spleen by using RNeasy Mini kit (QIAGEN). One microliter of total RNA was subjected to first-strand cDNA synthesis (SuperScript First-Strand Synthesis System for RT-PCR, Invitrogen), followed by RT-PCR. To detect human IgM expression, RT-PCR reaction was carried out using primer pair; 5'-AGGCCAGCATCTGCGAG GAT-3' (CH3—F3; SEQ ID NO: 64) and 5'-GTGGCAGCAAGTAGACATCG-3' (CH4-R2; SEQ ID NO: 65). For human IgG expression, the following primers were used: 5'-CAGGTGCAGCTGGTGCAGTCTGG-3' (SEQ ID NO: 66, 5'-CAGGTCACCTTGAAGGAGTCTGG-3' (SEQ ID NO: 67), 5'-GAGGTGCAGCTGGTGGAGTCTGG-3' (SEQ ID NO: 68), 5'-CAGGTGCAGCTGCAGGAG TCGGG-3' (SEQ ID NO: 69), 5'-GAGGTGCAGCTGGTGCAGTCTGG-3', 5'-CAGGTACAGCTGCAGCAGTCAGG-3' (SEQ ID NO: 70), and 5'-CAGGTGCA GCTGGTGCAGTCTGG-3' (SEQ ID NO: 71) (VH All Mix) in combination with 5'-CACCACGCTGCTGAGGGAGTAGAGT-3' (hCg1R2; SEQ ID NO: 72). For human Igλ expression, the following primer pair was used: 5'-TCCTCTGAGGAGCTTCAAGC-3' (hCL-F2; SEQ ID NO: 73) and 5'-AGGGTTTATTGAGT GCAGGG-3' (hCL-R2; SEQ ID NO: 74). The PCR reaction mixtures contained 32.5 μl water, 5 μt of 10× Ex Taq buffer (TAKARA), 8 μl of dNTP mixture, 10 μmol forward primer, 10 μmol of reverse primer, 2 μl of the first-strand cDNA, and 0.5 μl of Ex Taq (TAKARA). Thirty five cycles of PCR were performed by incubating the reaction mixtures at the following conditions: 85° C. for three minutes, 94° C. for one minute, 98° C. for 10 seconds, 60-62° C. for 30 seconds and 72° C. for 1 minute. After PCR, the reaction mixtures were analyzed by electrophoresis. From a λHAC/IgμAY$^{-/-}$/IgμU$^{-/-}$ fetus, human IgM, IgG, and Igλ expression was detected by RT-PCR.

To confirm cell surface expression of human immunoglobulin at the protein level, we also performed flow cytometry analysis as described above. Goat anti-human IgM-FITC (Bethyl Laboratories, Mongomery, Tex.), goat anti-human IgM-FITC (Serotec Inc., Raleigh, N.C.), or goat anti-human IgM-PE (Serotec Inc., Raleigh, N.C.) antibody was used to label the human sIgM expressed on the peripheral blood B cells of ≧180 day HAC fetuses. To detect the light chains expressed on the B cells, goat anti-human lambda-FITC antibody (Bethyl Laboratories) or goat anti-human lambda-PE antibody (Serotec Inc) was used. For dual color analysis, a FITC-labeled anti-human IgM antibody and PE-labeled light chain antibody combination was used. We detected cell populations that were positive with the anti-human IgM and light chain antibodies. Furthermore, we performed sandwich ELISA analysis to detect secreted human IgG in λHAC/IgμAY$^{-/-}$/IgμU$^{-/-}$ calves using an affinity purified capture antibody and an appropriate HRP-enzyme labeled detection antibody. Details of the capture antibody and detection antibody for each assay are given in Table 6 below.

TABLE 6

| Assay | Standards (Calibrator) | Capture antibody | Detection antibody |
| --- | --- | --- | --- |
| Human IgG ELISA | Human Reference Serum (Bethyl laboratories) | Goat anti-human IgG, affinity purified or goat anti-human IgG-Fc specific, affinity purified (Bethyl laboratories) | Goat anti-human IgG-HRP conjugated (Bethyl laboratories) |

The capture antibody diluted in coating buffer (0.05 M sodium carbonate, pH 9.6) was coated on the microtiter plates (Nunc ImmunoMaxiSorp Elisa plates) by incubating at room temperature for 1.5 hours. After coating the capture antibody, the plates were washed with phosphate buffered saline (PBS)/Tween 20 buffer 3-5 times using an automated plate washer. Appropriate standards (Calibrators) were added in serial dilutions for quantification using a standard curve. Positive controls and negative controls were included in all assays for QC check. Serum samples from λHAC/IgμAY$^{-/-}$/IgμU$^{-/-}$ calves were added then into duplicate wells in four serial dilutions and incubated for 1 hour at room temperature. After serum immunoglubulins were captured, the plates are washed again with PBS-Tween buffer 3-5 times using automated plate washer. HRP-enzyme labeled appropriate detection antibody was added into all the wells and incubated for 1 hour at room temperature. At the end of incubation, the plates were washed again with PBS/Tween buffer 3-5 times using automated plate washer. The bound antibodies were detected by adding TMB-Substrate solution (KPL Inc, Gaithersburg, Mass.) and incubating for 10-20 minutes at room temperature. The reaction was stopped by addition of 10% phosphoric acid. The plates were then read on a microtiter plate reader using KC4 software. Data were analyzed by KC4 software and values were determined by interpolation on a four-parameter standard curve. In blood sample collected at 14 days after birth, 7.1 μg/ml of human IgG was detected by ELISA.

Other Embodiments

All publications and patents cited in this specification are incorporated herein by reference as if each individual publication or patent were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A transgenic bovine whose genome comprises homozygous mutations of both alleles of two different unrearranged IgM heavy chain loci, said mutations disrupting IgM heavy chain production and said transgenic bovine producing less than 10% of endogenous IgM heavy chain relative to a control bovine lacking the mutations.

2. The transgenic bovine of claim 1, wherein said bovine lacks functional IgM heavy chain.

3. The transgenic bovine of claim 1, wherein at least one mutation is by the insertion of an exogenous sequence, stop codon, or both.

4. A somatic cell obtained from the transgenic bovine of claim 1, whose genome comprises homozygous mutations of both alleles of two different IgM heavy chain loci, said mutations disrupting IgM heavy chain production.

5. The transgenic bovine somatic cell of claim 4, wherein one of said loci is IgμU and one of said loci is IgμAY.

6. The cell of claim 4, wherein said cell is a B cell.

7. The transgenic bovine of claim 1, wherein one of said loci is IgμU.

8. The transgenic bovine of claim 1, wherein one of said loci is IgμAY.

9. The transgenic bovine of claim 1, wherein one of said loci is IgμU and one of said loci is IgμAY.

10. The transgenic bovine somatic cell of claim 4, wherein one of said loci is IgμU.

11. The transgenic bovine somatic cell of claim 4, wherein one of said loci is IgμAY.

12. The transgenic bovine somatic cell of claim 4, wherein at least one mutation is by the insertion of an exogenous sequence, stop codon, or both.

13. The transgenic bovine of claim 1, wherein said homozygous mutations occur at different positions in said loci.

14. The transgenic bovine of claim 1, wherein said homozygous mutations result from different insertions.

15. The transgenic bovine of claim 1, wherein said homozygous mutations result from insertion of different exogenous sequences, or stop codons, or both.

16. The transgenic bovine of claim 1, wherein said bovine is an adult bovine, fetal bovine, or bovine embryo.

17. The transgenic bovine somatic cell of claim 4, wherein said homozygous mutations occur at different positions in said loci.

18. The transgenic bovine somatic cell of claim 4, wherein said homozygous mutations result from different insertions.

19. The transgenic bovine somatic cell of claim 4, wherein said homozygous mutations result from insertion of different exogenous sequences, or stop codons, or both.

* * * * *

UNITED STATES PATENT AND TRADEMARK OFFICE
CERTIFICATE OF CORRECTION

PATENT NO.        : 7,420,099 B2                                          Page 1 of 4
APPLICATION NO. : 11/111310
DATED             : September 2, 2008
INVENTOR(S)       : Robl et al.

It is certified that error appears in the above-identified patent and that said Letters Patent is hereby corrected as shown below:

On the Title Page, Item (56), under References Cited, under OTHER
   PUBLICATIONS,
   In Jonak et al., replace "Hybridomonas" with --Hybridomas--;
   In Griffiths et al., replace "Sytem" with --System--;
   In Sun et al., replace "Immumnology" with --Immunology--;
and
   In Park et al., replace "Embyros" with --Embryos--;

Column 1, Line 51, replace "galactocyltransferase" with
   --galactosyltransferase--;

Column 3, Lines 48-49, replace "transgenic ungulate ungulate"
   with --transgenic ungulate--;

Column 5, Line 53, replace "at least two the" with
   --at least two of the--;

Column 6, Line 14, replace "intravenenous" with
   --intravenous--;

Column 7,
   Line 39, replace "odifications" with --modifications--;
   Line 53, replace "to the their" with --to their--; and
   Line 58, replace "Igµgenes" with --Igµ genes--;

Column 8, Line 37, replace "side" with --sides--;

Column 11, Line 12, replace "multiallellic" with
   --multiallelic--;

Column 13, Line 5, replace "nuclioplasmin" with
   --nucleoplasmin--;

Signed and Sealed this

Twenty-fourth Day of August, 2010

David J. Kappos
*Director of the United States Patent and Trademark Office*

Column 16, Line 36, replace "PrP$^{-/+}$(341)" with --PrP$^{-/+}$ (341)--;

Column 18, Line 31, replace "xenotransplantion" with
--xenotransplantation--;

Column 19, Line 56, replace "Ig," with --Igµ--;

Column 20, Line 63, replace "estation" with --gestation--;

Column 23,
Line 6, replace "IgpU" with --IgµU--; and
Line 66, replace "polypetide" with --polypeptide--;

Column 25, Line 28, replace "inactive" with --inactivate--;

Column 26, Line 59, replace "method" with --methods--;

Column 29, Line 22, replace "therefor" with --therefore--;

Column 31,
Line 1, replace "IgµU-/+" with --IgµU$^{-/+}$--;
Line 3, replace "IgµU-/+" with --IgµU$^{-/+}$--; and
Line 5, replace "IgµU-/+" with --IgµU$^{-/+}$--;

Column 34,
Line 43, replace "was," with --was--; and
Line 49, replace "Kopuro" with --KOpuro--;

Column 36,
Line 20, replace "IgµU-/-" with --IgµU$^{-/-}$--;
Line 40, replace "ran" with --run--; and
Line 59, replace both "10 µmol" with --10 pmol--;

Column 37, Line 7, replace "Igµsequence" with --Igµ sequence--;

Column 38,
Line 21, replace "pBCgAYKObsr" with --pBCµAYKObsr--;
Line 33, replace "1" with --10$^7$--;
Line 45, replace "blasticidine" with --blasticidin--; and
Line 46, replace "blasticidine" with --blasticidin--;

Column 39,
Line 1, replace "10 µmol" with --10 pmol--; and
Line 2, replace "10 µmol" with --10 pmol--;

Column 40,
    Line 2, replace "nBCpR2" with --mBCµR2--;
    Line 5, replace "10 µmol" with --10 pmol--;
    Line 6, replace "10 µmol" with --10 pmol--;
    Line 20, replace "pbCFµayKOhyg" with --pbCµayKOhyg--; and
    Line 64, replace "IgµU" with --IgµU$^{-/-}$--;

Column 43,
    Line 17, replace "10/g/ml" with --10 µg/ml--;
    Line 50, replace both "10 µmol" with --10 pmol--;
    Line 62, replace "BCElr" with --BCµr--;
    Line 64, replace "3 pt" with --3 µl--;
    Line 65, replace "10 µmol" with --10 pmol--; and
    Line 66, replace "10 µmol" with --10 pmol--;

Column 44,
    Line 14, replace "pt" with --µl--; and
    Line 15, replace both "10 µmol" with --10 pmol--;

Column 45,
    Line 4, replace "107" with --10$^7$--;
    Line 15, replace "blasticidine" with --blasticidin--;
    Line 16, replace "blasticidine" with --blasticidin--;
    Line 24, replace "24-well" with --24-well plate--;
    Lines 25-26, replace "manufacture's" with
--manufacturer's--; and
    Line 39, replace both "10 µmol" with --10 pmol--;

Column 46,
    Line 50, replace "BCpf2" with --BCµf2--;
    Line 51, replace "BCtr2" with --BCµr2--;
    Line 59, replace "10 µmol" with --10 pmol--; and
    Line 60, replace "10 µmol" with --10 pmol--;

Column 47,
    Line 38, replace "venipunture" with --venipuncture--;
    Line 48, replace "Mongomery" with --Montgomery--; and
    Lines 50-51, replace "Sterpavidin-PE" with --Strepavidin-PE--;

Column 48, Line 35, replace "cytochalacin B" with
    --cytochalasin B--;

Column 49,
    Line 24, replace "5 µt" with --5 µl--;
    Line 25, replace both "10 µmol" with --10 pmol--; and
    Line 38, replace "Mongomery" with --Montgomery--;

Column 50, Line 27, replace "immunoglubulins" with
--immunoglobulins--.